US005883251A

United States Patent [19]

Hansen, Jr. et al.

[11] Patent Number: 5,883,251
[45] Date of Patent: Mar. 16, 1999

[54] AZEPINE DERIVATIVES USEFUL AS NITRIC OXIDE SYNTHASE INHIBITORS

[75] Inventors: Donald W. Hansen, Jr., Skokie; E. Ann Hallinan, Evanston; Timothy J. Hagen, Gurnee; Steven W. Kramer, DesPlaines, all of Ill.; Suzanne Metz, Chesterfield, Mo.; Karen B. Peterson, Vernon Hills; Dale P. Spangler, Deerfield, both of Ill.; Mihaly V. Toth; Kam F. Fok, both of St. Louis, Mo.; Arija A. Bergmanis, DesPlaines, Ill.; R. Keith Webber, St. Peters, Mo.; Mahima Trivede, Glenview, Ill.; Foe S. Tjoeng, Manchester, Mo.; Barnett S. Pitzele, Skokie, Ill.

[73] Assignee: G. D. Searle & Co., Chicago, Ill.

[21] Appl. No.: 977,621

[22] Filed: Nov. 25, 1997

Related U.S. Application Data

[63] Continuation of Ser. No. 425,831, Apr. 20, 1995, abandoned.
[51] Int. Cl.⁶ .................................................. C07D 223/02
[52] U.S. Cl. ........................... 540/596; 540/484; 540/597
[58] Field of Search ................................... 540/596, 484, 540/597, 598

[56] References Cited

U.S. PATENT DOCUMENTS

| | | | |
|---|---|---|---|
| 2,049,582 | 8/1936 | Ziegler | 260/127 |
| 3,109,848 | 11/1963 | Bortnick et al. | 260/313 |
| 3,121,093 | 2/1964 | Bortnick et al. | 260/313 |
| 3,132,151 | 5/1964 | Bortnick et al. | 260/313 |
| 3,501,487 | 3/1970 | Poos | 260/296 |
| 3,563,994 | 2/1971 | Wollweber et al. | 260/293 |
| 3,694,432 | 9/1972 | Hershenson | 260/239 B |
| 3,725,435 | 4/1973 | Poos | 260/326.5 |
| 3,816,457 | 6/1974 | Grisar et al. | 260/329 |
| 4,046,909 | 9/1977 | Rasmussen et al. | 424/274 |
| 4,061,746 | 12/1977 | Blohm et al. | 424/244 |
| 4,126,613 | 11/1978 | Grisar et al. | 260/239 B |
| 4,126,621 | 11/1978 | Grisar et al. | 260/239 B |
| 4,153,235 | 5/1979 | Grisar et al. | 260/239 B |
| 4,443,468 | 4/1984 | Maillard et al. | 424/274 |
| 4,523,020 | 6/1985 | Moormann et al. | 548/559 |
| 4,525,476 | 6/1985 | Butler et al. | 514/326 |
| 4,533,739 | 8/1985 | Pitzele et al. | 548/559 |
| 4,556,674 | 12/1985 | Maillard et al. | 514/426 |
| 4,579,951 | 4/1986 | Pitzele et al. | 546/223 |
| 4,699,918 | 10/1987 | Maillard et al. | 514/426 |
| 4,855,444 | 8/1989 | Wambach | 548/408 |
| 4,962,204 | 10/1990 | Wambach | 548/408 |
| 5,015,633 | 5/1991 | Sudilovsky | 514/91 |
| 5,028,627 | 7/1991 | Kilbourn et al. | 514/565 |
| 5,051,444 | 9/1991 | Tamoto et al. | 514/397 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,439 | 3/1993 | Sugimoto et al. | 514/318 |
| 5,216,025 | 6/1993 | Gross et al. | 514/565 |
| 5,246,971 | 9/1993 | Williamson et al. | 514/634 |
| 5,266,594 | 11/1993 | Dawson et al. | 514/560 |
| 5,273,875 | 12/1993 | Griffith | 435/1 |
| 5,621,004 | 4/1997 | Dunn et al. | 514/551 |
| 5,629,322 | 5/1997 | Guthikonda et al. | 514/313 |

FOREIGN PATENT DOCUMENTS

| | | | |
|---|---|---|---|
| 191584 | 10/1978 | Czech Rep. | C07D 223/12 |
| 0370320 | 5/1990 | European Pat. Off. | A61K 31/49 |
| A-0446699 | 9/1991 | European Pat. Off. | C02D 5/06 |
| 0462948 | 12/1991 | European Pat. Off. | A61K 31/55 |
| 0676196 | 10/1995 | European Pat. Off. | A61K 31/085 |
| 0713704 | 5/1996 | European Pat. Off. | A61K 31/54 |
| 0713876 | 5/1996 | European Pat. Off. | C07D 487/04 |
| 0717040 | 6/1996 | European Pat. Off. | C07D 279/06 |
| 1180876 | 2/1970 | United Kingdom . | |
| 1367598 | 9/1974 | United Kingdom | C07D 27/14 |
| A-2240041 | 7/1991 | United Kingdom | A61K 31/195 |
| 91/04023 | 4/1991 | WIPO | A61K 31/195 |
| WO 91/04024 | 4/1991 | WIPO | A61K 31/195 |
| WO 93/13055 | 7/1993 | WIPO | C07E 257/114 |
| 93/16721 | 9/1993 | WIPO | A61K 37/14 |
| 93/24126 | 12/1993 | WIPO | A61K 31/395 |
| 94/12163 | 6/1994 | WIPO | A61K 31/135 |
| WO 94/12165 | 6/1994 | WIPO | A61K 31/155 |
| WO 94/14780 | 7/1994 | WIPO | C07D 239/48 |
| 94/16729 | 8/1994 | WIPO | A61K 39/395 |
| 95/05363 | 2/1995 | WIPO . | |
| 95/11231 | 4/1995 | WIPO | C07D 207/22 |
| 95/31987 | 11/1995 | WIPO | A61K 31/505 |
| 95/32203 | 11/1995 | WIPO | C07D 475/04 |
| 96/14842 | 5/1996 | WIPO | A61K 31/55 |
| 96/14844 | 5/1996 | WIPO | A61K 31/44 |
| 96/18616 | 6/1996 | WIPO . | |
| 97/16430 | 5/1997 | WIPO . | |

OTHER PUBLICATIONS

Bertolini et al., "Nitric Oxide Synthase Inhibitors: Recent Advances", *Cardiovascular & Renal Patent Update*, Ashley Publications Ltd., pp. 1339–1345, 1994.
Culvenor, C.C.J. et al, *Aust. J. Chem.*, 24 (1971) 371–375.
Caujolle, R. et al, *Eur. J. Med. Chem. Chim. Ther.*, 28(1) (1993) 29–35.
Kato et al, *Chem. Pharm. Bull.*, 20 (1972) 901.
Anderson, Wayne K. et al, *Synth. Commun.*, 19(13–14) (1989) 2237–2242.
Olomucki et al, *Biochim. Biophys. Acta*, 263 (1972) 213–216.
Otake, N. et al, *Tetrahedron Lett.*, 19 (1965) 1411–1419.
Patent: Kerin Seiyaku Kabushiki Kaisya, JP, A, 17189, 1968; *Referati vnyi Zhurnal. Khimiya.*, 1 (1970) N469P.
Umezawa et al, *J. Antibiot.*, 26 (1973) 625, 637.
Bycroft et al., *J. Antibiot.*, 22 (1969) 133–134.
Bycroft et al., *J. Chem. Soc. (C)*, (1971) 3040–3046
Marconi et al, *J. Antibiot.*, 23 (1970) 120–124.
Kretow et al, *J. Gen. Chem. USSR*, 32 (1962) 464.
Dorn et al, *Chem. Ber.*, 103 (1970) 2505–2511. .

(List continued on next page.)

*Primary Examiner*—Mukund J. Shah
*Assistant Examiner*—Pavanaram K. Sripada
*Attorney, Agent, or Firm*—Alan L. Scrivner; Dennis A. Bennett

[57] ABSTRACT

The current invention discloses azepine derivatives useful as nitric oxide synthase inhibitors.

6 Claims, No Drawings

OTHER PUBLICATIONS

Andrewes et al, *Proc. R. Soc. London B,* 133 (1946) 20, 53 (Beilstein Registry ID Only).

Schubert, H. W. et al, *Arch. Pharm. Ber. Dtsch. Pharm. Ges.,* 301(10) (1968) 750–762.

Rodricks et al, *J. Org. Chem.,* 36 (1971) 46–48.

Stefanye et al, *J. Amer. Chem. Soc.,* 77 (1955) 761–762.

Goodman et al, *J. Org. Chem.,* 23 (1958) 1954–1956.

Goodman et al, *J. Org. Chem.,* 23 (1958) 1251–1255.

Langlois et al., Synthèse de nouvelles amidines bicycliques. 1. Dérivés de l'imidazole, du triazole–1,3,4 et du tétrazole, *J. Heterocyclic Chem.,* 19(1) (1982) 193–200.

Moncada et al, *Biochem. Pharm.* 38, 1709–1715 (1989).

Moncada et al, *Pharm Rev.* 43 109–142 (1991).

S.M. Berge et al, Pharm. Salts, *J. Pharm. Sci,* 1977, 66, 1–19.

Perrin et al., "Absence of Stereoelectronic Control in Hydrolysis of Cyclic Amidines", *J. Am. Chem. Soc.,* vol. 108, No. 19, pp. 5997–6003, 1986.

Huber et al., "Saturated Heterocycles, Part 88. Synthesis of a New Ring System: Dipyrido–[1.2–a:4,3–d] pyrimidin–11–one Derivatives", *J. Chem. Soc. Perkin Trans. 1,* pp. 909–912, 1987.

Kökösi et al., "Nitrogen Bridgehead Compounds. Part 19(1). Synthesis of Polymethylenepyrimidin–4–ones", *J. Heterocyclic Chem.,* vol. 19, pp. 909–912, 1982.

Adcock et al., 2–Amino–2–imidazolines 2–Amino–2–oxazolines, Part II, pp. 474–479, 1965.

Stefanye et al., "Cyclic Guanidines from Nitrimino Compounds", *J. Am. Chem. Soc.,* vol. 77, No. 3, pp. 761–762, 1955.

Klayman et al., "2–Amino–2–thiazoline. VII. Unequivocal Structure Assignment of the Products of the Reaction of 2–Amino–2–thiazoline and Its Analogs with Carbethoxy Isothiocyanate", *J. Org. Chem.,* vol. 39, No. 13, pp. 1819–1823, 1974.

Moriconi et al., "Synthesis and Reactions of Cyclic Amidines", *J. Org. Chem.,* vol. 33, No. 5, pp. 2109–2111, 1968.

Wagenaar et al., "Methodology for the Preparation of N–Guanidino–Modified Arginines and Related Derivatives", *J. Org. Chem.,* vol. 58, No. 1, pp. 4331–4338, 1993.

Gutteridge, "Acylation of 2–Amino–5, 5–dimethyl–Δ–pyrroline 1–Oxide", *J. Chem. Soc.,* (C), pp. 3121–3125, 1971.

Langlois et al., "Synthesis and Antidepressant Properties of 2–Amino–4–phenyl–1–pyrroline Derivatives", *Eur. J. Med. Chem.,* vol. 13, No. 2, pp. 161–169, 1978 (English Summary, p. 169).

Klöer et al. "Synthesis of Substituted 2–Amino–1–pyrrolines, I." *Monatshefte für Chemie*, vol. 101, No. 5, pp. 1263–1270, 1970 (English Summary, p. 1263).

Nakane et al., "Novel Potent and Selective Inhibitors of Inducible Nitric Oxide Synthase", *Molecular Pharmacology,* vol. 47, pp. 831–834, 1995.

Dunbar et al., "Design, Synthesis, and Neurochemical Evaluation of 2–Amino–5–(alkoxycarbonyl)–3,4,5,6–tetrahydopyridines and 2–Amino–5–(alkoxycarbonyl)–1,4,5,6–tetrahydropyrimidines as $M_1$ Muscarinic Receptor Agonists", *J. Med. Chem.,* vol. 37, No. 17, pp. 2774–2782, 1994.

Klötzer et al. "Synthesis of Substituted 2–Aminopyrrolines, II." *Monatshefte für Chemie,* vol. 101, No. 6, pp. 1841–1850, 1970 (English Summary, p. 1841).

Klötzer et al. "Acylderivatives of 2–Amino–1–pyrrolines", *Monatshefte für Chemie,* vol. 102, No. 2, pp. 627–634, 1971 (English Summary, p. 627).

AZEPINE DERIVATIVES USEFUL AS NITRIC OXIDE SYNTHASE INHIBITORS

This application is a file wrapper continuation of application Ser. No. 08/425,831, filed on Apr. 20, 1995, now abandoned.

BACKGROUND OF THE INVENTION

1. Field of the Invention

The present invention relates to amidino derivative compounds, pharmaceutical compositions containing these novel compounds, and to their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacolgy*, 38, 1709–1715 (1989) and Moncada et al, *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, hyperalgesia (allodynia), cerebral ischemia (both focal ischemia, thrombotic stroke and global ischemia, secondary to cardiac arrest), and other CNS disorders mediated by NO.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In accordance with the present invention novel amidino derivative are provided. These novel inhibitor compounds can be represented by the following chemical formula (I):

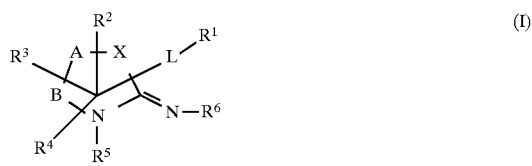

$R^1$ is selected from the group consisting of cycloalkyl, heterocyclyl, aryl, and heteroaryl which may optionally be substituted by one or more of the following lower alkyl, lower alkenyl, lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, lower alkyl, amino, alkylamino, dialkylamino, aminoalkyl, aminoacyl, carboxyl, carboalkoxy, carboaryloxy, carboalkylaryloxy, hydroxy, lower alkoxy;

L is selected from the group consisting of lower alkylene, lower alkenylene, lower alkynylene, and $-(CH_2)_m-D-(CH_2)_n-$;

D is selected from the group consisting of O, S, SO, $SO_2$, $SO_2NR^7$, $NR^7SO_2$, $NR^8$, $POOR^7$, $PON(R^7)_2$, $POOR^7NR^7$, $NR^7POOR^7$;

$R^7$ is hydrogen, lower alkyl, or aryl;

$R^8$ is hydrogen, lower alkyl, $COR^9$, or $CO_2R^9$;

$R^9$ is lower alkyl, or aryl;

m=1 to about 7;

n=0 to about 5;

wherein L may optionally be substituted by one or more of the following lower alkyl, lower alkenyl, lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: lower alkyl, amino, alkylamino, dialkylamino, aminoalkyl, aminoacyl, carboxyl, carboalkoxy, carboaryloxy, carboalkylaryloxy, hydroxy, lower alkoxy, and X is selected from the group consisting of NH, O, S, $(CH_2)_p$, and CH=CH;

p=0 to about 4;

A is selected from the group consisting of $(CH_2)_q$, CH=CH;

q=1 to about 2;

B is selected from the group consisting of $(CH_2)_v$, CH=CH;

v=1 to about 2;

$R^2$, $R^3$, and $R^4$ are independently selected from lower alkyl, lower alkenyl, lower alkynyl, hydroxy, lower alkoxy, thiol, lower thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, lower alkyl, amino, alkylamino, dialkylamino, aminoalkyl, aminoacyl, carboxyl, carboalkoxy, carboaryloxy, carboalkylaryloxy, hydroxy, lower alkoxy, and and $R^2$, $R^3$, may optionally be taken together to form an alicyclic hydrocarbon, heterocyclyl or aromatic hydrocarbon and said optionally formed ring may be optionally substituted with one or more of the following: lower alkyl, lower alkenyl, lower alkynyl which may be optionally substituted with carboxyl, carboalkoxy, carboaryloxy, carboxyalkylaryloxy and lower alkoxy; and $R^5$, $R^6$ are independently selected from the group consisting of hydrogen, hydroxy, and alkyloxy.

In another broad aspect, the present invention is directed to inhibiting nitric oxide synthesis in a subject in need of such inhibition or treatment by administering a compound of Formula (I) which preferentially inhibits the inducible isoform of nitric oxide synthase over the constitutive isoform of nitric oxide synthase, in a nitric oxide synthesis inhibiting amount to such subject.

The invention further relates to a pharmaceutical composition comprising a compound from Formula (I).

Compounds and compositions defined above have usefulness as inhibitors of nitric oxide synthase. These compounds also preferentially inhibit the inducible form Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, cerebral ischemia and other CNS disorders mediated by NO.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulfuric, citric, tartaric, phosphoric, lactic, acetic, succinic, fumaric, maleic, methanesulfonic, ethanesulfonic,p-toluenesulfonic, benzenesulfonic and the like. (See, for example, S. M. Berge et al., Pharmaceutical Salts, *J. Pharm. Sci.*, 1977, 66, 1–19.) Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intravascular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" or "cycloalkyl" means a aliphatic radical in a ring with 3 to about 10 carbon atoms, and preferably from 3 to about 6 carbon atoms. Examples of suitable alicyclic radicals include cyclopropyl, cyclobutyl, cyclopentyl, cyclohexyl, cyclohexenyl and the like.

The term "aromatic hydrocarbon radical" means 4 to about 16 carbon atoms,preferably 6 to about 12 carbon atoms, more preferably 6 to about 10 carbon atoms. Examples of suitable aromatic hydrocarbon radicals include phenyl,naphthyl, and the like.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term DCM means dichloromethane.
The term DEAD means diethyl azodicarboxylate.
The term DIBAL-H means diisobutylaluminum hydride.
The term DMAP means dimethylaminopyridine.
The term DMSO means dimethylsulfoxide.
The term EDC means 1-(3-dimethylaminopropyl)-3-ethylcarbodiimide hydrochloride.

The term "heterocyclyl radical" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, quinolinyl, and the like.

The term HOBT means N-hydroxybenzotriazole.
The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkoxy", alone or in combination, means an alkyl thioether radical wherein the term alkyl is as defined above and most preferably containing 1 to about 4 carbon atoms. Examples of suitable alkyl thioether radicals include thiomethoxy, thioethoxy, thio-n-propoxy, thio-i-propoxy, thio-n-butoxy, thio-iso-butoxy, thio-sec-butoxy, thio-tert-butoxy and the like.

The term alkoxycarbonyl as used herein means an alkoxy group, as defined above, having a carbonyl (C=O) group attached.

The term "halogen" means fluorine, chlorine, bromine or iodine.

The term mcpba means m-chloroperbenzoic acid.
The term NMM means N-methylmorpholine.
The term NMMO means 4-methylmorpholine N-oxide.
The term "prodrug" refers to a compound that is made more active in vivo.

The term sulfinyl means SO.
The term sulfonyl means $SO_2$.
The term TEA means triethylamine.
The term $TMSN_3$ means azidotrimethylsilane.

As used herein, reference to "treatment" of a patient is intended to include prophylaxis.

All references, patents or applications, U.S. or foreign, cited in the application are hereby incorporated by reference as if written herein.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Disclosed are sixteen general synthetic processes useful in the preparation of the compounds of the present invention.

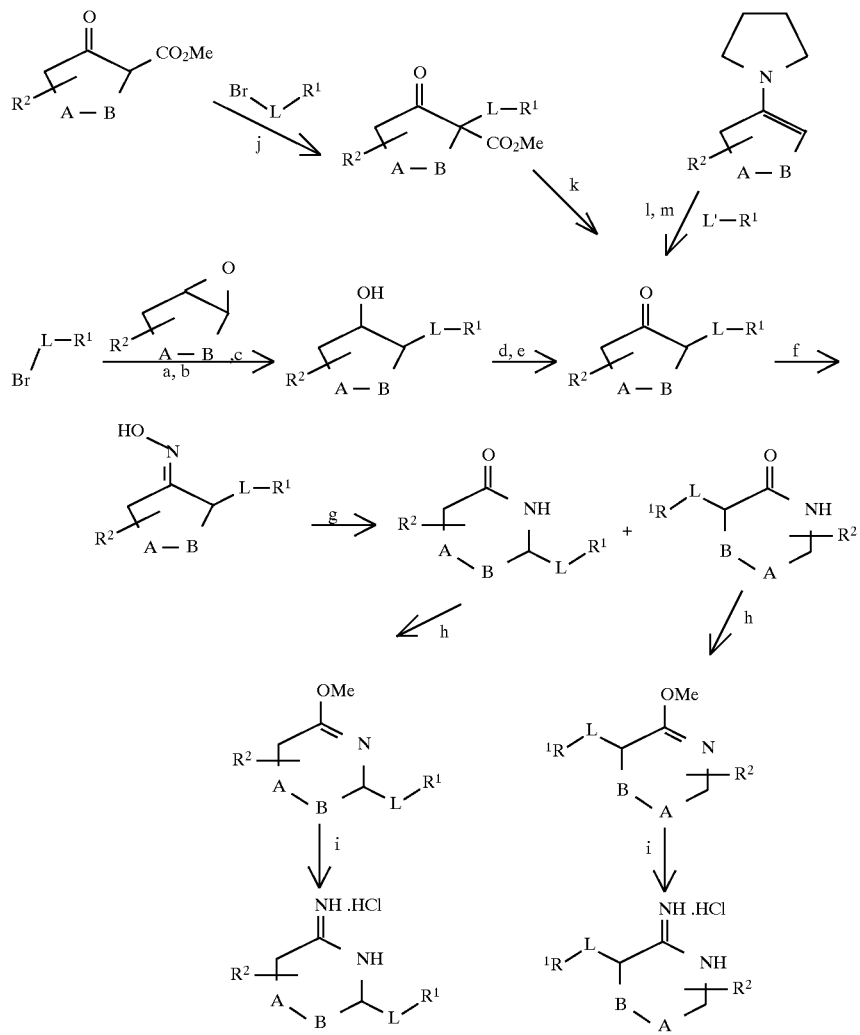

Scheme 1:

a) Mg, THF;
b) CuI, −30° C.;
c) −30° C. to 0° C. or r.t.;
d) DMSO, oxalyl chloride, $CH_2Cl_2$, −70° C.;
e) $Et_3N$, −70° C. to 0° C.;

Scheme 1:

f) NH$_2$OH, NaOAc, EtOH;
g) PhSO$_2$Cl, NaOH, H$_2$O, acetone [followed by resolution and or H$_2$, Pd/C reduction where R$^1$ = phenyl];
h) Me$_3$O$^+$ BF$_4^-$;
i) NH$_4$Cl;
j) K$_2$CO$_3$ or NaH, DMF;
k) NaCN DMSO, H$_2$O, heat;
l) DMF, L—R$^1$ (where L'—R$^1$ is CH$_2$=CHCO—R$^1$);
m) 1N LiOH, MeOH.

Scheme 2:

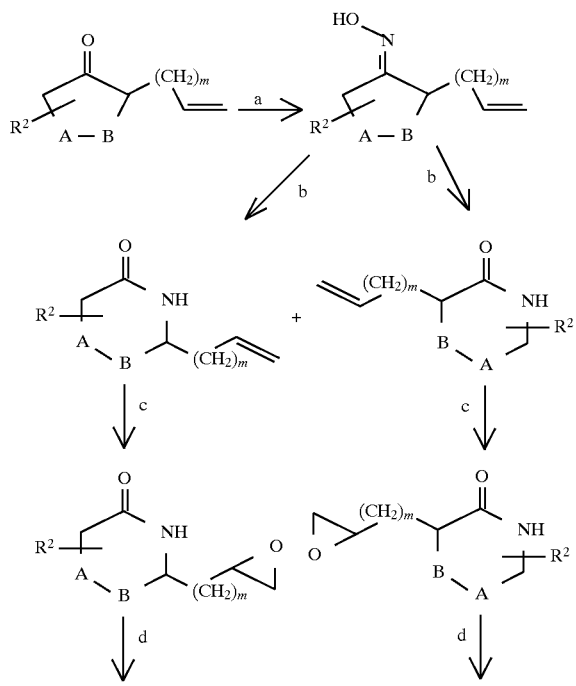

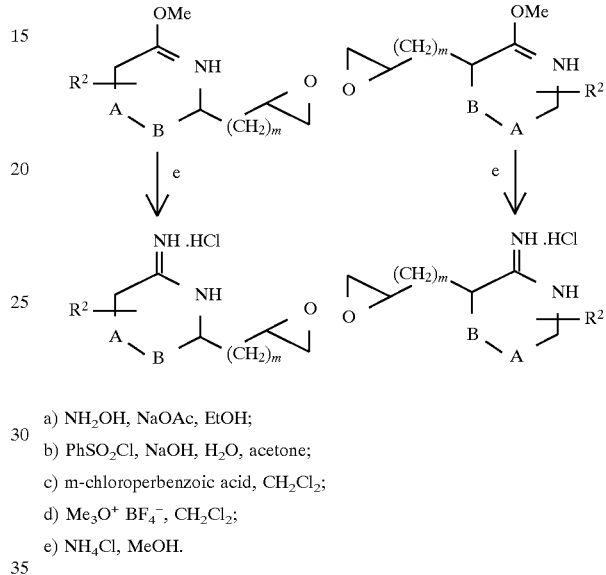

a) NH$_2$OH, NaOAc, EtOH;
b) PhSO$_2$Cl, NaOH, H$_2$O, acetone;
c) m-chloroperbenzoic acid, CH$_2$Cl$_2$;
d) Me$_3$O$^+$ BF$_4^-$, CH$_2$Cl$_2$;
e) NH$_4$Cl, MeOH.

Scheme 3:

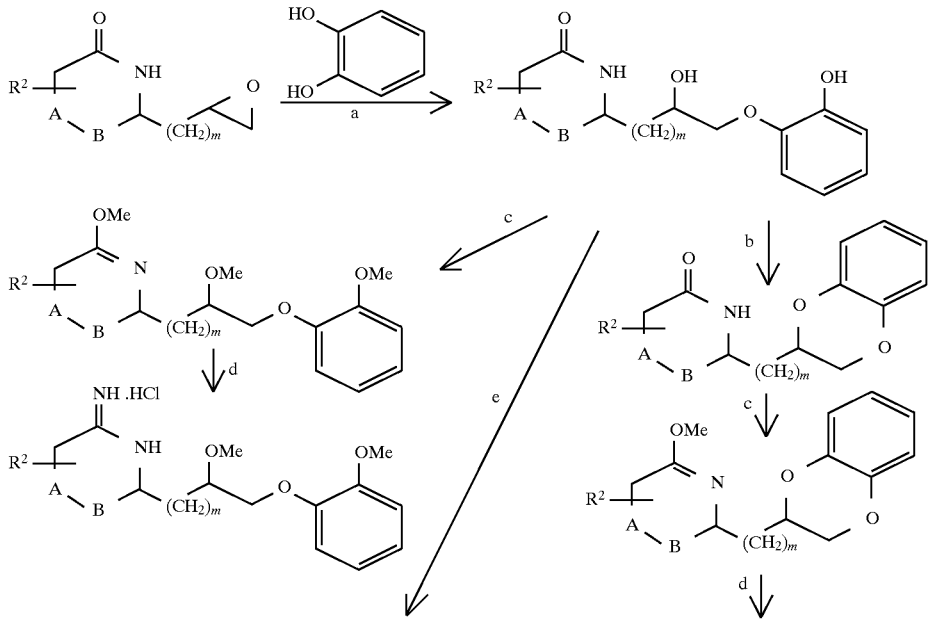

Scheme 3:
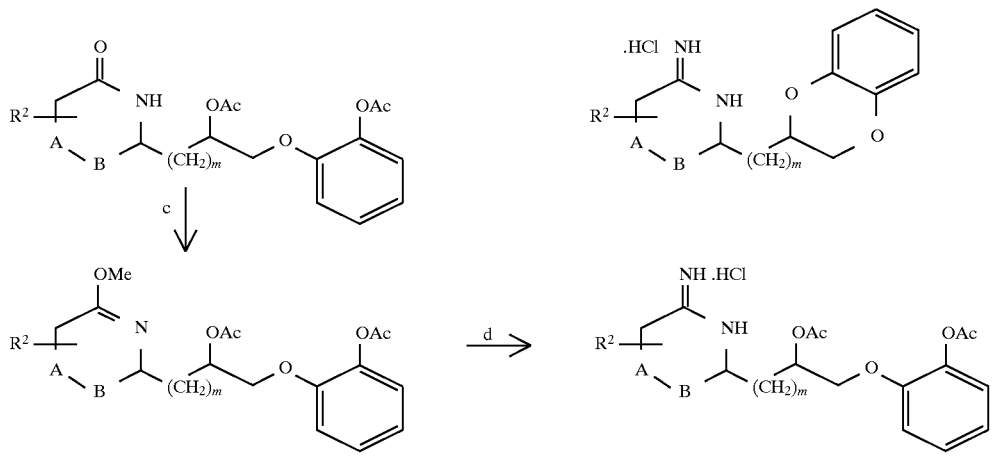
a) NaH, DMF;
b) Ph$_3$P, diethylazodicarboxylate (DEAD), THF;
c) Me$_3$O$^+$ BF$_4^-$, CH$_2$Cl$_2$;
d) NH$_4$Cl, MeOH;
e) acetic anhydride, pyridine.
Scheme 4:
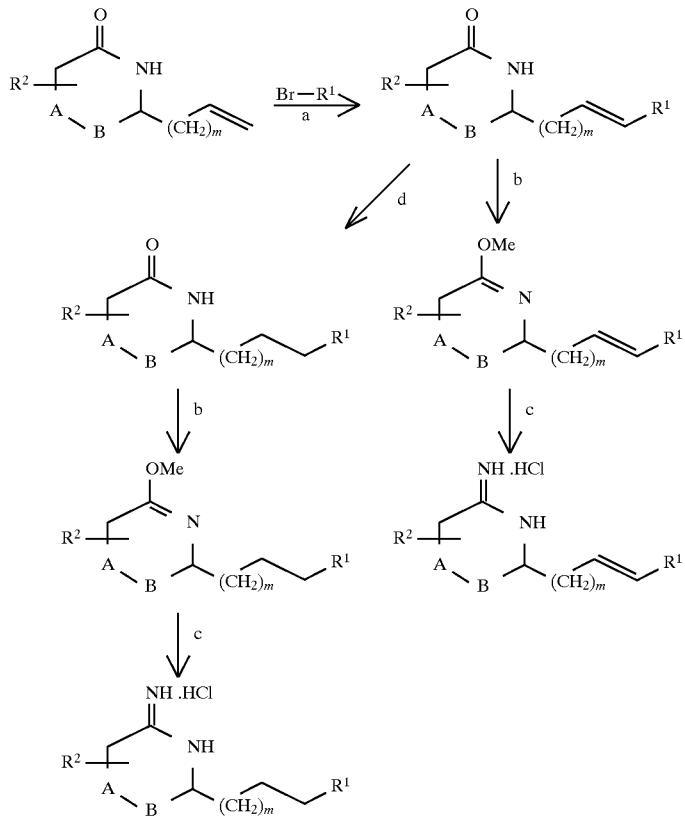
a) Pd(OAc)$_2$, tri-o-tolylphosphine, Et$_3$N, MeCN,
where R$^1$ = substituted or unsubstituted aromatic or heteroaromatic;
b) Me$_3$O$^+$ BF$_4^-$, CH$_2$Cl$_2$;
c) NH$_4$Cl, MeOH;
d) H$_2$, Pd/C.

Scheme 5:
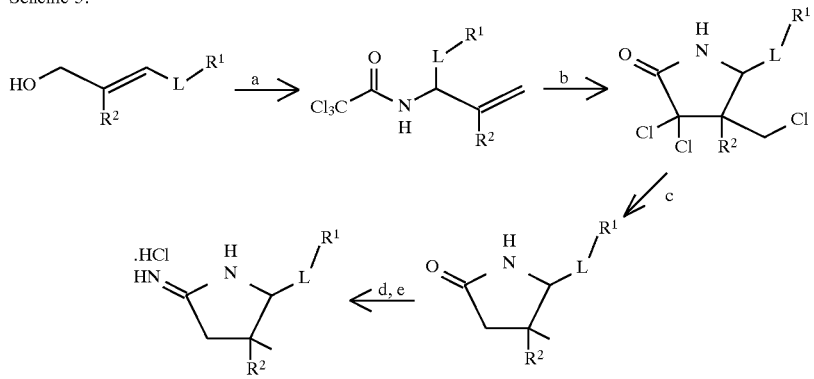
a) Cl₃CN, NaH, xylene, D;
b) Ru catalyst;
c) Bu₃SNH;
d) Me₃O⁺ BF₄⁻, CH₂Cl₂;
e) NH₄Cl, MeOH.
Scheme 6:
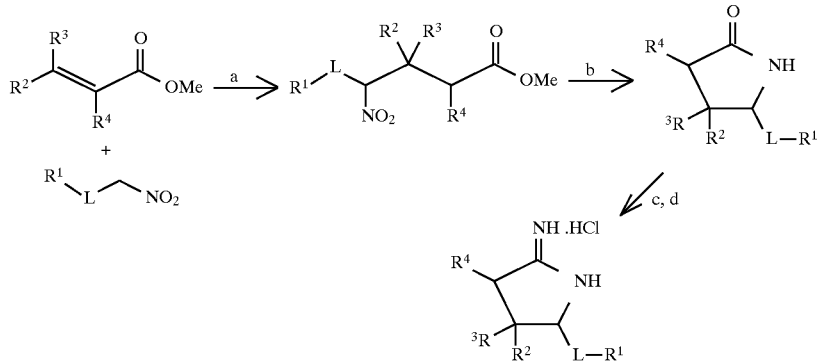
a) Base;
b) H₂/RaNi, 55° C.;
c) Me₃O⁺ BF₄⁻, CH₂Cl₂;
d) NH₄Cl, MeOH
Scheme 7:
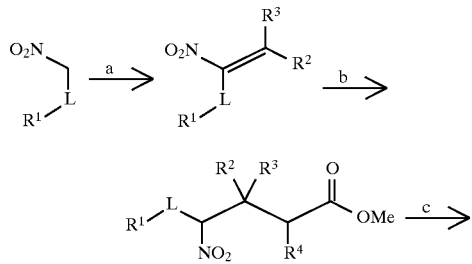
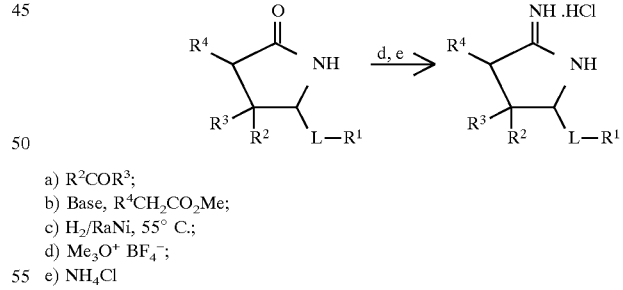
-continued
Scheme 7:
a) R²COR³;
b) Base, R⁴CH₂CO₂Me;
c) H₂/RaNi, 55° C.;
d) Me₃O⁺ BF₄⁻;
e) NH₄Cl Scheme 8:
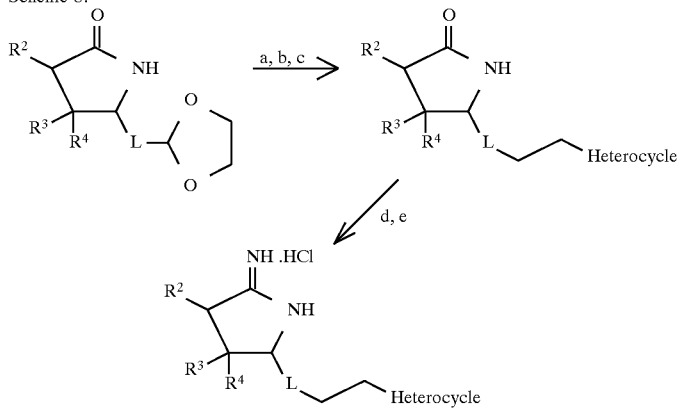
a) HCl;
b) Zn/BrCH$_2$Heterocycle;
c) Et$_3$SiH;
d) Me$_3$O$^+$ BF$_4^-$;
e) NH$_4$Cl, MeOH
Scheme 9:
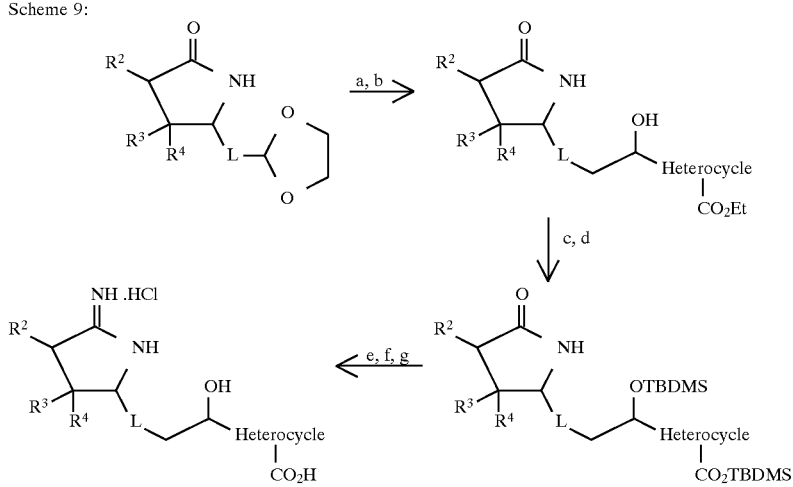
a) HCl;
b) Zn/BrCH$_2$Heterocycle-CO$_2$Et;
c) NaOH, MeOH;
d) t-butyldimethylsilyl chloride (TBDMSCl);
e) Me$_3$O$^+$BF$_4^-$, CH$_2$Cl$_2$;
f) NH$_4$Cl, MeOH;
f) HCl.
Scheme 10:
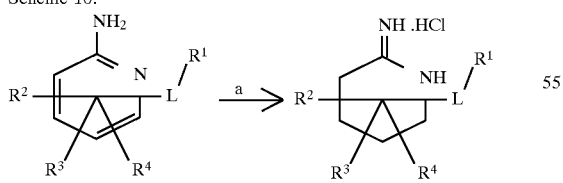
Scheme 10:
a) H$_2$, Rh/C, HOAc or H$_2$, PtO$_2$/C, HOAc Scheme 11:
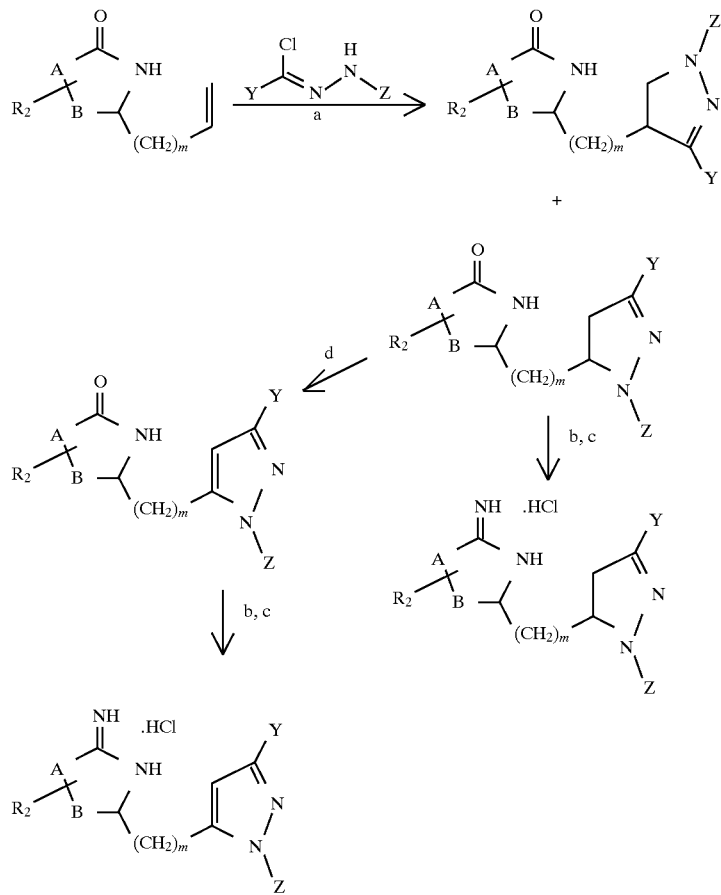
Y = Aryl, CF₃, alkoxycarbonyl
Z = 5-membered ring heterocycle (containing 1–4 N, and/or O, and/or S),
phenyl or pyridyl substituted with 1–3 groups defined such as: $CO_2H$,
alkoxycarbonyl, $SO_2NH_2$, $SO_3H$, alkylsulfonamides, and nitro.
a) $Et_3N$, toluene; b) $Me_3O^+BF_4^-$, $CH_2Cl_2$; c) $NH_4Cl$, $CH_3OH$;
d) DDQ, Benzene.
Scheme 12:
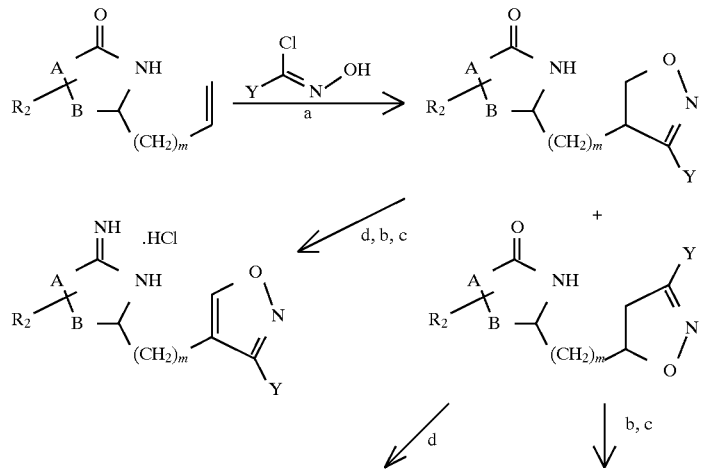

-continued

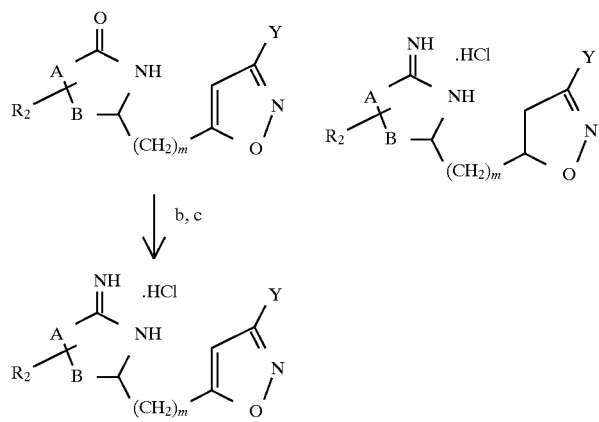

Y = Aryl, CF₃, alkoxycarbonyl a) Et₃N, diethyl ether (or toluene); b) Me₃O⁺BF₄⁻, CH₂Cl₂;
c) NH₄Cl, CH₃OH; d) MnO₂, Benzene/dioxane.

Scheme 13:

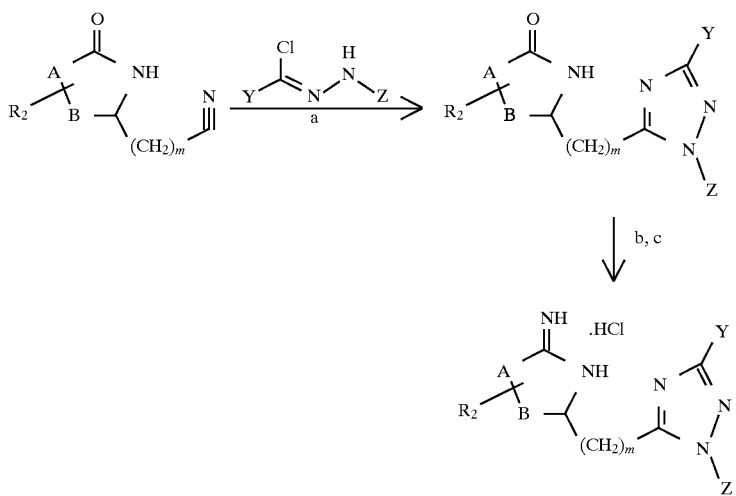

Y = Aryl, CF₃, alkoxycarbonyl
Z = 5-membered ring heterocycle (containing 1–4 N, and/or O, and/or S),
phenyl or pyridyl substituted with 1–3 groups defined such as: CO₂H, alkoxycarbonyl, SO₂NH₂, SO₃H, alkylsulfonamides, nitro.

a) Et₃N, toluene; b) Me₃O⁺BF₄⁻, CH₂Cl₂; c) NH₄Cl, CH₃OH.

Scheme 14:

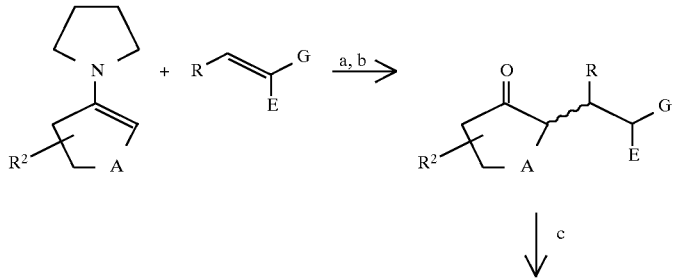

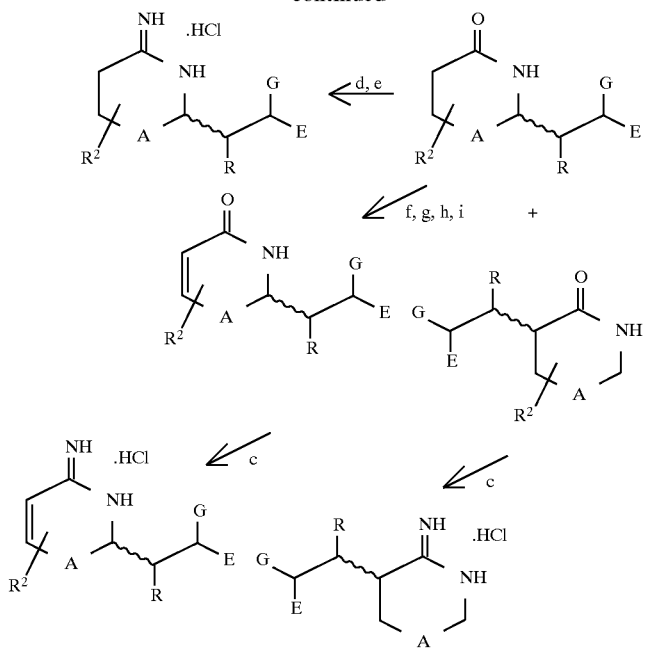

R = Hydrogen, amino, alkyl, alkenyl, alkynyl, carboxyl, ester, phenyl, halogen, alkoxy, heterocyclic, carbocyclic radicals wherein all said radicals may optionally substituted;
E = Cyano, carboxyl, ester, nitro, heterocyclic;
G = Hydrogen, alkyl, haloalkyl, carboxyalkyl, carboxyl, ester;
R and G can form a carbocyclic ring containing 4–7 carbon atoms.

a) DMF, reflux, 24 h; add $H_2O$, reflux, 1h; b) N LiOH/$CH_3OH$; c) $H_2N-O-SO_3H$, $HCO_2H$, reflux, 3h; d) $Me_3O^+BF_4^-$, $CH_2Cl_2$; e) $NH_4Cl$, $CH_3OH$; f) (t-butylOCO)$_2$O, DMAP, THF; g) Li hexamethyldisilazide, THF, PhSeCl; h) 30% $H_2O_2$, THF; i) 4N HCl, HOAc.

Scheme 15:

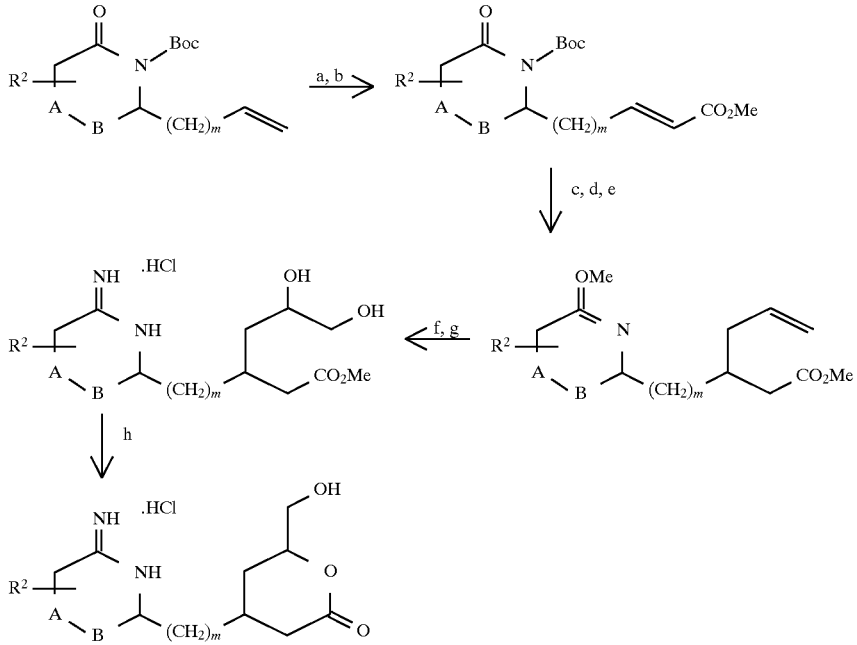

a) O$_3$/Ph$_3$P; b) Ph$_3$P=CH—CO$_2$CH$_3$; c) (allyl)$_2$CuLi
d) CF$_3$CO$_2$H; e) Et$_3$O$^+$BF$_4^-$, CH$_2$Cl$_2$; f) OsO$_4$, NMO;
g) NH$_4$Cl, MeOH; h) dilute acid, warm

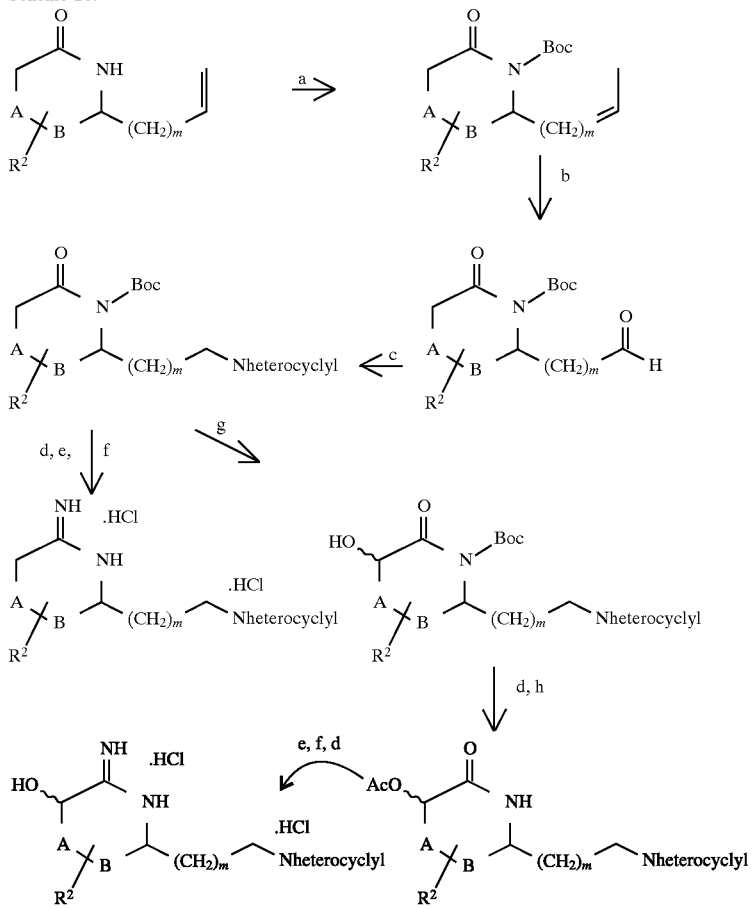

Scheme 16:

a) di-t-butyl dicarbonate, DMAP, THF; b) O$_3$; c)
HNheterocyclyl = heterocyclyl containing NH as part
of ring, H$_2$, Pd catalyst; d) HCl, MeOH; e) Et$_3$O$^+$
BF$_4^-$, CH$_2$Cl$_2$; f) NH$_4$Cl, MeOH; g) organo Li base,
TMS$_2$O$_2$; h) Ac$_2$O, pyridine Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous Na$_2$SO$_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2N in MeOH, or 6N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometer with tetramethylsilane as an internal standard. $^{13}$C NMR were obtained from a Varian spectrometer at 125.8 MHz with tetramethylsilane as an internal standard.

EXAMPLE 1

2-(phenylmethyl)cyclohexanone, oxime

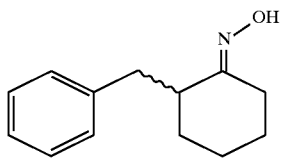

A sample of 2-benzylcyclohexanone (Aldrich, 9.3 g, 49.7 mmol) was combined with hydroxylamine hydrochloride ($NH_2OH$ HCl, 4.8 g, 69.6 mmol) and sodium acetate (NaOAc, 7.3 g, 89.5 mmol) in a mixture of ethanol (EtOH, 90 mL) and water (90 mL). This mixture was refluxed for 15 h under a nitrogen atmosphere. After the reaction was cooled to room temperature, all solvent was removed under reduced pressure. The residue was partitioned between ethyl acetate (EtOAc) and water and the organic phase was washed with 1×75 mL of saturated NaCl (brine), dried over $Na_2SO_4$, and stripped of all solvent under reduced pressure. This provided 9.7 g (97%) of the title compound as a cream colored solid. This material showed a retention time of 17.3 min (100% purity by peak area integration) on a Shimadzu GC-14A gas chromatograph (GC) with a 0.25 mm×25M methyl, 5% phenylsilicone column. Under identical conditions, the starting ketone had a retention time of 14.9 min. The NMR and IR spectra of the product were consistent with the assigned structure.

EXAMPLE 2 hexahydro-7-(phenylmethyl)-1H-azepin-2-one, mixture with hexahydro-3-(phenylmethyl)-1H-azepin-2-one

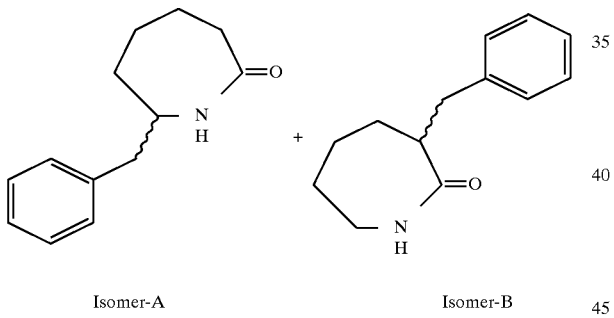

Isomer-A                    Isomer-B

A 2.7 g (13.5 mmol) sample of the title material of Example 1 was added to a dropping funnel containing 2.4 mL of 80% $H_2SO_4$. After using a stirring rod to obtain a turbid solution, this mixture was added dropwise (30 min) to 1 mL of 80% $H_2SO_4$ stirred magnetically and maintained at 120° C. with an external oil bath. Within 5 minutes of the start of addition an exotherm was noted and the temperature of the reaction rose to 150° C. before cooling again to 120° C. Ten minutes after the addition was complete, the flask was removed from the bath and allowed to cool to room temperature. The product mixture was diluted with water (20 mL) and brought to pH 6 with concentrated $NH_4OH$. This solution was further diluted with 75 mL of water and extracted with 2×35 mL of $CH_2Cl_2$. The combined organic phase was washed with 1×35 mL of brine, dried ($Na_2SO_4$), filtered, and stripped of all solvent under reduced pressure. The crude solid (980 mg, 36%) was separated into its title Isomer-A and Isomer-B components by column chromatography. Under conditions identical to that described in Example 1, the Isomer-A and Isomer-B components had GC retention times of 20.7 and 17.2 minutes respectively. The NMR and IR spectra of the products were consistent with their assigned structures.

The Isomer-A material (1.1 g) was chromatographed on a Chiralpak AD column eluting with 3% isopropanol (IPA)/hexane to yield 275 mg (50%) of the (+)Isomer-A enantiomer and 254 mg (46%) of the (−)Isomer-A enantiomer. The NMR and IR spectrum of these two compounds were identical in all respects to that of racemic Isomer-A.

(+)Isomer-A enantiomer: $[a]_D$ (1.0, $CHCl_3$)=+16.4±3.9
Elemental analysis: $C_{13}H_{17}NO$ (MW=203.28)

|  | C | H | N |
|---|---|---|---|
| Calculated: | 76.81 | 8.43 | 6.89 |
| Found: | 76.55 | 8.69 | 6.63 |

(−)Isomer-A enantiomer: $[a]_D$ (1.0, $CHCl_3$)=−13.5±2.7
Elemental analysis: $C_{13}H_{17}NO$ (MW=203.28)

|  | C | H | N |
|---|---|---|---|
| Calculated: | 76.81 | 8.43 | 6.89 |
| Found: | 76.53 | 8.50 | 6.61 |

EXAMPLE 3

4,5,6,7-tetrahydro-2-methoxy-7-(phenylmethyl)-3H-azepine

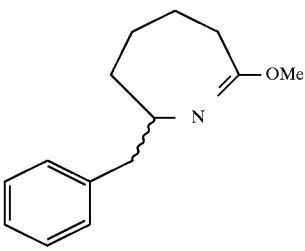

To a magnetically stirred slurry of trimethyloxonium tetrafluoroborate (Lancaster, 0.30 g, 2.0 mmol) and 3A molecular sieves (2 g) in $CH_2Cl_2$ (15 mL) under argon (Ar) was added the Isomer-A product of Example 2 (0.31 g, 1.5 mmol). This mixture was stirred at room temperature for 3 days before it was diluted with 10 mL of $CH_2Cl_2$ and partitioned between 40 mL of saturated $KHCO_3$ and 50 mL of EtOAc. The organic phase was separated, dried over $Na_2SO_4$, filtered, and stripped of all solvent under reduced pressure to provide the crude title product as a pale yellow oil. This material was chromatographed on Merck silica gel using conditions described by W. T. Still *J. Org. Chem.* 1978, 43, 2923–2925 eluting with EtOAc/n-hexane (1:1). The title pale yellow liquid product (308 mg, 93%) had a GC retention time of 15.5 min (100%) under the conditions of Example 1 and NMR and IR spectra consistent with the indicated product.

EXAMPLE 4

4,5,6,7-tetrahydro-2-methoxy-3-(phenylmethyl)-3H-azepine

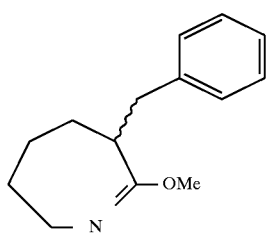

The Isomer-B product of Example 2 is reacted with trimethyloxonium tetrafluoroborate by the method of Example 3 to produce the title material.

EXAMPLE 5 hexahydro-7-(phenylmethyl)-1H-azepin-2-imine, monohydrochloride

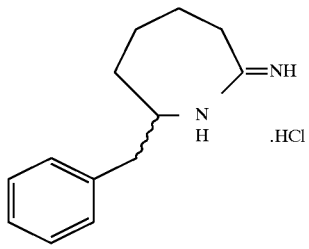

The title product of Example 3 (0.30 g, 1.4 mmol) and 0.06 g (1.1 mmol) of ammonium chloride (NH$_4$Cl) were refluxed in 13 mL of methanol (MeOH) under a nitrogen atmosphere for 19 h. After cooling the reaction to room temperature, it was filtered, stripped of all solvent under reduced pressure, and partitioned between 15 mL of water and 7 mL of CH$_2$Cl$_2$. The organic and aqueous phases were separated and the aqueous phase was washed with a 25 mL portion of EtOAc before it was lyophilized to provide 0.24 g (92%) of the white solid title material.

HRMS (EI) calcd for C$_{13}$H$_{18}$N$_2$ m/e 202.147, found m/e 202.147. $^1$H NMR(CD$_3$OD): d 7.20–7.35 (m, 5H), 3.96 (m, 1H), 2.99 (dd, 1H, J=14.8 Hz), 2.89 (dd, 1H, J=14.8 Hz), 2.82 (m, 1H), 2.64 (m, 1H) 2.05–1.86 (m, 3H), 1.71–1.36 (m, 3H). Elemental analysis: C$_{13}$H$_{18}$N$_2$.HCl.0.15 H$_2$O (MW=241.46)

|  | C | H | N | Cl |
|---|---|---|---|---|
| Calculated: | 64.67 | 8.06 | 11.60 | 14.68 |
| Found: | 64.86 | 8.45 | 11.54 | 14.60 |

EXAMPLE 6 hexahydro-3-(phenylmethyl)-1H-azepin-2-imine, monohydrochloride

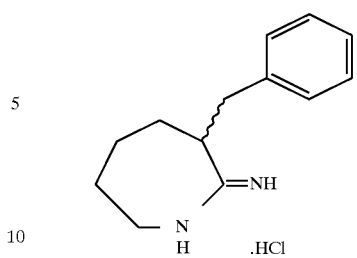

The title product of Example 4 in MeOH is reacted with ammonium chloride by the method of Example 5 to generate the title material.

EXAMPLE 7
7-(cyclohexylmethyl)hexahydro-1H-azepin-2-one

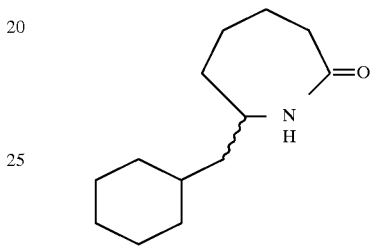

The Isomer-A title product of Example 2 (0.80 g, 3.9 mmol) dissolved in MeOH was placed in a standard Parr hydrogenation shaker flask along with 5% Rh/C. The reaction mixture was shaken under an H$_2$ pressure of 60 psi at 60° C. for 22 hr. All solvent was then removed under reduced pressure. The residue was then dissolved in CH$_2$Cl$_2$ and this solution was filtered and stripped of all solvent to yield 875 mg of the title material. The colorless semi-solid title product had a GC retention time of 15.5 min (100%) under the conditions of Example 1 and NMR and IR spectra consistent with the title product.

EXAMPLE 8
2-(cyclohexylmethyl)-3,4,5,6-tetrahydro-7-methoxy-2H-azepine

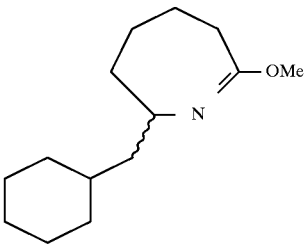

The title product of Example 7 (0.87 g, 4.2 mmol) was reacted with trimethyloxonium tetrafluoroborate (0.80 g, 5.4 mmol) by the method of Example 3 to yield 0.76 g (82%) of the title material. The pale yellow oil title product had a GC retention time of 14.9 min (100%) under the conditions of Example 1 and NMR and IR spectra consistent with the title product.

EXAMPLE 9
7-(cyclohexylmethyl)hexahydro-1H-azepin-2-imine, monohydrochloride

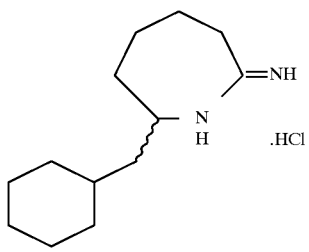

The product of Example 8 (0.76 g, 3.4 mmol) in 20 mL of MeOH was reacted with ammonium chloride (144 mg, 2.7 mmol) by the method of Example 5 to yield 258 mg (30.4%) of the title material.

HRMS (EI) calcd for $C_{13}H_{24}N_2$ m/e 208.194, found m/e 208.195. $^1$H NMR(CD$_3$CD): d 3.70 (m, 1H), 2.82 (m, 1H), 2.61 (m, 1H), 2.06–1.93 (m, 2H), 1.86–1.62 (m, 7H), 1.62–1.13 (m, 8H). Elemental analysis: $C_{13}H_{24}N_2$.HCl.0.33 H$_2$O (MW=250.81)

|  | C | H | N | Cl |
|---|---|---|---|---|
| Calculated: | 62.27 | 10.31 | 11.17 | 14.14 |
| Found: | 62.23 | 10.09 | 10.83 | 13.52 |

EXAMPLE 10
3-(cyclohexylmethyl)hexahydro-1H-azepin-2-one, monohydrochloride

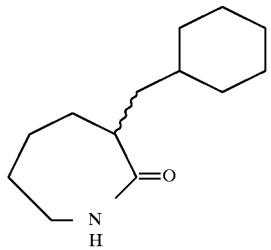

The Isomer-B title product of Example 2 is converted to the title material by the method of Example 7.

EXAMPLE 11
6-(cyclohexylmethyl)-3,4,5,6-tetrahydro-7-methoxy-2H-azepine

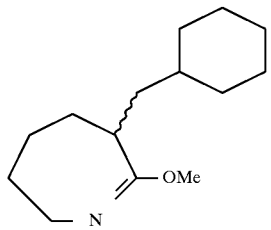

The product of Example 10 is reacted with trimethyloxonium tetrafluoroborate by the method of Example 3 to produce the title material.

EXAMPLE 12
3-(cyclohexylmethyl)hexahydro-1H-azepin-2-imine, monohydrochloride

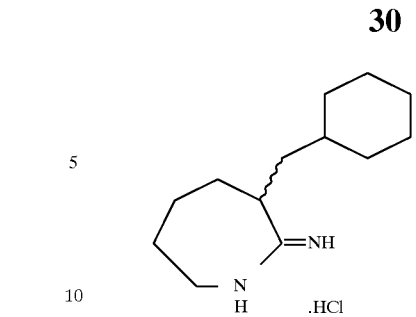

The title product of Example 11 in MeOH is reacted with ammonium chloride by the method of Example 5 to generate the title material.

EXAMPLE 13
(+)-3,4,5,6-tetrahydro-7-methoxy-2-(phenylmethyl)-2H-azepine

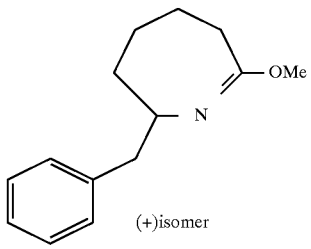

The (+)Isomer-A enantiomer product of Example 2 (0.24 g, 1.2 mmol) was reacted with trimethyloxonium tetrafluoroborate (0.23 g, 1.6 mmol) by the method of Example 3 to yield 0.25 g (95%) of the title material. The pale yellow oil title product had a GC retention time of 15.4 min (100%) under the conditions of Example 1 and NMR and IR spectra were identical to the title products of Examples 3 and 15.

EXAMPLE 14
(+)-hexahydro-7-(phenylmethyl)-1H-azepin-2-imine, monohydrochloride

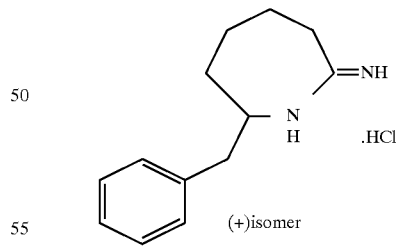

The product of Example 13 (0.25 g, 1.1 mmol) in 19 mL of MeOH was reacted with ammonium chloride (50 mg, 0.93 mmol) by the method of Example 5 to yield 200 mg (88%) of the title material. The NMR and IR spectra of the title compound were identical to that of the title products of Examples 5 and 16.

HRMS (El) calcd for $C_{13}H_{18}N_2$ m/e 202.147, found m/e 202.147. $[a]_D$ (0.095, CHCl$_3$)=+35.6±2.8 Elemental analysis: $C_{13}H_{24}N_2$.0.95 HCl.0.45 H$_2$O (MW=245.04)

|  | C | H | N | Cl |
|---|---|---|---|---|
| Calculated: | 63.72 | 8.17 | 11.43 | 13.74 |
| Found: | 64.05 | 8.70 | 11.15 | 13.91 |

EXAMPLE 15

(−)-3,4,5,6-tetrahydro-7-methoxy-2-(phenylmethyl)-2H-azepine

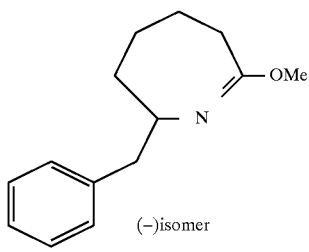

(−)isomer

The (−)Isomer-A enantiomer product of Example 2 (0.23 g, 1.1 mmol) was reacted with trimethyloxonium tetrafluoroborate (0.21 g, 1.4 mmol) by the method of Example 3 to yield 0.21 g (88%) of the title material. The pale yellow oil title product had a GC retention time of 15.4 min (100%) under the conditions of Example 1 and NMR and IR spectra were identical to the title products of Examples 3 and 13.

EXAMPLE 16

(−)-hexahydro-7-(phenylmethyl)-1H-azepin-2-imine, monohydrochloride

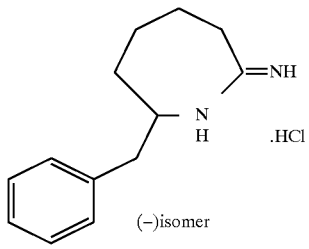

(−)isomer

The product of Example 15 (0.21 g, 1.0 mmol) in 18 mL of MeOH was reacted with ammonium chloride (43 mg, 0.80 mmol) by the method of Example 5 to yield 173 mg (89%) of the title material. The NMR and IR spectra of the title compound were identical to that of the title products of Examples 5 and 14.

HRMS (EI) calcd for $C_{13}H_{18}N_2$ m/e 202.147, found m/e 202.147. $[a]_D$ (0.149, $CHCl_3$)=−35.6±2.8 Elemental analysis: $C_{13}H_{24}N_2 \cdot HCl \cdot 0.2 \ H_2O$ (MW=242.36)

|  | C | H | N | Cl |
|---|---|---|---|---|
| Calculated: | 64.43 | 8.07 | 11.56 | 14.63 |
| Found: | 64.43 | 8.31 | 11.15 | 14.88 |

EXAMPLE 17

2-(2-propenyl)cyclohexanone, oxime

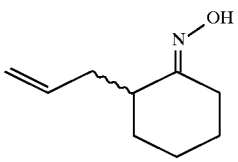

A sample of 2-allylcyclohexanone (Frinton, 2.0 g, 14.5 mmol) was converted to the title compound by the method of Example 1 using 1.5 g (21.7 mmol) of hydroxylamine hydrochloride and 2.0 g (24.6 mmol) of NaOAc in a mixture of 25 mL of EtOH and 25 mL of water. The procedure produced 2.6 g of the crude title compound.

EXAMPLE 18 hexahydro-3-(2-propenyl)-1H-azepin-2-one, mixture with hexahydro-7-(2-propenyl)-1H-azepin-2-one

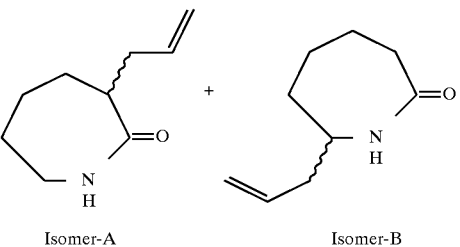

Isomer-A                Isomer-B

The title product of Example 17 (2.0 g, 13.0 mmol) in 15 mL of acetone containing 1N NaOH (14.3 mL, 52.4 mmol) was reacted with benzene sulfonylchloride (2.3 g, 13.1 mmol) by the method described in Example 67. The crude reaction mixture was separated into its Isomer-A and Isomer-B components by silica gel chromatography.

EXAMPLE 19 hexahydro-7-[(oxiran-2-yl)methyl]-1H-azepin-2-one

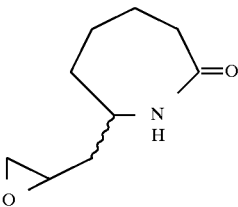

The title product isomer B of Example 18 (2.99 g, 19.5 mmol) in 150 mL of $CH_2Cl_2$ was refluxed with m-chloroperbenzoic acid (MCPBA, 5.05 g, 29.3 mmol) for 3 hr. After stirring at room temperature overnight, an additional 1.0 g (5.8 mmol) of MCPBA was added and the reaction reheated to reflux for an additional 6 hr. The solvent was removed and the residue was dissolved in EtOAc (150 mL). After this solution was washed 3×50 mL of saturated $NaHCO_3$ and dried ($Na_2SO_4$), all solvent was removed to provided the crude desired product. Purification via flash column chromatography using 100% EtOAc and deactivated silica gel yielded 2.25 g (68%) of the title compound.

EXAMPLE 20

3,4,5,6-tetrahydro-7-methoxy-2-[(oxiran-2-yl)methyl]-2H-azepine

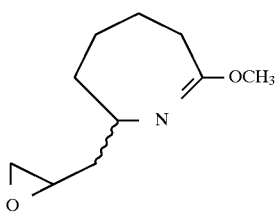

The product of Example 19 (2.0 g, 13 mmol) was reacted with trimethyloxonium tetrafluoroborate (2.49 g, 16.8 mmol) in CH₂Cl₂ (80 mL) by the method of Example 3 to produce 1.8 g (83%) of the title material following chromatography.

EXAMPLE 21
hexahydro-7-[(oxiran-2-yl)methyl]-1H-azepin-2-imine, monohydrochloride

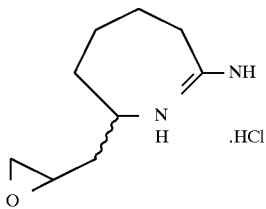

The product of Example 20 in MeOH was reacted with ammonium chloride by the method of Example 5 to yield the title material.

EXAMPLE 22
hexahydro-7-[(2-hydroxy-3-(2-hydroxyphenoxy)propyl]-1H-azepin-2-one

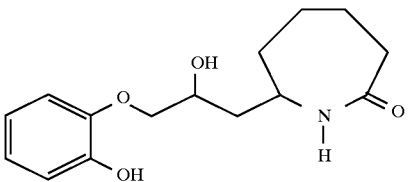

Sodium hydride (52.4% in mineral oil, 66.5 mmol, 3.05 g) is washed with hexane in a 500 mL flask. The hexane-mineral oil is decanted, and DMF (35 mL) is added. A dropping funnel is fitted onto the flask, with nitrogen flow maintained through the reaction system. 1,2-Dihydroxybenzene (63.6 mmol, 7.0 g) dissolved in DMF (150 mL) is added CAREFULLY dropwise to the stirring mixture. When the addition is complete, the mixture is allowed to stir at room temperature for one hour. The title compound of Example 19 (58 mmol) is dissolved in DMF (100 mL) and added quickly to the reaction mixture. The stirring mixture is immersed in a 75° C. oil bath, and allowed to react for 24 h. The mixture is removed from the oil bath, allowed to come to room temperature, and poured into 150 mL 0.5M KHSO₄ solution. This mixture is diluted with water to 500 mL, and extracted thrice with 150 mL portions of CH₂Cl₂. The organic fractions are combined, dried (MgSO₄), filtered, and stripped at reduced pressure. The residue is purified by silica column chromatography to give the title compound.

EXAMPLE 23
7-[(1,4-benzodioxan-2-yl)methyl]hexahydro-1H-azepin-2-one

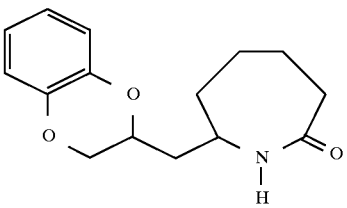

A 1000 mL three-necked round bottom flask fitted with a magnetic stirrer, thermometer, dropping funnel, and Y-tube (nitrogen inlet, drying tube outlet) is charged with the title compound from Example 22 (21.6 mmol), triphenylphosphine (5.67 g, 21.6 mmol), and THF (300 mL). The temperature is reduced to 2° C. (ice bath), and diethyl azodicarboxylate (DEAD, 3.77 g, 3.4 mL, 21.6 mmol) in 50 mL THF is added dropwise, keeping the reaction temperature at or below 4° C. After the addition is completed, the reaction is stirred a further 45 min in the ice bath; the cold bath is removed and the mixture is allowed to stir at room temperature overnight. The reaction mixture is then stripped in vacuo to a residue which is applied to a silica gel column for purification with hexane/ethyl acetate eluents giving the title compound.

EXAMPLE 24
2-[(1,4-benzodioxan-2-yl)methyl]-3,4,5,6-tetrahydro-7-methoxy-2H-azepine

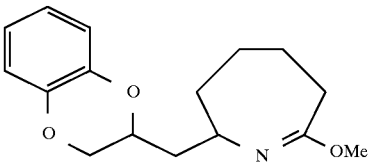

The title compound of Example 23 is treated by the method described in Example 3 to yield the present title compound.

EXAMPLE 25
7-[(1,4-benzodioxan-2-yl)methyl]hexahydro-1H-azepin-2-imine, monohydrochloride

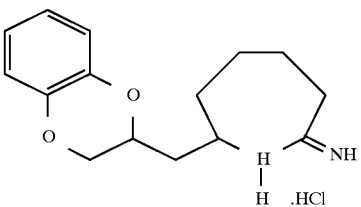

The title compound of Example 24 is treated by the method described in Example 5 to yield the present title compound.

EXAMPLE 26
3,4,5,6-tetrahydro-7-methoxy-2-[2-methoxy-3-(2-methoxyphenoxy)propyl]-2H-azepine

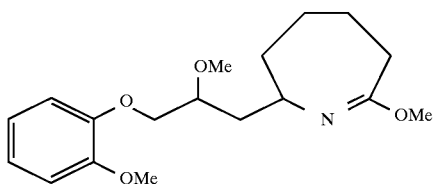

The title compound of Example 22 is treated by the method described in Example 3 to yield the present title compound.

EXAMPLE 27 hexahydro-7-[2-methoxy-3-(2-methoxyphenoxy)propyl]-1H-azepin-2-imine, monohydrochloride

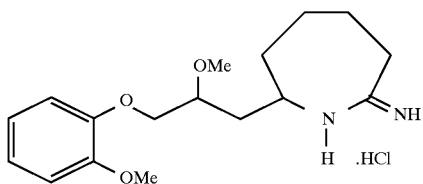

The title compound of Example 26 is treated by the method described in Example 5 to yield the present title compound.

EXAMPLE 28

7-[2-acetyloxy-3-(2-acetyloxyphenoxy)propyl]hexahydro-1H-azepin-2-one

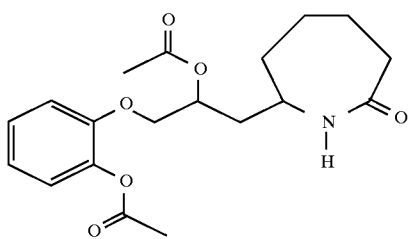

The title compound of Example 22 (20 mmol) is dissolved in 100 mL $CH_2Cl_2$ and cooled to −5° C. (ice-methanol bath). The solution is protected from moisture and 10 mL dry pyridine is added. A solution of 50 mmol acetic anhydride in 20 mL $CH_2Cl_2$ is slowly added, keeping the reaction temperature at or below 0° C. The mixture is allowed to stir an additional 2 hr, and is then stripped in vacuo to a residue. This residue is partitioned between 0.1M $KHSO_4$ and ether. The aqueous phase is washed with ether, the organic phases are combined, dried ($MgSO_4$), filtered and stripped in vacuo to give the title compound.

EXAMPLE 29 a-[(2-acetyloxyphenoxy)methyl]-3,4,5,6-tetrahydro-7-methoxy-2H-azepine-2-ethanol acetate (ester)

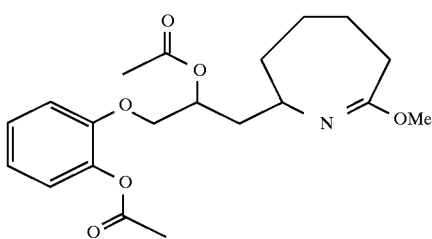

The title compound of Example 28 is treated by the method described in Example 3 to yield the present title compound.

EXAMPLE 30 hexahydro-a-[(2-hydroxyphenoxy)methyl]-7-imino-1H-azepine-2-ethanol, monohydrochloride

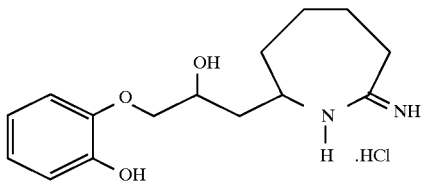

The title compound of Example 29 is treated by the method described in Example 5 to yield the partially acetylated present title compound. The acetyl groups are removed with refluxing (1 hr) 0.5N HCl, followed by in vacuo concentration to one third volume. The resulting aqueous solution is lyophilized to give title compound.

EXAMPLE 31 a-[(2-acetyloxyphenoxy)methyl]hexahydro-7-imino-1H-azepine-2-ethanol acetate(ester), monohydrochloride

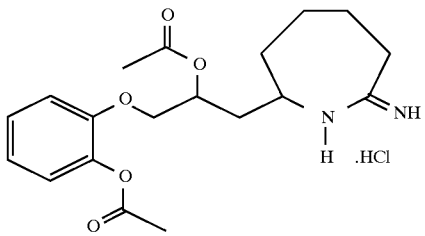

The dried title compound of Example 30 is treated with a three-fold excess of acetyl chloride in $CH_2Cl_2$, followed by stripping in vacuo. The resulting residue is dissolved in water and lyophilized to give the title compound.

EXAMPLE 32 hexahydro-7-(3-phenyl-2-propenyl)-1H-azepin-2-one

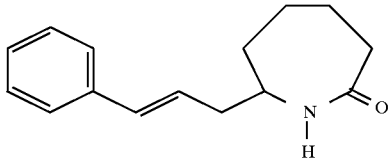

A mixture of palladium acetate (Johnson Matthey, 65 mg, 0.29 mmol), tri-o-tolylphosphine (Aldrich, 176 mg, 0.6 mmol), bromobenzene (Aldrich, 2.50 g, 16.0 mmol), and triethylamine (Aldrich, 1.62 g, 16 mmol) was refluxed under nitrogen for 30 minutes. After cooling this mixture to room temperature, the isomer B of the title material of Example 18 (2.2 g, 14.5 mmol) in 6 mL of acetonitrile was added to the reaction mixture. The reaction was refluxed for 24 hrs., cooled to room temperature, and stripped of all solvent under reduced pressure. The residue was partitioned between saturated NaHCO₃ and EtOAc and the organic was dried (Na₂SO₄), filtered and concentrated to the crude product. This material was chromatographed (HPLC) on silica gel eluting with acetone/hexane (1:1) to give 1.06 g (32%) of the title material. Elemental analysis: $C_{15}H_{19}NO$ (MW=229.32)

|  | C | H | N |
|---|---|---|---|
| Calculated: | 78.57 | 8.36 | 6.11 |
| Found: | 78.14 | 8.31 | 5.89 |

EXAMPLE 33
3,4,5,6-tetrahydro-7-methoxy-2-(3-phenyl-2-propenyl)-2H-azepine

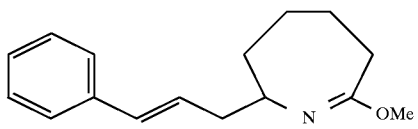

The title material of Example 32 (0.50 g, 2.2 mmol) in CH₂Cl₂ (15 mL) and in the presence of 3A molecular sieves (1.0 g) was reacted with trimethyloxonium tetrafluoroborate (0.39 g, 2.6 mmol) by the method of Example 3 to produce 0.53 g (99%) of the title material.

EXAMPLE 34
hexahydro-7-(3-phenyl-2-propenyl)-1H-azepin-2-imine, monohydrochloride

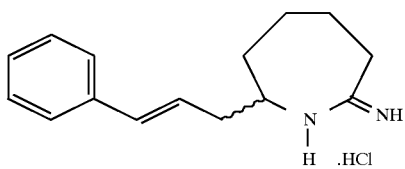

The product of Example 33 (0.50 g, 2.05 mmol) in 18 mL of MeOH was reacted with ammonium chloride (144 mg, 2.7 mmol) by the method of Example 5 to yield 258 mg (30%) of the title material.

HRMS (EI) calcd for $C_{15}H_{20}N_2$ m/e 228.163, found m/e 228.163. ¹H NMR(CD₃OD): d 7.40–7.17 (m, 5H), 6.59 (d, 1H, J=16 Hz), 6.26 (dt, 1H, J=16, 7 Hz), 3.80 (m, 1H), 2.80 (td, 1H, J=15, 2 Hz), 2.55 (m, 2H), 2.64 (dd, 1H, J=15, 6 Hz), 2.03–1.92 (m, 3H), 1.70 (m, 1H), 1.55–1.38 (m, 2H). Elemental analysis: $C_{15}H_{20}N_2 \cdot HCl \cdot 0.8\ H_2O \cdot 0.05\ NH_4Cl$ (MW=281.88)

|  | C | H | N | Cl |
|---|---|---|---|---|
| Calculated: | 63.91 | 8.15 | 10.19 | 13.21 |
| Found: | 63.86 | 8.10 | 9.97 | 13.42 |

EXAMPLE 35
hexahydro-7-(3-phenylpropyl)-1H-azepin-2-one

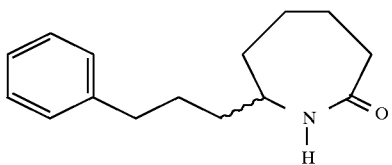

The title material of Example 32 (0.46 g, 2.0 mmol) in MeOH and 4% Pd on carbon (0.10 g) were combined in a standard Parr apparatus (125 mL bottle). The hydrogenation was carried out at room temperature under a H₂ pressure of 5 psi for 1 hr. All solvent was then removed under reduced pressure to yield 0.50 g (99%) of the title material as a white semi-solid. Elemental analysis: $C_{15}H_{21}NO$ (MW=231.33)

|  | C | H | N |
|---|---|---|---|
| Calculated: | 77.28 | 9.17 | 6.01 |
| Found: | 77.15 | 8.97 | 5.89 |

EXAMPLE 36
3,4,5,6-tetrahydro-7-methoxy-2-(3-phenylpropyl)-2H-azepine

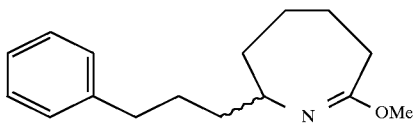

The title material of Example 35 (0.47 g, 2.0 mmol) in CH₂Cl₂ (10 mL) and in the presence of 3A molecular sieves (1.0 g) was reacted with trimethyloxonium tetrafluoroborate (0.35 g, 2.4 mmol) by the method of Example 3 to produce 0.42 g (87%) of the title material as a pale yellow oil.

EXAMPLE 37
hexahydro-7-(3-phenylpropyl)-1H-azepin-2-imine, monohydrochloride

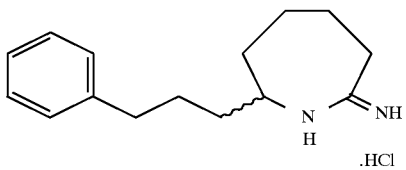

The product of Example 36 (0.41 g, 1.65 mmol) in 18 mL of EtOH was reacted with ammonium chloride (75 mg, 1.4 mmol) by the method of Example 5 to yield 195 mg (63%) of the title material.

HRMS (EI) calcd for $C_{15}H_{22}N_2$ m/e 230.178, found m/e 230.178. ¹H NMR(CD₃OD): d 7.28–7.13 (m, 5H), 3.57 (m, 1H), 2.73 (ddd, 1H, J=15,12, 2 Hz), 2.67 (t, 2H, J=8 Hz), 2.57 (dd, 1H, J=15, 7 Hz), 1.96 (m, 2H), 1.85–1.57 (m, 6H), 1.47 (m, 1H), 1.35 (m, 1H). Elemental analysis: $C_{15}H_{22}N_2 \cdot HCl \cdot 0.25\ H_2O$ (MW=271.32)

|  | C | H | N | Cl |
|---|---|---|---|---|
| Calculated: | 66.40 | 8.73 | 10.32 | 13.07 |
| Found: | 66.31 | 8.91 | 10.10 | 13.06 |

EXAMPLE 38
2-[(tetrahydro-2-furanyl)methyl]cyclohexanone

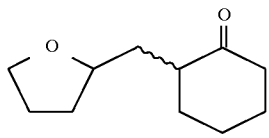

2-carboethoxycyclohexanone (1 mmol), finely powdered potassium carbonate (2 mmol), 2-bromomethyltetrahydrofuran (1.5 mmol), and tetrabutylammonium iodide (10 mg/mmol) are combined in dry DMF (1.25 mL/mmol) and stirred under $N_2$ at 55° to 60° C. for 16 to 18 hours. The room temperature reaction mixture is poured into water and extracted with $Et_2O$ and EtOAc. The combined organics are washed with brine, dried, and stripped of all solvent under reduced pressure to provide 2-tetrahydrofuranylmethyl-2-carboethoxycyclohexanone. This material is combined with lithium chloride (5 mmol), water (1.05 mmol) and dimethyl sulfoxide (5 mL/mmol) and the mixture refluxed for approximately 4 hrs. The mixture is poured into water and extracted with $Et_2O$ and EtOAc. The combined organics are washed with brine, dried, and stripped of all solvent under reduced pressure to generate the title material.

EXAMPLE 39
2-[(tetrahydro-2-furanyl)methyl]cyclohexanone, oxime

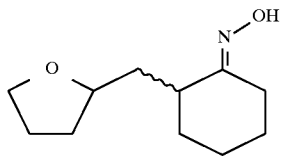

The product of Example 38 is reacted with hydroxylamine hydrochloride and NaOAc in a mixture of EtOH and water, by the method of Example 1 to produce the title material.

EXAMPLE 40
hexahydro-7-[(tetrahydro-2-furanyl)methyl]-1H-azepin-2-one, mixture with hexahydro-3-[(2-tetrahydrofuranyl)methyl]-1H-azepin-2-one

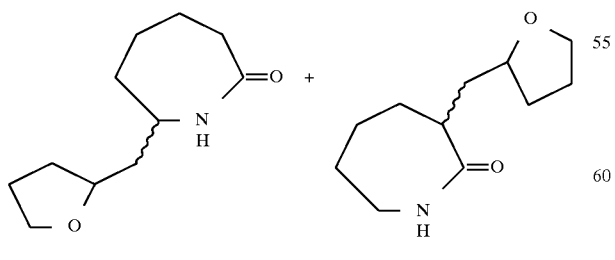

Isomer-A        Isomer-B

The product of Example 39 is reacted with 80% $H_2SO_4$, by the method of Example 2 to produce the title materials.

EXAMPLE 41
3,4,5,6-tetrahydro-7-methoxy-2-[(tetrahydro-2-furanyl)methyl]-2H-azepine

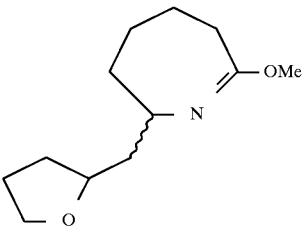

The Isomer-A product of Example 40 is reacted with trimethyloxonium tetrafluoroborate by the method of Example 3 to produce the title material.

EXAMPLE 42
3,4,5,6-tetrahydro-7-methoxy-6-[(tetrahydro-2-furanyl)methyl]-2H-azepine

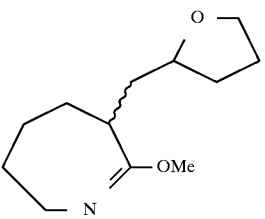

The isomer-B product of Example 40 is reacted with trimethyloxonuim tetrafluoroborate by the method of Example 3 to produce the title material.

EXAMPLE 43
hexahydro-7-[(tetrahydro-2-furanyl)methyl]-1H-azepin-2-imine, monohydrochloride

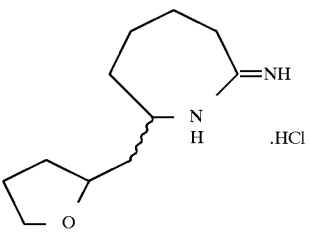

The title product of Example 41 in MeOH is reacted with ammonium chloride by the method of Example 5 to generate the title material.

EXAMPLE 44
hexahydro-3-[(tetrahydro-2-furanyl)methyl]-1H-azepin-2-imine, monohydrochloride

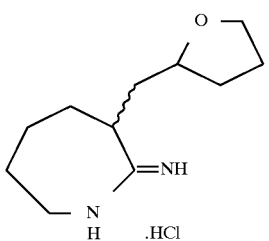

The title product of Example 42 in MeOH is reacted with ammonium chloride by the method of Example 5 to generate the title material.

EXAMPLE 45
2-[(2-furanyl)methyl]cyclohexanone

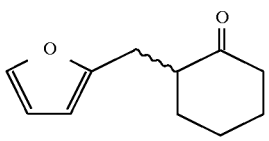

2-carboethoxycyclohexanone, finely powdered potassium carbonate, 2-bromomethyl furan, and tetrabutylammonium iodide are reacted by the method of Example 38 to generate the title material.

EXAMPLE 46
2-[(2-furanyl)methyl]cyclohexanone, oxime

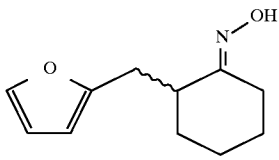

The product of Example 45 is reacted with hydroxylamine hydrochloride and NaOAc in a mixture of EtOH and water, by the method of Example 1 to produce the title material.

EXAMPLE 47
7-[(2-furanyl)methyl]hexahydro-1H-azepin-2-one, mixture with 3-[(2-furanyl)methyl]hexahydro-1H-azepin-2-one

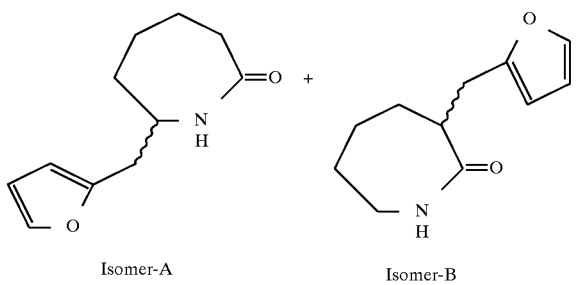

Isomer-A     Isomer-B

The product of Example 46 is reacted with 80% $H_2SO_4$, by the method of Example 2 to produce the title materials.

EXAMPLE 48
2-[(2-furanyl)methyl]-3,4,5,6-tetrahydro-7-methoxy-2H-azepine

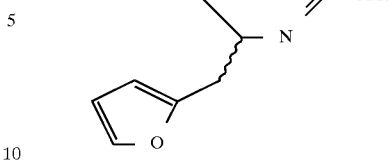

The Isomer-A product of Example 47 is reacted with trimethyloxonium tetrafluoroborate by the method of Example 3 to produce the title material.

EXAMPLE 49
6-[(2-furanyl)methyl]-3,4,5,6-tetrahydro-7-methoxy-2H-azepine

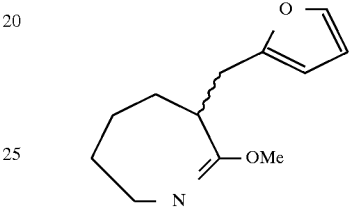

The Isomer-B product of Example 47 is reacted with trimethyloxonium tetrafluoroborate by the method of Example 3 to produce the title material.

EXAMPLE 50
7-[(2-furanyl)methyl]hexahydro-1H-azepin-2-imine, mono-hydrochloride

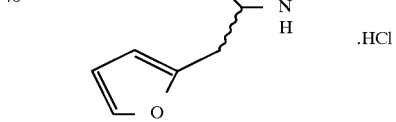

The title product of Example 48 in MeOH is reacted with ammonium chloride by the method of Example 5 to generate the title material.

EXAMPLE 51
3-[(2-furanyl)methyl]hexahydro-1H-azepin-2-imine, mono-hydrochloride

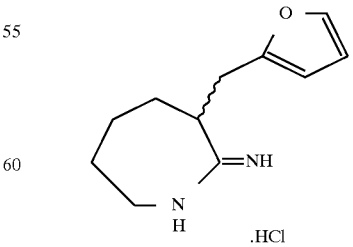

The title product of Example 49 in MeOH is reacted with ammonium chloride by the method of Example 5 to generate the title material.

EXAMPLE 52

2-[(2-thienyl)methyl]cyclohexanone

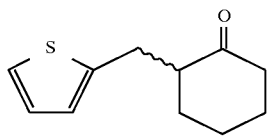

2-carboethoxycyclohexanone, finely powdered potassium carbonate, 2-bromomethyl thiophene, and tetrabutylammonium iodide are reacted by the method of Example 38 to generate the title material.

EXAMPLE 53

2-[(2-thienyl)methyl]cyclohexanone, oxime

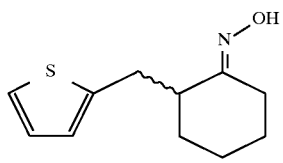

The product of Example 52 is reacted with hydroxylamine hydrochloride and NaOAc in a mixture of EtOH and water, by the method of Example 1 to produce the title material.

EXAMPLE 54 hexahydro-7-[(2-thienyl)methyl]-1H-azepin-2-one, mixture with hexahydro-3-[(2-thienyl)methyl]-1H-azepin-2-one

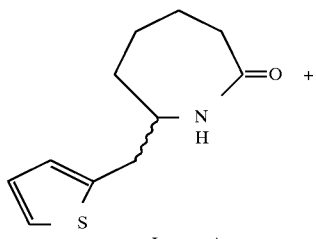
Isomer-A

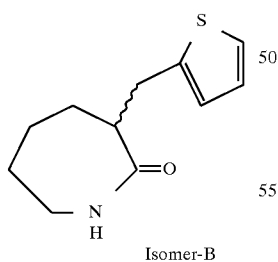
Isomer-B

The product of Example 53 is reacted with 80% $H_2SO_4$, by the method of Example 2 to produce the title materials.

EXAMPLE 55

3,4,5,6-tetrahydro-7-methoxy-2-[(2-thienyl)methyl]-2H-azepine

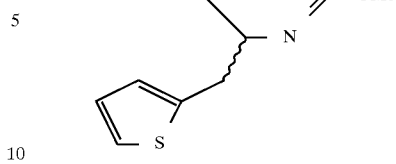

The Isomer-A product of Example 54 is reacted with trimethyloxonium tetrafluoroborate by the method of Example 3 to produce the title material.

EXAMPLE 56

3,4,5,6-tetrahydro-7-methoxy-6-[(2-thienyl)methyl]-2H-azepine

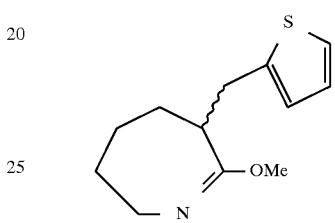

The Isomer-B product of Example 54 is reacted with trimethyloxonium tetrafluoroborate by the method of Example 3 to produce the title material.

EXAMPLE 57 hexahydro-7-[(2-thienyl)methyl]-1H-azepin-2-imine, monohydrochloride

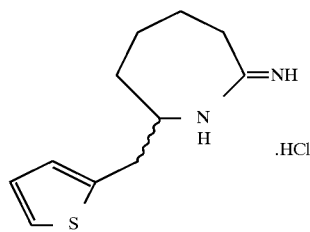

The title product of Example 55 in MeOH is reacted with ammonium chloride by the method of Example 5 to generate the title material.

EXAMPLE 58 hexahydro-3-[(2-thienyl)methyl]-1H-azepin-2-imine, monohydrochloride

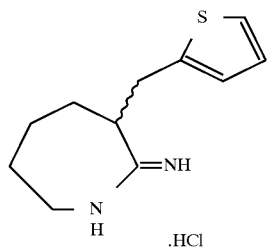

The title product of Example 56 in MeOH is reacted with ammonium chloride by the method of Example 5 to generate the title material.

EXAMPLE 59

4-phenyl-2-buten-1-ol

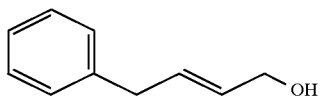

To a −10° C. solution of phenylmagnesium bromide, 3M in ether (68 mL) was added a solution of cupric acetate (5.6 g) and butadiene monoxide (6.43 mL) in THF (200 mL) over 40 min while maintaining the reaction temperature below −5° C. The reaction was stirred at −10° C. for 1 h, room temperature for 16 h, refluxed for 15 min then cooled to room temperature. Aqueous HCl (10%, 100 mL) was added and the mixture extracted with ethyl acetate. The organic solution was washed with aqueous HCl (10%), NaHCO$_3$ (saturated) and brine (saturated), dried (MgSO$_4$) and concentrated to yield a blue liquid. The residue was chromatographed to yield the title compound (6.3 g, 30%). Elemental analysis: C$_{10}$H$_{12}$O (MW=146.21)

|  | C | H |
|---|---|---|
| Calculated: | 82.15 | 8.27 |
| Found: | 82.18 | 8.61 |

EXAMPLE 60

2,2,2-trichloro-N-[1-(phenylmethyl)-2-propenyl]acetamide

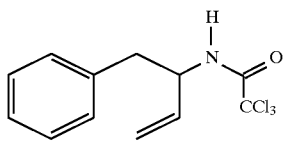

A solution of the product of Example 59 (5.15 g) in ether (20 mL) was added to a suspension of NaH (0.1 equivalent) in ether (40 mL). The solution was cooled to −15° C. and treated with trichloroacetonitrile (3.6 mL) over 30 min, the solution was stirred at room temperature for 1 h, treated with a solution of pentane (100 mL) and methanol (0.4 mL), filtered and concentrated. The residue was then dissolved in xylene (500 mL) and refluxed for 12 h. Concentration of the reaction mixture followed by chromatography afforded the title material (6.9 g, 69%). Elemental analysis: C$_{12}$H$_{12}$NOCl$_3$ (MW=292.59)

|  | C | H | N |
|---|---|---|---|
| Calculated: | 49.26 | 4.13 | 4.79 |
| Found: | 48.88 | 4.07 | 4.76 |

EXAMPLE 61 trans-3,3-dichloro-4-(chloromethyl)-5-(phenylmethyl)pyrrolidin-2-one

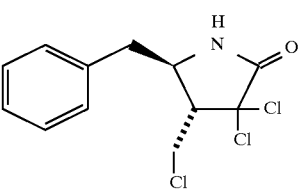

A solution of the product of Example 60 (2.7 g, 9.3 mmol) in xylene (100 mL) was reacted with bis-triphenylphosphine-ruthenium dichloride (300 mg) and refluxed for 8 h. Concentration of the reaction mixture followed by chromatography afforded the title material (1.5 g, 55%).

EXAMPLE 62 trans-4-methyl-5-(phenylmethyl)pyrrolidin-2-one

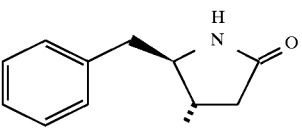

A solution of the product of Example 61 (1.3 g), tributyltin hydride (3.85 g) and AIBN (16 mg) in toluene (50 mL) was refluxed for 4 hours. The reaction mixture was treated with a solution of KF (20%, 40 mL) and ethyl acetate (100 mL), filtered, concentrated and chromatographed to yield the title material (270 mg). Elemental analysis: C$_{12}$H$_{15}$NO.0.1 CH$_3$CO$_2$C$_2$H$_5$ (MW=198.06)

|  | C | H | N |
|---|---|---|---|
| Calculated: | 75.19 | 8.04 | 7.07 |
| Found: | 74.84 | 7.92 | 7.15 |

EXAMPLE 63 trans-3,4-dihydro-5-methoxy-3-methyl-2-(phenylmethyl)-2H-pyrrole

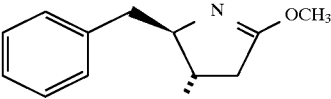

A solution of the product of Example 62 (400 mg, 2.0 mmol) in methylene chloride (25 mL) was treated with trimethyloxonium tetrafluoroborate (361 mg, 2.4 mmol) by the method of Example 3 to produce the title material (300 mg, 40%).

EXAMPLE 64

(±) (trans) 4-methyl-5-(phenylmethyl)pyrrolidin-2-imine, monohydrochloride

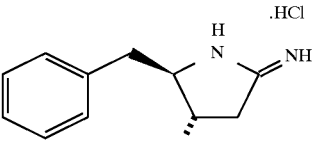

A solution of the title product of Example 63 (300 mg, 1.4 mmol) in MeOH (20 mL) was reacted with ammonium chloride (77 mg, 1.6 mmol) by the method of Example 5 followed by chromatography to generate the title material (240 mg, 75%).

MS (CIS) for $C_{12}H_{17}N_2$ (MW=188): m+189 (100%). Purity by analytical HPLC 97%.

EXAMPLE 65
2-(2-propenyl)cycloheptanone

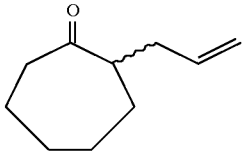

To a mechanically stirred mixture of potassium t-butoxide (Aldrich, 67.0 g, 0.6 mol) in benzene (600 mL) cooled to 0° C. under a nitrogen atmosphere was added cycloheptanone (Aldrich, 56.1 g, 0.5 mol) dropwise over 15 minutes. Ten minutes after the addition was complete, allyl bromide (Aldrich, 61.6 g, 0.51 mol) was added dropwise over 20 minutes. The reaction was warmed to room temperature, refluxed for 7 hrs., stirred at room temperature for 18 hrs., and diluted with 0.5N $KHSO_4$ (300 mL). This mixture was further diluted with $Et_2O$ (600 mL), 0.5N $KHSO_4$ (200 mL) and $H_2O$ (200 mL) before the organic was separated, washed with $H_2O$ (200 mL) and brine (200 mL), dried ($Na_2SO_4$), filtered, and stripped of all solvent under reduced pressure. The crude product (76.1 g) was distilled to yield 24.4 g (32%) of the title material (bp=104°–108° C., 25 mm of Hg). Elemental analysis: $C_{10}H_{16}O$ (MW=152.24)

|  | C | H |
|---|---|---|
| Calculated: | 78.90 | 10.59 |
| Found: | 78.96 | 10.36 |

EXAMPLE 66
2-(2-propenyl)cycloheptanone, oxime

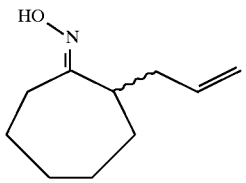

The title material of Example 65 (15.0 g, 98.5 mmol) was converted to the title compound by the method of Example 1 using 10.3 g (98.5 mmol) of hydroxylamine hydrochloride and 14.5 g (180.0 mmol) of NaOAc in a mixture of 90 mL of EtOH and 60 mL of water. The procedure produced 16.4 g (97%) of the title compound. Elemental analysis: $C_{10}H_{17}NO.0.25\ H_2O$ (MW=171.75)

|  | C | H | N |
|---|---|---|---|
| Calculated: | 69.93 | 10.27 | 8.16 |
| Found: | 69.67 | 10.08 | 8.03 |

EXAMPLE 67
octahydro-8-(2-propenyl)azocin-2-one, mixture with octahydro-3-(2-propenyl)azocin-2-one

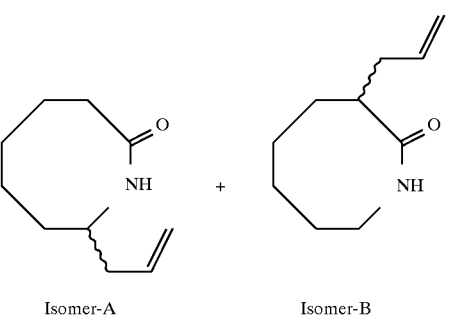

Isomer-A        Isomer-B

To the title product of Example 66 (16.2 g, 96.9 mmol) in 115 mL of acetone containing IN NaOH (110 mL, 110 mmol) cooled to 0° C. was added benzenesulfonyl chloride (17.6 g, 100 mmol) dropwise over 10 minutes. The reaction mixture was warmed to room temperature and stirred over night. After removing the acetone under reduced pressure, the residue was diluted with EtOAc (300 mL) and water (75 mL). The aqueous layer (pH=1) was separated and the organic layer was washed with 2×100 mL of 5% $KHCO_3$ and 2×75 mL of brine, dried over $Na_2SO_4$, filtered, and stripped of all solvent under reduced pressure. The crude residue (15.6 g) was separated into its Isomer-A (5.6 g, 34%) and Isomer-B (4.8 g, 29%) components by silica gel chromatography.

Isomer-A: Elemental analysis: $C_{10}H_{17}NO.0.125\ H_2O$ (MW=169.50)

|  | C | H | N |
|---|---|---|---|
| Calculated: | 70.86 | 10.26 | 8.26 |
| Found: | 70.68 | 10.22 | 8.19 |

Isomer-B: Elemental analysis: $C_{10}H_{17}NO.0.25\ H_2O$ (MW=171.75)

|  | C | H | N |
|---|---|---|---|
| Calculated: | 69.93 | 10.27 | 8.16 |
| Found: | 70.15 | 10.19 | 8.06 |

EXAMPLE 68
octahydro-8-(3-phenyl-2-propenyl)azocin-2-one

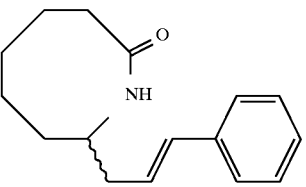

The Isomer A of the title material of Example 67 in acetonitrile is coupled to bromobenzene in the presence palladium acetate, tri-o-tolylphosphine, and triethylamine by the method of Example 32 to provide the title material.

EXAMPLE 69
2,3,4,5,6,7-hexahydro-8-methoxy-2-(3-phenyl-2-propenyl) azocine

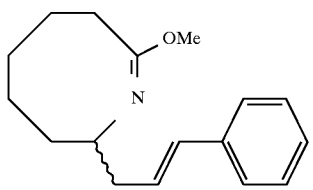

The product of Example 68 is reacted with trimethyloxonium tetrafluoroborate in CH$_2$Cl$_2$ by the method of Example 3 to produce the title material.

EXAMPLE 70 octahydro-8-(3-phenyl-2-propenyl)azocin-2-imine, monohydrochloride

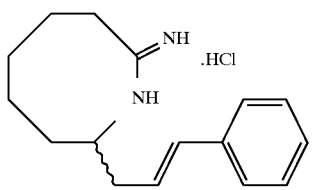

The title product of Example 69 in MeOH is reacted with ammonium chloride by the method of Example 5 to generate the title material.

EXAMPLE 71 octahydro-8-(3-phenylpropyl)azocin-2-one

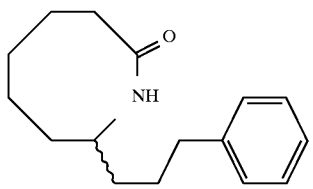

The title material of Example 68 in MeOH is hydrogenated over Pd on carbon in a standard Parr apparatus by the method of Example 35 to generate the title product.

EXAMPLE 72

2,3,4,5,6,7-hexahydro-8-methoxy-2-(3-phenylpropyl) azocine

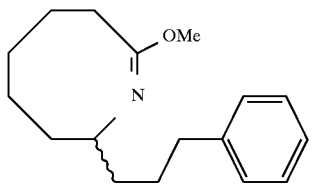

The product of Example 71 is reacted with trimethyloxonium tetrafluoroborate in CH$_2$Cl$_2$ by the method of Example 3 to produce the title material.

EXAMPLE 73 octahydro-8-(3-phenylpropyl)azocin-2-imine, monohydrochloride

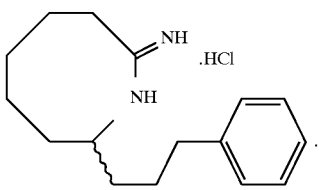

The title product of Example 72 in MeOH is reacted with ammonium chloride by the method of Example 5 to generate the title material.

EXAMPLE 74 ethyl 1,4-dioxaspiro[4.5]decane-6-carboxylate

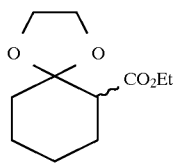

To ethyl 2-cyclohexanonecarboxylate (Aldrich, 169.5 g, 1.0 mol) and ethylene glycol (Sigma, 166.7 g, 2,7 mol) in benzene (1.5 L) was added pyridinium tosylate (50.2 g, 0.2 mol). The reaction was refluxed under a nitrogen atmosphere and the water generated was removed using a Dean-Stark trap. After cooling the reaction to room temperature, half of the benzene was removed under reduced pressure and the residue was washed with 25% aqueous NaHCO$_3$, stripped of all solvent, dissolved in CH$_2$Cl$_2$, dried (Na$_2$SO$_4$), filtered, and again stripped of all solvent under reduced pressure to provide 213 g of the title material.

EXAMPLE 75

1,4-dioxaspiro[4.5]decane-6-carboxaldehyde

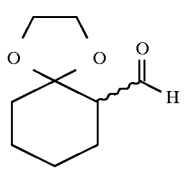

To the product of Example 74 (10.0 g, 46.7 mmol) in 150 mL of toluene cooled to −78° C. was added dropwise under argon (Ar) 93.5 mL (93.5 mmol) of diisobutylaluminum hydride (DIBAL) in toluene over a 15 min. period. After stirring this reaction for 45 min., MeOH (40 mL) were added dropwise followed by 200 mL of a saturated solution of Rochelle salts (potassium sodium tartrate tetrahydrate). The reaction was warmed to room temperature, stirred for one hour, and the organic layer was separated. The aqueous layer was washed with EtOAc and the organic layer was stripped of all toluene. The residue and the EtOAc extract were combined, diluted with EtOAc, washed with water, dried (MgSO$_4$), filtered and stripped of all solvent to yield the crude desired product. This material was chromatographed through silica gel eluting with a 1:1 mixture of EtOAc and hexane to yield 6.4 g of the title material as a colorless oil.

EXAMPLE 76

2-ethenylcyclohexanone

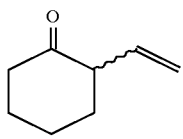

To a cold suspension of methylphosphonium bromide in Et₂O under Ar is added an Et₂O solution of potassium hexamethyldisilylazide (KHMDS). After stirring this mixture for one hr, the title material of Example 75, dissolved in Et₂O, is added dropwise to the stirred reaction mixture. The reaction is allowed to stir cold, warm to room temperature and to stir at room temperature. After quenching the reaction with water, it is extracted with Et₂O, dried, stripped of solvent under reduced pressure to yield the crude product. The title material is isolated from the crude product by silica gel chromatography. Alternatively, the title material is synthesized by the method described by S. Kim and S. Lee, *Tetrahedron Letters*, 1991, 32, 6575–6578.

EXAMPLE 77

2-ethenylcyclohexanone, oxime

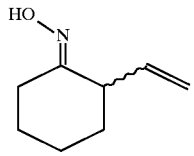

The product of Example 76 is reacted with hydroxylamine hydrochloride and NaOAc in a mixture of EtOH and water, by the method of Example 1 to produce the title material.

EXAMPLE 78

7-ethenylhexahydro-1H-azepin-2-one, mixture with 3-ethenylhexahydro-1H-azepin-2-one

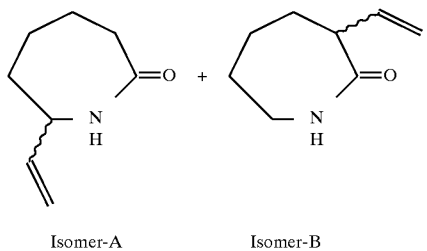

The title product of Example 77 in acetone containing 1N NaOH is reacted with benzenesulfonyl chloride by the method described in Example 67 to generate the Isomer-A and Isomer-B title materials.

EXAMPLE 79 methyl 2-[2-(hexahydro-7-oxo-1H-azepin-2-yl)ethenyl]benzoate

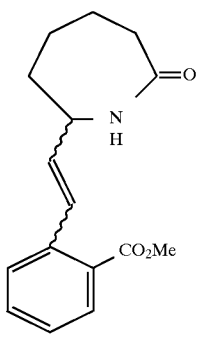

The Isomer A of the title material of Example 78 in acetonitrile is coupled to methyl 2-bromobenzoate (Aldrich) in the presence palladium acetate, tri-o-tolylphosphine, and triethylamine by the method of Example 32 to provide the title material as either or both the Z and E isomers.

EXAMPLE 80 methyl 2-[2-(3,4,5,6-tetrahydro-7-methoxy-2H-azepin-2-yl)ethenyl]benzoate

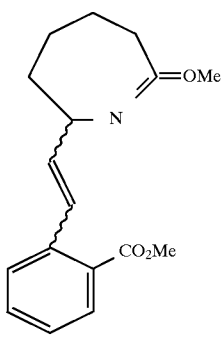

The product of Example 79 is reacted with trimethyloxonium tetrafluoroborate in CH₂Cl₂ by the method of Example 3 to produce the title material.

EXAMPLE 81 methyl 2-[2-(hexahydro-7-imino-1H-azepin-2-yl)ethenyl]benzoate, monohydrochloride

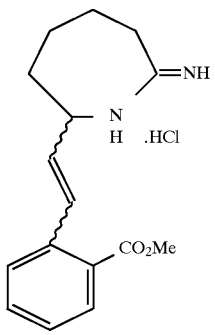

The title product of Example 80 in MeOH is reacted with ammonium chloride by the method of Example 5 to generate the title material.

EXAMPLE 82 methyl 2-[2-(hexahydro-7-oxo-1H-azepin-2-yl)ethyl]benzoate

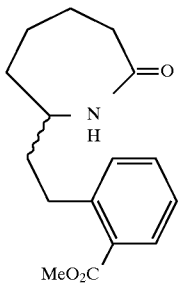

The title material of Example 79 in MeOH is hydrogenated over Pd on carbon in a standard Parr apparatus by the method of Example 35 to generate the title product.

EXAMPLE 83 methyl 2-[2-(3,4,5,6-tetrahydro-7-methoxy-2H-azepin-2-yl)ethyl]benzoate

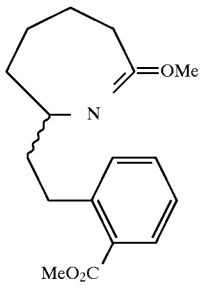

The product of Example 82 is reacted with trimethyloxonium tetrafluoroborate in CH$_2$Cl$_2$ by the method of Example 3 to produce the title material.

EXAMPLE 84 methyl 2-[2-(hexahydro-7-imino-1H-azepin-2-yl)ethyl]benzoate, monohydrochloride

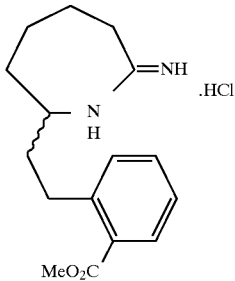

The title product of Example 83 in MeOH is reacted with ammonium chloride by the method of Example 5 to generate the title material.

EXAMPLE 85 methyl 2-[2-(hexahydro-2-oxo-1H-azepin-3-yl)ethenyl]benzoate

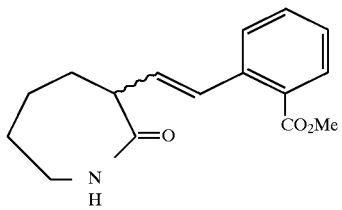

The Isomer B of the title material of Example 78 in acetonitrile is coupled to methyl 2-bromobenzoate (Aldrich) in the presence palladium acetate, tri-o-tolylphosphine, and triethylamine by the method of Example 32 to provide the title material as either or both the Z and E isomers.

EXAMPLE 86 methyl 2-[2-(3,4,5,6-tetrahydro-7-methoxy-2H-azepin-6-yl)ethenyl]benzoate

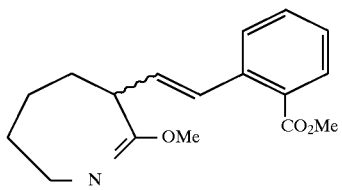

The product of Example 85 is reacted with trimethyloxonium tetrafluoroborate in CH$_2$Cl$_2$ by the method of Example 3 to produce the title material.

EXAMPLE 87 methyl 2-[2-(hexahydro-2-imino-1H-azepin-3-yl)ethenyl]benzoate, monohydrochloride

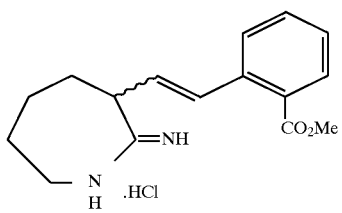

The title product of Example 86 in MeOH is reacted with ammonium chloride by the method of Example 5 to generate the title material.

EXAMPLE 88 methyl 2-[2-(hexahydro-2-oxo-1H-azepin-3-yl)ethyl]benzoate

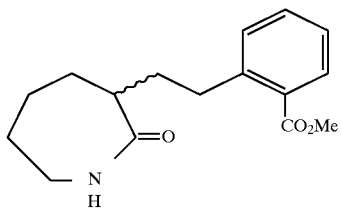

The title material of Example 85 in MeOH is hydrogenated over Pd on carbon in a standard Parr apparatus by the method of Example 35 to generate the title product.

EXAMPLE 89 methyl 2-[2-(3,4,5,6-tetrahydro-7-methoxy-2H-azepin-6-yl)ethyl]benzoate

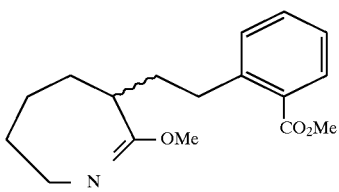

The product of Example 88 is reacted with trimethyloxonium tetrafluoroborate in CH$_2$Cl$_2$ by the method of Example 3 to produce the title material.

EXAMPLE 90 methyl 2-[2-(hexahydro-2-imino-1H-azepin-3-yl)ethyl]benzoate, monohydrochloride

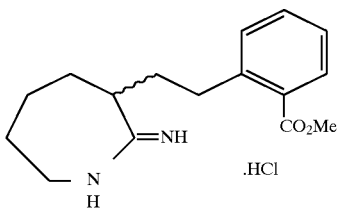

The title product of Example 89 in MeOH is reacted with ammonium chloride by the method of Example 5 to generate the title material.

EXAMPLE 91 methyl 3-[2-(hexahydro-7-oxo-1H-azepin-2-yl)ethenyl]benzeneacetate

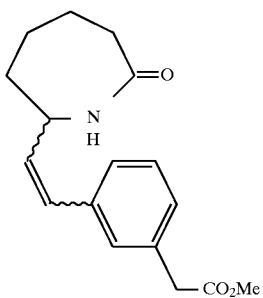

The Isomer A of the title material of Example 78 in acetonitrile is coupled to methyl 3-bromobenzeneacetate (Aldrich) in the presence palladium acetate, tri-o-tolylphosphine, and triethylamine by the method of Example 32 to provide the title material as either or both the Z and E isomers.

EXAMPLE 92 methyl 2-[2-(3,4,5,6-tetrahydro-7-methoxy-2H-azepin-6-yl)ethenyl]benzeneacetate

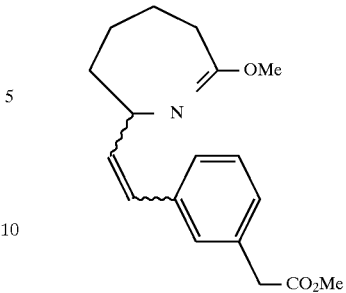

The product of Example 91 is reacted with trimethyloxonium tetrafluoroborate in CH$_2$Cl$_2$ by the method of Example 3 to produce the title material.

EXAMPLE 93 methyl 3-[2-(hexahydro-7-imino-1H-azepin-2-yl)ethenyl]benzeneacetate, monohydrochloride

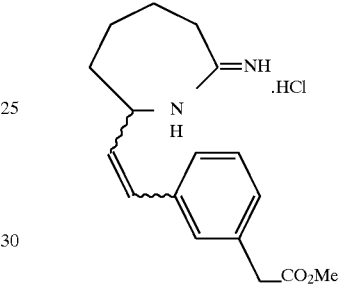

The title product of Example 89 in MeOH is reacted with ammonium chloride by the method of Example 5 to generate the title material.

EXAMPLE 94

6-(phenylmethyl)piperidin-2-imine, monohydrochloride

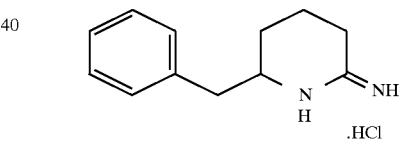

2-benzylpyridine (Aldrich, 2.5 g, 0.015 mole), sodium amide (780 mg, 0.02 mole) and N, N-dimethylaniline (25 mL) were refluxed overnight. Contents were allowed to cool and partitioned between ether (Et$_2$O) and water. The ether layer was dried (MgSO$_4$) and concentrated in vacuo leaving an oil. The oil was purified by chromatography. The purified material was dissolved in 1N HCl, lyophilized, and triturated with EtOAc to give 2-amino-6-benzylpyridine as a white solid. This 2-amino-6-benzylpyridine (470 mg), 5% rhodium/carbon (250 mg), and glacial acetic acid (30 mL) were shaken at 55 psi hydrogen on a Parr hydrogenation apparatus overnight. More catalyst (300 mg) was added and contents were again shaken at 55 psi hydrogen overnight. Contents were filtered and the filtrate was concentrated in vacuo leaving a viscous oil (500 mg). The product was purified by C-18 reverse phase chromatography to give a white solid. The solid was dissolved in 1N HCl, lyophilized, and recrystallized from EtOH/EtOAc to give the desired as a white solid. The analysis of the product was found to be consistent with the proposed structure.

MH+=189. $^1$H NMR (CDCl$_3$): d 9.85 (s, 1H); 8.95 (s, 1H); 8.62 (s, 1H); 7.40–7.10 (m, 5H); 3.80–3.60 (m, 1H);

3.20–3.00 (m, 1H); 2.90–2.70 (m, 2H); 2.65–2.45 (m, 1H); 2.42–2.25 (m, 2H); 1.92 (m, 2H); 1.75 (m, 1H); 1.50–1.35 (m, 1H).

EXAMPLE 95

6-(cyclohexylmethyl)piperidin-2-imine, monohydrochloride

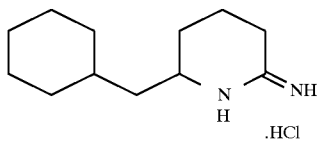

The 2-amino-6-benzylpyridine was reduced as in Example 94, except platinum oxide was used as the catalyst. The product was obtained as an oil which was dissolved in 1N HCl and lyophilized to give a white solid. The solid was recrystallized from EtOAc to give the desired title compound as white crystals. The analysis of the product was found to be consistent with the proposed structure.

MH+=195. $^1$H NMR (CDCl$_3$): d 9.60 (s, 1H); 8.90 (s, 1H); 8.70 (s, 1H); 3.60–3.40 (m, 1H); 2.90–2.70 (m, 1H); 2.70–2.50 (m, 1H); 2.10–1.80 (m, 2H); 1.80–1.00 (m, 13H); 1.00–0.80 (m, 2H).

EXAMPLE 96

6-(3-phenyl-2-propenyl)piperidin-2-one

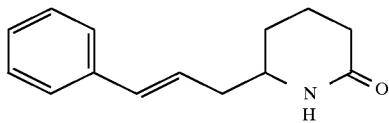

6-Allyl valerolactam is reacted with bromobenzene by the method of Example 32 to generate the title compound.

EXAMPLE 97

2,3,4,5-tetrahydro-6-methoxy-2-(3-phenyl-2-propenyl)pyridine

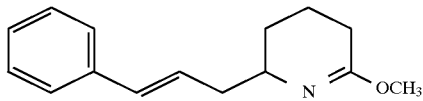

The product of Example 96 is reacted with trimethyloxonium tetrafluoroborate by the method of Example 3 to generate the title compound.

EXAMPLE 98

6-(3-phenyl-2-propenyl)piperidin-2-imine, monohydrochloride

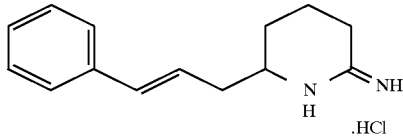

The product of Example 97 is reacted with ammonium chloride by the method of Example 5 to generate the title compound.

EXAMPLE 99

6-(3-phenylpropyl)piperidin-2-one

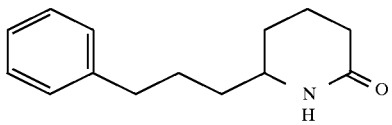

The product of Example 96 is hydrogenated by the method of Example 35 to generate the title compound.

EXAMPLE 100

2,3,4,5-tetrahydro-6-methoxy-2-(3-phenylpropyl)pyridine

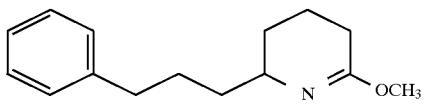

The product of Example 99 is reacted with trimethyloxonium tetrafluoroborate by the method of Example 3 to generate the title compound.

EXAMPLE 101

6-(3-phenylpropyl)piperidin-2-imine, monohydrochloride

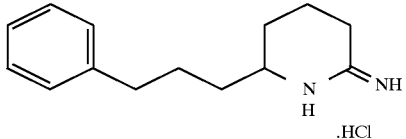

The product of Example 100 is reacted with ammonium chloride by the method of Example 5 to generate the title compound.

EXAMPLE 102 methyl 1-[2-(1,3-dioxolan-2-yl)ethyl]-2-oxocyclohexanecarboxylate

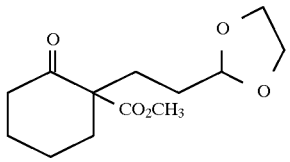

A solution of 2-carbomethoxycyclohexanone (2.0 g, 12.8 mmoles) in 50 mL of DMF was reacted at 70° C. for 15 h with 2-(2-bromoethyl)-1,3-dioxolane (4.6 g, 25 mmoles) and potassium carbonate (4.8 g, 34.8 mmoles). The reaction mixture was diluted to 500 mL with water and extracted with ethyl ether/ethyl acetate. the organic extracts were dried over sodium sulfate, and the solvent was evaporated to generate the title compound as an oil. FAB-MS: m/z263 (M+Li).

EXAMPLE 103
2-[2-(1,3-dioxolan-2-yl)ethyl]cyclohexanone

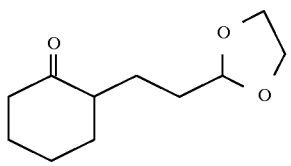

The product of Example 102 was reacted with sodium cyanide (0.69 g, 14.1 mmoles) in 25 mL of DMSO at 160° C. for 12 hrs. The reaction mixture was then diluted to 700 mL with water and extracted with ethyl acetate/hexane (1:1). The solvent removed from the extracts to provide the title compound as oil. FAB-MS: m/z205.7 (M+Li).

EXAMPLE 104
2-[2-(1,3-dioxolan-2-yl)ethyl]cyclohexanone, oxime

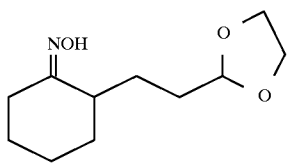

The product of Example 103 was reacted with hydroxylamine hydrochloride (1.25 g, 18 mmoles) and sodium acetatetrihydrate (2.9 g, 21 mmoles) in 30 mL ethanol/water (2:1) for 4 hrs under gentle reflux. The solvent was evaporated and the solid dissolved in ethyl acetate, washed with sat. sodium chloride, dried over sodium sulfate, and the solvent stripped off to leave the title compound as an oil. FAB-MS: m/z214.1 (M+H).

EXAMPLE 105
7-[2-(1,3-dioxolan-2-yl)ethyl]hexahydro-1H-azepin-2-one

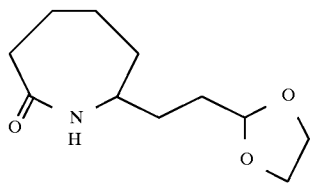

The product of Example 104 is reacted with benzenesulfonyl chloride and sodium hydroxide in acetone/water by the method of Example 67 to generate the title compound.

EXAMPLE 106
2-[2-(1,3-dioxolan-2-yl)ethyl]-3,4,5,6-tetrahydro-7-methoxy-2H-azepine

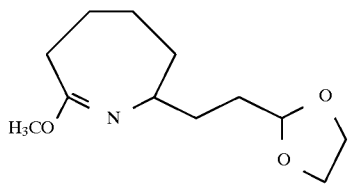

The product of Example 105 is reacted with trimethyloxonium tetrafluoroborate by the method of Example 3 to generate the title compound.

EXAMPLE 107
7-[2-(1,3-dioxolan-2-yl)ethyl]hexahydro-1H-azepin-2-imine, monohydrochloride

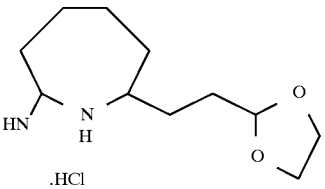

The product of Example 106 is reacted with ammonium chloride by the method of Example 5 to generate the title compound.

EXAMPLE 108
methyl 1-[2-(1,3-dioxan-2-yl)ethyl]-2-oxocyclohexanecarboxylate

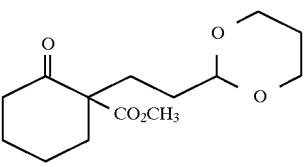

A solution of 2-carbomethoxycyclohexanone in DMF is reacted with 2-(2-bromoethyl)-1,3-dioxane and potassium carbonate by the method of Example 102 to generate the title compound.

EXAMPLE 109
2-[2-(1,3-dioxan-2-yl)ethyl]cyclohexanone

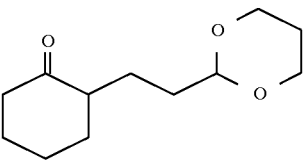

The product of Example 108 is reacted with sodium cyanide in DMSO at 160° C. by the method of Example 103 to generate the title compound.

EXAMPLE 110
2-[2-(1,3-dioxan-2-yl)ethyl]cyclohexanone, oxime

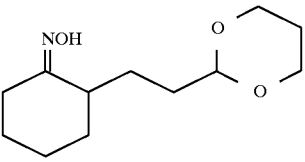

The product of Example 109 is reacted with hydroxylamine hydrochloride and sodium acetate in ethanol/water by the method of Example 1 to generate the title compound.

EXAMPLE 111

7-[2-(1,3-dioxan-2-yl)ethyl]hexahydro-1H-azepin-2-one

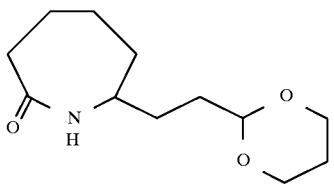

The product of Example 110 is reacted with benzenesulfonyl chloride and sodium hydroxide in acetone/water by the method of Example 67 to generate the title compound.

EXAMPLE 112

2-[2-(1,3-dioxan-2-yl)ethyl]-3,4,5,6-tetrahydro-7-methoxy-2H-azepine

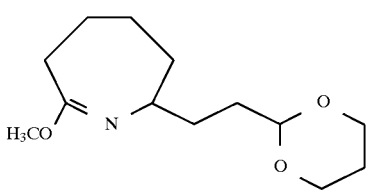

The product of Example 111 is reacted with trimethyloxonium tetrafluoroborate by the method of Example 3 to generate the title compound.

EXAMPLE 113

7-[2-(1,3-dioxan-2-yl)ethyl]hexahydro-1H-azepin-2-imine, monohydrochloride

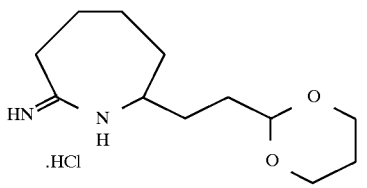

The product of Example 112 is reacted with ammonium chloride by the method of Example 5 to generate the title compound.

EXAMPLE 114

7-[[4,5-dihydro-3-(trifluoromethyl)isoxazol-5-yl]methyl] hexahydro-1H-azepin-2-one, mixture with 7-[[4,5-dihydro-3-(trifluoromethyl)isoxazol-4-yl]methyl]hexahydro-1H-azepin-2-one

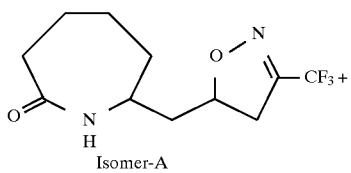
Isomer-A

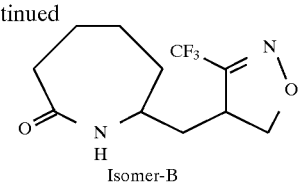
Isomer-B

The title product isomer B of Example 18 (7-allyl caprolactam) is reacted with trifluoromethyloximoyl chloride and triethylamine in toluene by the method of R. Huisgen, *Ang. Chem. Int. Ed.* 1963, 2(10), 562, to generate a mixture of the two title compounds. The title Isomer-A and Isomer-B materials are separated by HPLC.

EXAMPLE 115

2-[[4,5-dihydro-3-(trifluoromethyl)isoxazol-5-yl]methyl]3,4,5,6-tetrahydro-7-methoxy-2H-azepine

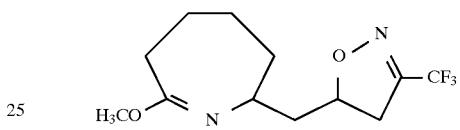

The title Isomer-A of Example 114 is reacted with trimethyloxonium tetrafluoroborate by the method of Example 3 to generate the title compound.

EXAMPLE 116

7-[[4,5-dihydro-3-(trifluoromethyl)isoxazol-5-yl]methyl] hexahydro-1H-azepin-2-imine, monohydrochloride

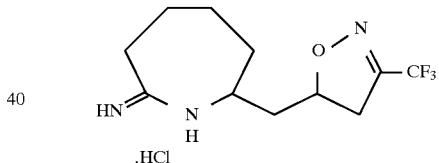

The product of Example 115 is reacted with ammonium chloride by the method of Example 5 to generate the title compound.

EXAMPLE 117

2-[[4,5-dihydro-3-(trifluoromethyl)isoxazol-4-yl]methyl]-3,4,5,6-tetrahydro-7-methoxy-2H-azepine

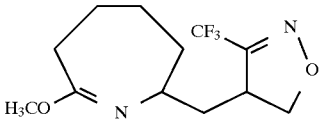

The title Isomer-B of Example 114 is reacted with trimethyloxonium tetrafluoroborate by the method of Example 3 to generate the title compound.

EXAMPLE 118

7-[[4,5-dihydro-3-(trifluoromethyl)isoxazol-4-yl]methyl] hexahydro-1H-azepin-2-imine, monohydrochloride

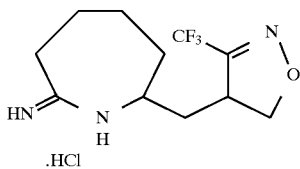

The title product of Example 117 is reacted with ammonium chloride by the method of Example 5 to generate the title compound.

EXAMPLE 119
hexahydro-7-[[3-(trifluoromethyl)isoxazol-5-yl]methyl]-1H-azepin-2-one

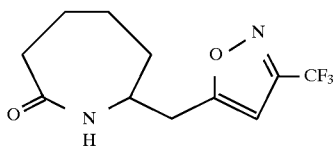

The title Isomer-A of Example 114 is reacted with manganese dioxide in benzene/dioxane by the method of A. Barco, *Synth. Commun.* 1978, 8, 219, to generate the title compound.

EXAMPLE 120
3,4,5,6-tetrahydro-7-methoxy-2-[[3-(trifluoromethyl)isoxazol-5-yl]methyl]-2H-azepine

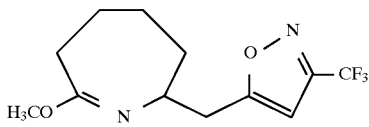

The title product of Example 119 is reacted with trimethyloxonium tetrafluoroborate by the method of Example 3 to generate the title compound.

EXAMPLE 121
hexahydro-7-[[3-(trifluoromethyl)isoxazol-5-yl]methyl]-1H-azepin-2-imine, monohydrochloride

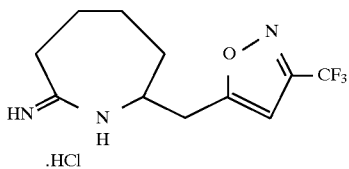

The title product of Example 120 is reacted with ammonium chloride by the method of Example 5 to generate the title compound.

EXAMPLE 122
hexahydro-7-[[3-(trifluoromethyl)isoxazol-4-yl]methyl]-1H-azepin-2-one

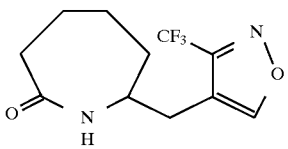

The title Isomer-B of Example 114 is reacted with manganese dioxide in benzene/dioxane by the method of A. Barco, *Synth. Commun.* 1978, 8, 219, to generate the title compound.

EXAMPLE 123
3,4,5,6-tetrahydro-7-methoxy-2-[[3-(trifluoromethyl)isoxazol-4-yl]methyl]-2H-azepine

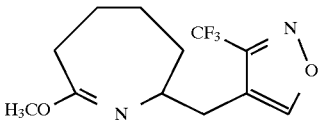

The title product of Example 122 is reacted with trimethyloxonium tetrafluoroborate by the method of Example 3 to generate the title compound.

EXAMPLE 124
hexahydro-7-[[3-(trifluoromethyl)isoxazol-4-yl]methyl]-1H-azepin-2-imine, monohydrochloride

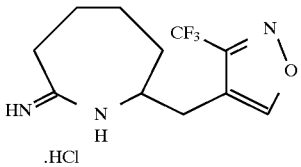

The title product of Example 123 is reacted with ammonium chloride by the method of Example 5 to generate the title compound.

EXAMPLE 125
7-[(4,5-dihydro-3-phenylisoxazol-4-yl)methyl]hexahydro-1H-azepin-2-one, mixture with 7-[(4,5-dihydro-3-phenylisoxazol-5-yl)methyl]hexahydro-1H-azepin-2-one

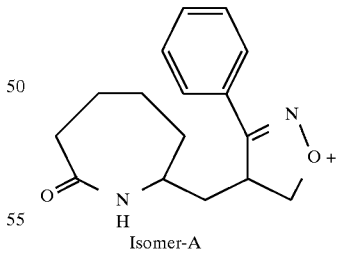
Isomer-A

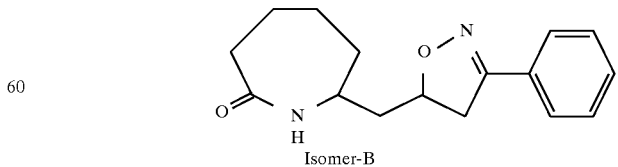
Isomer-B

The title product Isomer B of Example 18 (7-Allyl caprolactam) is reacted with benzaldehydeoximinoyl chloride and triethylamine in toluene by the method of R.

Huisgen, *Ang. Chem. Int. Ed.* 1963, 2(10), 562: To a solution of 2 g (0.013 mol) of benzaldehyde oximinoyl chloride and 1g (0.006 mol) of 7-allylcaprolactam in 30 mL of ethyl ether was added 1.3 g (0.013 mol) of triethylamine dropwise. This mixture was stirred at 25° C. for 18 hours. The mixture was then diluted with ethyl acetate, washed with dilute HCl, dried (MgSO$_4$), filtered and concentrated to afford an off-white semi-solid. Trituration with ethyl ether and filtration afforded 1.1 g of an off-white solid. Column chromatography (ethyl acetate) afforded a mixture of the title compounds as a white solid, mp=118°–128° C., M+H=273. The title Isomer-A and Isomer-B materials are separated by HPLC.

EXAMPLE 126
hexahydro-7-[(3-phenylisoxazol-4-yl)methyl]-1H-azepin-2-one

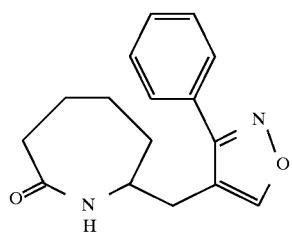

The title Isomer-A material of Example 125 is reacted with manganese dioxide in benzene/dioxane by the method of A. Barco, *Synth. Commun.* 1978, 8, 219, to generate the title compound.

EXAMPLE 127
3,4,5,6-tetrahydro-7-methoxy-2-[(3-phenylisoxazol-4-yl)methyl]-2H-azepine

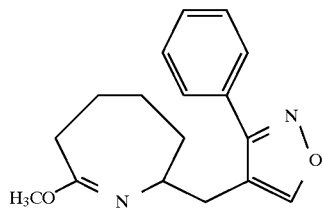

The title product of Example 126 is reacted with trimethyloxonium tetrafluoroborate by the method of Example 3 to generate the title compound.

EXAMPLE 128
hexahydro-7-[(3-phenylisoxazol-4-yl)methyl]-1H-azepin-2-imine, monohydrochloride

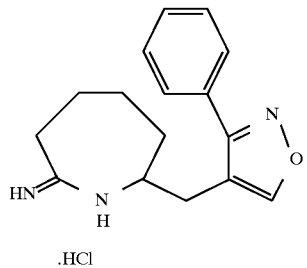

The title product of Example 127 is reacted with ammonium chloride by the method of Example 5 to generate the title compound.

EXAMPLE 129
hexahydro-7-[(3-phenylisoxazol-5-yl)methyl]-1H-azepin-2-one

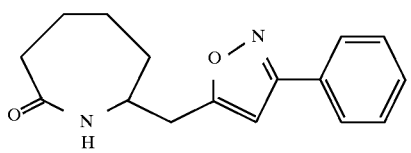

The title Isomer-B material of Example 125 is reacted with manganese dioxide in benzene/dioxane by the method of A. Barco, *Synth. Commun.* 1978, 8, 219, to generate the title compound.

EXAMPLE 130
3,4,5,6-tetrahydro-7-methoxy-2-[(3-phenylisoxazol-5-yl)methyl]-2H-azepine

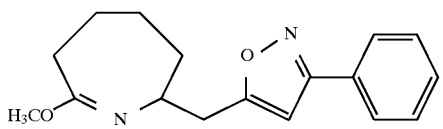

The product of Example 129 is reacted with trimethyloxonium tetrafluoroborate by the method of Example 3 to generate the title compound.

EXAMPLE 131
hexahydro-7-[(3-phenylisoxazol-5-yl)methyl]-1H-azepin-2-imine, monohydrochloride

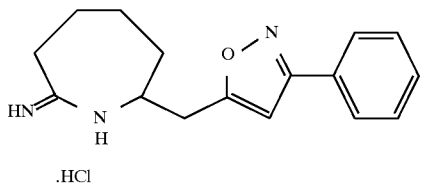

The product of Example 130 is reacted with ammonium chloride by the method of example 5 to generate the title compound.

EXAMPLE 132
7-[[4,5-dihydro-1-phenyl-3-(trifluoromethyl)-1H-pyrazol-5-yl]methyl]hexahydro-1H-azepin-2-one, mixture with 7-[[4,5-dihydro-1-phenyl-3-(trifluoromethyl)-1H-pyrazol-4-yl]methyl]hexahydro-1H-azepin-2-one

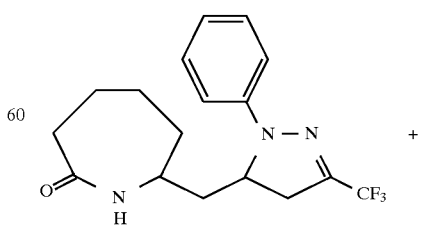

Isomer-A

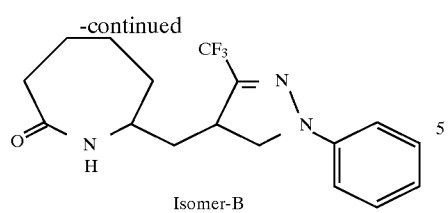

Isomer-B

The title product Isomer B of Example 18 (7-Allyl caprolactam) is reacted with trifluoroacetaldehydebenzene-hydrazonoyl chloride and triethylamine in toluene by the method of R. Huisgen, *Ang. Chem. Int. Ed.* 1963, 2(10), 562, to generate a mixture of the two title compounds. The title Isomer-A and Isomer-B materials are separated by HPLC.

EXAMPLE 133
2-[[4,5-dihydro-1-phenyl-3-(trifluoromethyl)-1H-pyrazol-5-yl]methyl]-3,4,5,6-tetrahydro-7-methoxy-2H-azepine

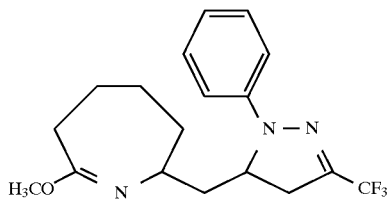

The title Isomer-A material of Example 132 is reacted with trimethyloxonium tetrafluoroborate by the method of Example 3 to generate the title compound.

EXAMPLE 134
7-[[4,5-dihydro-1-phenyl-3-(trifluoromethyl)-1H-pyrazol-5-yl]methyl]-hexahydro-1H-azepin-2-imine, monohydrochloride

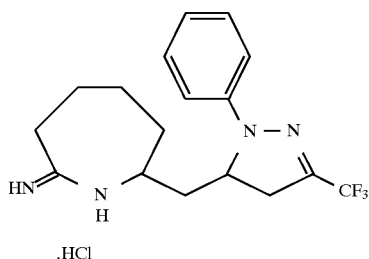

.HCl

The title product of Example 133 is reacted with ammonium chloride by the method of Example 5 to generate the title compound.

EXAMPLE 135
2-[[4,5-dihydro-1-phenyl-3-(trifluoromethyl)-1H-pyrazol-4-yl]methyl]-3,4,5,6-tetrahydro-7-methoxy-2H-azepine

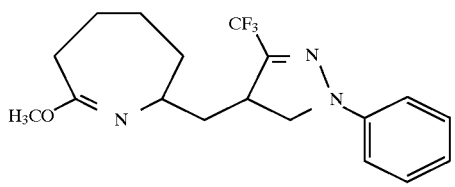

The title Isomer-B material of Example 132 is reacted with trimethyloxonium tetrafluoroborate by the method of Example 3 to generate the title compound.

EXAMPLE 136
7-[[4,5-dihydro-1-phenyl-3-(trifluoromethyl)-1H-pyrazol-4-yl]methyl]hexahydro-1H-azepin-2-imine, monohydrochloride

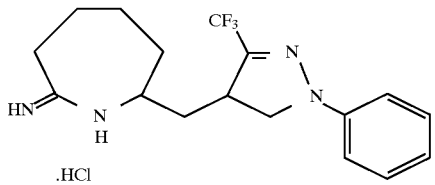

.HCl

The title product of Example 135 is reacted with ammonium chloride by the method of Example 5 to generate the title compound.

EXAMPLE 137
hexahydro-7-[[1-phenyl-3-(trifluoromethyl)-1H-pyrazol-5-yl]methyl]-1H-azepin-2-one

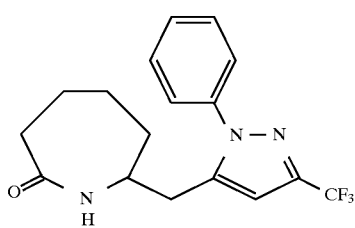

The title Isomer-A material of Example 132 is reacted with DDQ in benzene by the method of E. W. Bousquet, *J. Org. Chem.* 1975, 40, 2208, to generate the title compound.

EXAMPLE 138
3,4,5,6-tetrahydro-7-methoxy-2-[[1-phenyl-3-(trifluoromethyl)-1H-pyrazol-5-yl]methyl]-2H-azepine

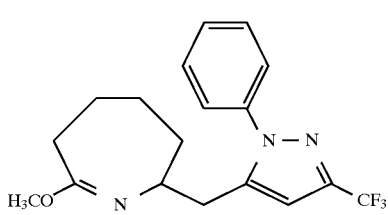

The title material of Example 137 is reacted with trimethyloxonium tetrafluoroborate by the method of Example 3 to generate the title compound.

EXAMPLE 139
hexahydro-7-[[1-phenyl-3-(trifluoromethyl)-1H-pyrazol-5-yl]methyl]-1H-azepin-2-imine, monohydrochloride

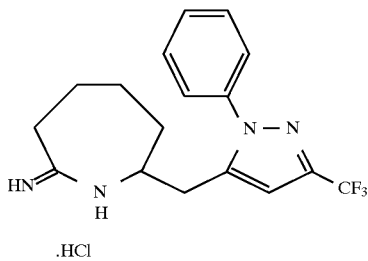

.HCl

The title material of Example 138 is reacted with ammonium chloride by the method of Example 5 to generate the title compound.

EXAMPLE 140 hexahydro-7-[[1-phenyl-3-(trifluoromethyl)-1H-pyrazol-4-yl]methyl]-1H-azepin-2-one The title Isomer-B material of Example 132 is reacted with DDQ in benzene by the method of E. W. Bousquet, *J. Org. Chem.* 1975, 40, 2208, to generate the title compound.

EXAMPLE 141

3,4,5,6-tetrahydro-7-methoxy-2-[[1-phenyl-3-(trifluoromethyl)-1H-pyrazol-4-yl]methyl]-2H-azepine The title material of Example 140 is reacted with trimethyloxonium tetrafluoroborate by the method of Example 3 to generate the title compound.

EXAMPLE 142 hexahydro-7-[[1-phenyl-3-(trifluoromethyl)-1H-pyrazol-4-yl]methyl]-1H-azepin-2-imine, monohydrochloride The title material of Example 141 is reacted with ammonium chloride by the method of Example 5 to generate the title compound.

EXAMPLE 143

7-[(4,5-dihydro-1,3-diphenyl-1H-pyrazol-4-yl)methyl]hexahydro-1H-azepin-2-one, mixture with 7-[(4,5-dihydro-1,3-diphenyl-1H-pyrazol-5-yl)methyl]hexahydro-1H-azepin-2-one Isomer-A

+

Isomer-B

The title product Isomer B of Example 18 (7-Allyl caprolactam) is reacted with benzaldehyde, benzenehydrazonoyl chloride, and triethylamine in toluene by the method of R. Huisgen, *Ang. Chem. Int. Ed.* 1963, 2(10), 562, to generate a mixture of the two title compounds. The title Isomer-A and Isomer-B materials are separated by HPLC.

EXAMPLE 144

2-[(4,5-dihydro-1,3-diphenyl-1H-pyrazol-4-yl)methyl]3,4,5,6-tetrahydro-7-methoxy-2H-azepine The title Isomer-A material of Example 143 is reacted with trimethyloxonium tetrafluoroborate by the method of Example 3 to generate the title compound.

EXAMPLE 145

7-[(4,5-dihydro-1,3-diphenyl-1H-pyrazol-4-yl)methyl]hexahydro-1H-azepin-2-imine, monohydrochloride The title material of Example 144 is reacted with ammonium chloride by the method of Example 5 to generate the title compound.

EXAMPLE 146

7-[(1,3-diphenyl-1H-pyrazol-5-yl)methyl]hexahydro-1H-azepin-2-one

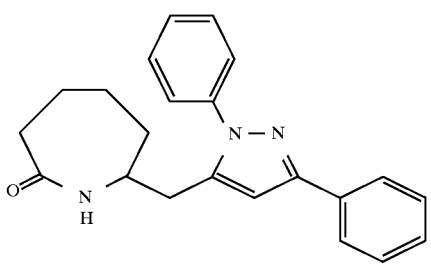

The title Isomer-B material of Example 143 is reacted with DDQ in benzene by the method of E. W. Bousquet, *J. Org. Chem.* 1975, 40, 2208, to generate the title compound.

EXAMPLE 147
2-[(1,3-diphenyl-1H-pyrazol-5-yl)methyl]-3,4,5,6-tetrahydro-7-methoxy-2H-azepine

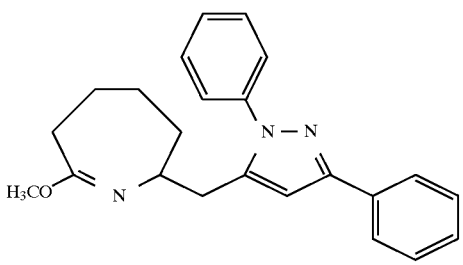

The title product of Example 146 is reacted with trimethyloxonium tetrafluoroborate by the method of Example 3 to generate the title compound.

EXAMPLE 148
7-[(1,3-diphenyl-1H-pyrazol-5-yl)methyl]hexahydro-1H-azepin-2-imine, monohydrochloride

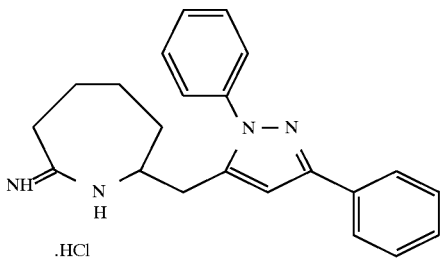

The title material of Example 147 is reacted with ammonium chloride by the method of Example 5 to generate the title compound.

EXAMPLE 149
2-oxocyclohexaneacetonitrile

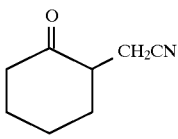

Cyclohexanone is reacted with bromoacetonitrile by the method of Example 65 to generate the title compound.

EXAMPLE 150
2-(hydroxyimino)cyclohexaneacetonitrile

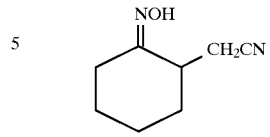

The product of Example 149 is reacted with hydroxylamine hydrochloride and sodium acetate in ethanol/water by the method of Example 1 to generate the title compound.

EXAMPLE 151
hexahydro-7-oxo-1H-azepine-2-acetonitrile

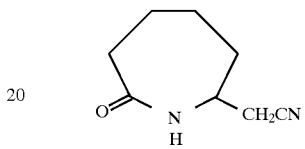

The product of Example 150 is reacted with benzenesulfonyl chloride and sodium hydroxide in acetone/water by the method of Example 67 to generate the title compound.

EXAMPLE 152
hexahydro-7-[[1-phenyl-3-(trifluoromethyl)-1H-1,2,4-triazol-5-yl]methyl]-1H-azepin-2-one

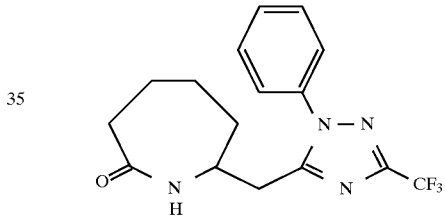

The product of Example 151 is reacted with trifluoroacetaldehyde, benzenehydrazonoyl chloride, and triethylamine in toluene by the method of R. Huisgen, *Ang. Chem. Int. Ed.* 1963, 2(10), 562, to generate the title compound.

EXAMPLE 153
3,4,5,6-tetrahydro-7-methoxy-2-[[1-phenyl-3-(trifluoromethyl)-1H-1,2,4-triazol-5-yl]methyl]-2H-azepine

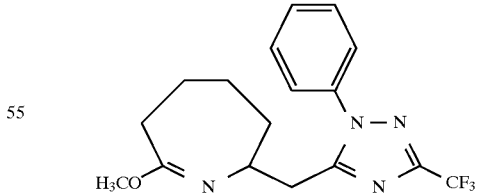

The product of Example 152 is reacted with trimethyloxonium tetrafluoroborate by the method of Example 3 to generate the title compound.

EXAMPLE 154
hexahydro-7-[[1-phenyl-3-(trifluoromethyl)-1H-1,2,4-triazol-5-yl]methyl]-1H-azepin-2-imine, monohydrochloride

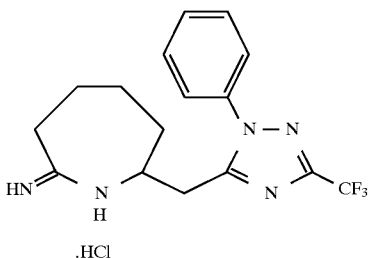

The product of Example 153 is reacted with ammonium chloride by the method of Example 5 to generate the title compound.

EXAMPLE 155
hexahydro-7-[2-(2-nitrophenyl)ethenyl]-1H-azepin-2-one

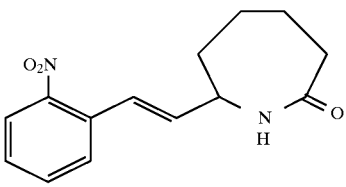

The Isomer A title material of Example 78 in acetonitrile is coupled to 1-bromo-2-nitrobenzene (Aldrich) in the presence palladium acetate, tri-o-tolylphosphine, and triethylamine by the method of Example 32 to provide the title material as either or both the Z and E isomers.

EXAMPLE 156
3,4,5,6-tetrahydro-7-methoxy-2-[2-(2-nitrophenyl)ethenyl]-2H-azepine

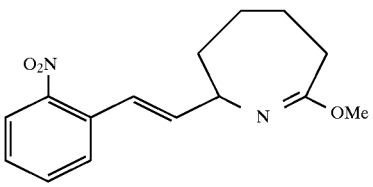

The product of Example 155 is reacted with trimethyloxonium tetrafluoroborate in CH$_2$Cl$_2$ by the method of Example 3 to produce the title material.

EXAMPLE 157
hexahydro-7-[2-(2-nitrophenyl)ethenyl]-1H-azepin-2-imine, monohydrochloride

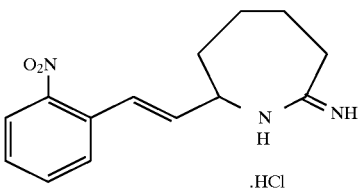

The product of Example 156 is reacted with ammonium chloride by the method of Example 5 to generate the title compound.

EXAMPLE 158
2-[2-(hexahydro-7-imino-2H-azepin-2-yl)ethyl]benzenamine, dihydrochloride

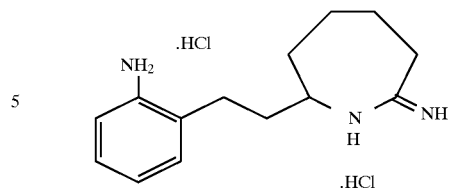

The title material of Example 157 in MeOH is hydrogenated over Pd on carbon in a standard Parr apparatus by the method of Example 35 reducing both the nitro and double bond functions to generate the title product.

EXAMPLE 159
methyl 2-[3-(hexahydro-7-oxo-1H-azepin-2-yl)-1-propenyl]-5-nitrobenzoate

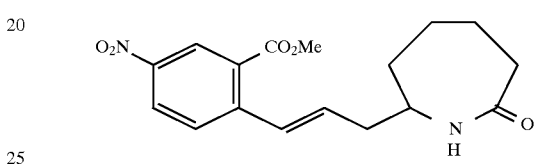

The Isomer B title material of Example 18 in acetonitrile is coupled to methyl-2-bromo-5-nitrobenzoate (Aldrich) in the presence of palladium acetate, tri-o-tolylphosphine, and triethylamine by the method of Example 32 to provide the title material as either or both the Z and E isomers.

EXAMPLE 160
methyl 5-nitro-2-[3-(3,4,5,6-tetrahydro-7-methoxy-2H-azepin-2-yl)-1-propenyl]benzoate

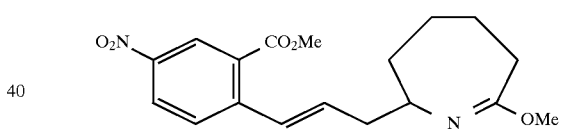

The product of Example 159 is reacted with trimethyloxonium tetrafluoroborate in CH$_2$Cl$_2$ by the method of Example 3 to produce the title material.

EXAMPLE 161
methyl 2-[3-(hexahydro-7-imino-1H-azepin-2-yl)-1-propenyl]-5-nitrobenzoate, monohydrochloride

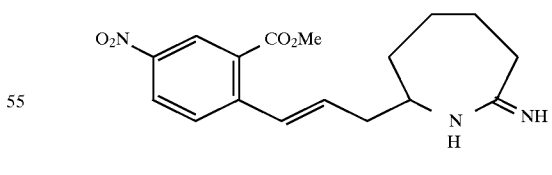

The product of Example 160 is reacted with ammonium chloride by the method of Example 5 to generate the title compound.

EXAMPLE 162
methyl 5-amino-2-[3-(hexahydro-7-imino-1H-azepin-2-yl)-1-propenyl]benzoate, dihydrochloride

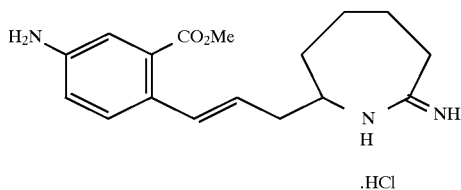

The title material of Example 161 in MeOH is hydrogenated over Pd on carbon in a standard Parr apparatus by the method of Example 35 selectively reducing the nitro function to generate the title product.

EXAMPLE 163
hexahydro-7-[2-(3-methoxyphenyl)ethenyl]-1H-azepin-2-one

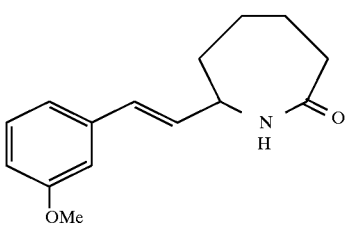

The Isomer A title material of Example 78 in acetonitrile is coupled to 3-bromo-anisole (Aldrich) in the presence palladium acetate, tri-o-tolylphosphine, and triethylamine by the method of Example 32 to provide the title material as either or both the Z and E isomers.

EXAMPLE 164
3,4,5,6-tetrahydro-7-methoxy-2-[2-(3-methoxyphenyl)ethenyl]-2H-azepine

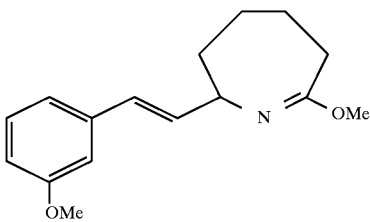

The product of Example 163 is reacted with trimethyloxonium tetrafluoroborate in $CH_2Cl_2$ by the method of Example 3 to produce the title material.

EXAMPLE 165
hexahydro-7-[2-(3-methoxyphenyl)ethenyl]-1H-azepin-2-imine, monohydrochloride

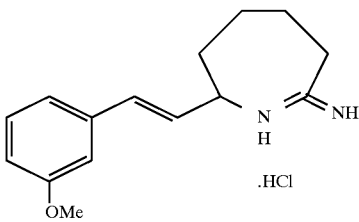

The product of Example 164 is reacted with ammonium chloride by the method of Example 5 to generate the title compound.

EXAMPLE 166
hexahydro-7-[2-(3-methoxyphenyl)ethyl]-1H-azepin-2-one

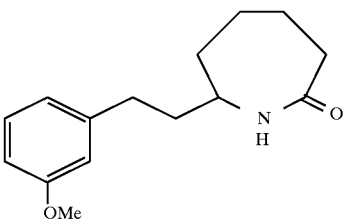

The title material of Example 163 in MeOH is hydrogenated over Pd on carbon in a standard Parr apparatus by the method of Example 35 to generate the title product.

EXAMPLE 167
3,4,5,6-tetrahydro-7-methoxy-2-[2-(3-methoxyphenyl)ethyl]-2H-azepine

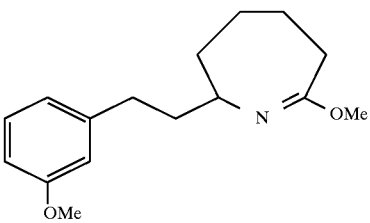

The product of Example 166 is reacted with trimethyloxonium tetrafluoroborate in $CH_2Cl_2$ by the method of Example 3 to produce the title material.

EXAMPLE 168
hexahydro-7-[2-(3-methoxyphenyl)ethyl]-1H-azepin-2-imine, monohydrochloride

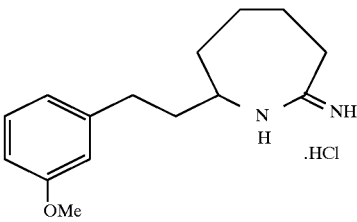

The product of Example 167 is reacted with ammonium chloride by the method of Example 5 to generate the title compound.

EXAMPLE 169
7-[2-(3-furanyl)ethenyl]hexahydro-1H-azepin-2-one

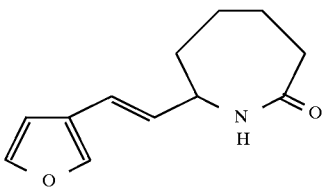

The Isomer A title material of Example 78 in acetonitrile is coupled to 3-bromo-furan (Aldrich) in the presence palladium acetate, tri-o-tolylphosphine, and triethylamine by the method of Example 32 to provide the title material as either or both the Z and E isomers.

EXAMPLE 170
7-[2-(3-furanyl)ethyl]hexahydro-1H-azepin-2-one

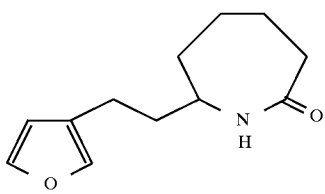

The title material of Example 169 in MeOH is hydrogenated over Pd on carbon in a standard Parr apparatus by the method of Example 35 to generate the title product.

EXAMPLE 171
3,4,5,6-tetrahydro-2-[2-(3-furanyl)ethyl]-7-methoxy-2H-azepine

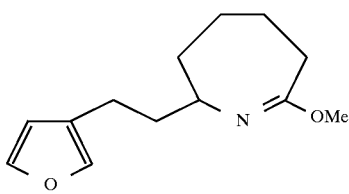

The product of Example 170 is reacted with trimethyloxonium tetrafluoroborate in $CH_2Cl_2$ by the method of Example 3 to produce the title material.

EXAMPLE 172
7-[2-(3-furanyl)ethyl]hexahydro-1H-azepin-2-imine, monohydrochloride

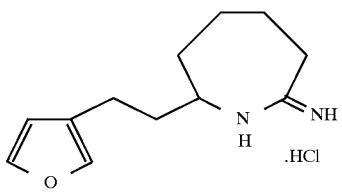

The product of Example 171 is reacted with ammonium chloride by the method of Example 5 to generate the title compound.

EXAMPLE 173
hexahydro-7-[2-(2-thienyl)ethenyl]-1H-azepin-2-one

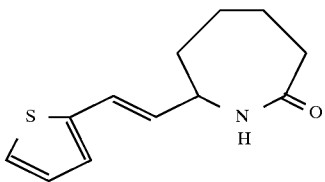

The Isomer A title material of Example 78 in acetonitrile is coupled to 2-bromothiophene (Aldrich) in the presence of palladium acetate, tri-o-tolylphosphine, and triethylamine by the method of Example 32 to provide the title material as either or both the Z and E isomers.

EXAMPLE 174
3,4,5,6-tetrahydro-7-methoxy-2-[2-(2-thienyl)ethyl]-2H-azepine

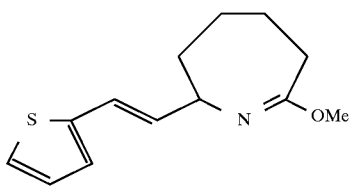

The product of Example 173 is reacted with trimethyloxonium tetrafluoroborate in $CH_2Cl_2$ by the method of Example 3 to produce the title material.

EXAMPLE 175
hexahydro-7-[2-(2-thienyl)ethenyl]-1H-azepin-2-imine, monohydrochloride

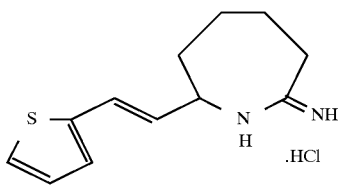

The product of Example 175 is reacted with ammonium chloride by the method of Example 5 to generate the title compound.

EXAMPLE 176
hexahydro-7-[2-(2-thienyl)ethyl]-1H-azepin-2-imine, monohydrochloride

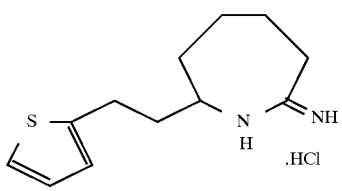

The title material of Example 175 in EtOH is hydrogenated over 10% Pd on carbon catalyst in a standard Parr apparatus by the method of Example 35 to generate the title product.

EXAMPLE 177
methyl 5-[3-(hexahydro-7-oxo-1H-azepin-2-yl)-1-propenyl]furan-2-carboxylate

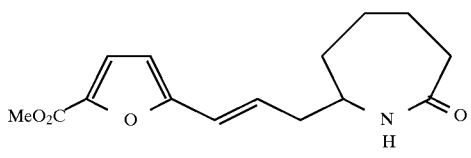

The Isomer B title material of Example 18 in acetonitrile is coupled to methyl 5-bromo-furanate, prepared from 5-bromofuroic acid (Aldrich) and thionyl chloride in methanol, in the presence of palladium acetate, tri-o-tolylphosphine, and triethylamine by the method of Example 32 to provide the title material as either or both the Z and E isomers.

EXAMPLE 178
methyl 5-[3-(3,4,5,6-tetrahydro-7-methoxy-2H-azepin-2-yl)-1-propenyl]furan-2-carboxylate

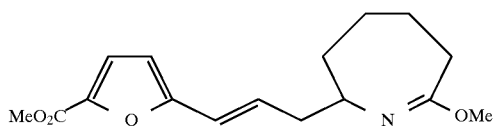

The product of Example 177 is reacted with trimethyloxonium tetrafluoroborate in $CH_2Cl_2$ by the method of Example 3 to produce the title material.

EXAMPLE 179
methyl 5-[3-(hexahydro-7-imino-1H-azepin-2-yl)-1-propenyl]furan-2-carboxylate, monohydrochloride

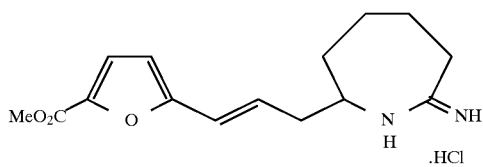

The product of Example 178 is reacted with ammonium chloride by the method of Example 5 to generate the title compound.

EXAMPLE 180
methyl 5-[3-(hexahydro-7-imino-1H-azepin-2-yl)propyl]furan-2-carboxylate, monohydrochloride

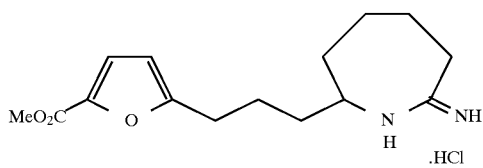

The title material of Example 179 in EtOH is hydrogenated over 10% Pd on carbon catalyst in a standard Parr apparatus by the method of Example 35 to generate the title product.

EXAMPLE 181
hexahydro-7-[2-(2-thiazolyl)ethenyl]-1H-azepin-2-one

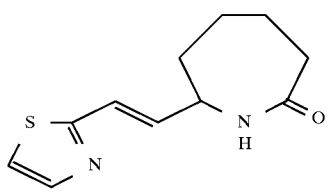

The Isomer B title material of Example 18 in acetonitrile is coupled to 2-bromothiazole (Aldrich) in the presence of palladium acetate, tri-o-tolylphosphine, and triethylamine by the method of Example 32 to provide the title material as either or both the Z and E isomers.

EXAMPLE 182
3,4,5,6-tetrahydro-7-methoxy-2-[2-(2-thiazolyl)ethenyl]-2H-azepine

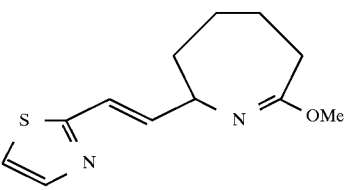

The product of Example 181 is reacted with one equivalent of trimethyloxonium tetrafluoroborate in $CH_2Cl_2$ by the method of Example 3 to produce a mixture of the title material and the N-methylated thiazolium salt which is isomerized on heating to the title material.

EXAMPLE 183
hexahydro-7-[2-(2-thiazolyl)ethenyl]-1H-azepin-2-imine, monohydrochloride

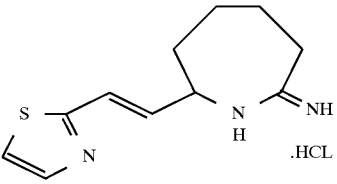

The product of Example 182 is reacted with ammonium chloride by the method of Example 5 to generate the title compound.

EXAMPLE 184
hexahydro-7-[2-(2-thiazolyl)ethyl]-1H-azepin-2-imine, monohydrochloride

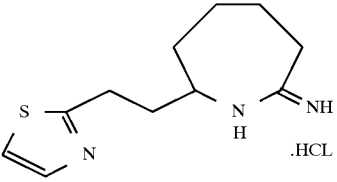

The title material of Example 183 in EtOH is hydrogenated over 10% Pd on carbon catalyst in a standard Parr apparatus by the method of Example 35 to generate the title product.

EXAMPLE 185
1,1-dimethylethyl hexahydro-2-oxo-7-(phenylmethyl)-1H-azepine-1-carboxylate

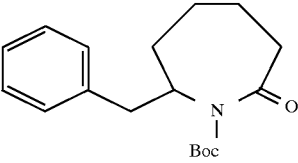

To the Isomer-A title product of Example 2 in dry THF maintained under an Ar atmosphere is added dimethylaminopyridine (DMAP). di-t-butyl dicarbonate in THF is then added and the reaction mixture is brought to reflux. After cooling the reaction to room temperature, all solvent is removed under reduced pressure and the title material is isolated by HPLC.

EXAMPLE 186
1.1-dimethylethyl hexahydro-2-oxo-7(phenylmethyl)-3-(phenylseleno)-1H-azepine-1-carboxylate

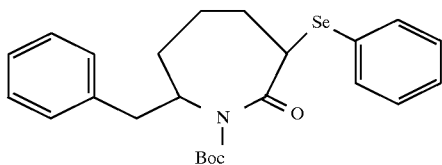

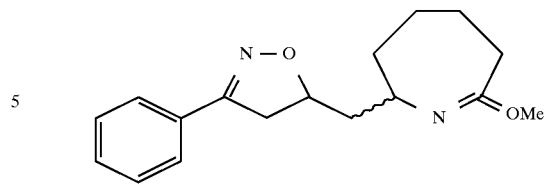

To a stirring solution of the product of Example 185 in THF at −78° C. is added lithium hexamethyldisilazide also in THF. After stirring the solution at −78° C., benzeneselenyl chloride is added. The reaction is stirred cold, warmed to room temperature and stirred at this temperature. The mixture is then diluted with Et$_2$O, partitioned between water and brine, and the title product isolated from the organic layer by HPLC.

EXAMPLE 187

1,5,6,7-tetrahydro-7-(phenylmethyl)-2H-azepin-2-one

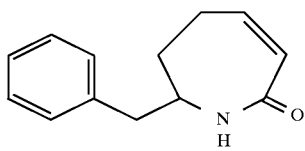

187 A) The product of Example 186 in THF is treated with 30% hydrogen peroxide (H$_2$O$_2$). All solvent is removed under reduced pressure and the unsaturated product, 1,1-dimethylethyl 1,5,6,7-tetrahydro-2-oxo-7-(phenylmethyl)-2H-azepine-1-carboxylate, is purified by HPLC methods. 187) The Boc protected product of this Example part A is dissolved in acetic acid and treated with a 4N solution of HCl in dioxane. All solvent is removed under reduced pressure and the title material purified by HPLC methods.

EXAMPLE 188

3,4-dihydro-7-methoxy-2-(phenylmethyl)-2H-azepine

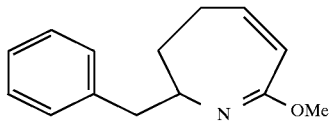

The product of Example 187 is reacted with one equivalent of trimethyloxonium tetrafluoroborate in CH$_2$Cl$_2$ by the method of Example 3 to produce the title material.

EXAMPLE 189

1,5,6,7-tetrahydro-7-(phenylmethyl)-2H-azepin-2-imine, monohydrochloride

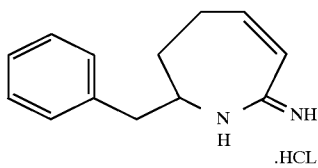

The product of Example 188 is reacted with ammonium chloride by the method of Example 5 to generate the title compound.

EXAMPLE 190

2-[(4,5-dihydro-3-phenylisoxazolyl-5-yl)methyl]-3,4,5,6-tetrahydro-7-methoxy-2H-azepine To a magnetically stirred slurry of trimethyloxonium tetrafluoroborate (Sigma, 0.13 g, 0.9 mmol) and CH$_2$Cl$_2$ (10 mL) under nitrogen (N$_2$) was added the Isomer-B product of Example 125 (0.22 g, 0.81 mmol). This mixture was stirred at room temperature for 18 hours before it was diluted with 30 mL of EtOAc and partitioned between the organic layer and 40 mL of saturated NaHCO$_3$. The organic phase was separated, dried over MgSO$_4$, filtered, and stripped of all solvent under reduced pressure to provide 0.17 g (73%) of the crude title product as a pale yellow oil. This material was used as is in subsequent Example 191.

EXAMPLE 191

7-[(4,5-dihydro-3-phenylisoxazolyl-5-yl)methyl] hexahydro-1H-azepine-2-imine, monotrifluoroacetic acid salt

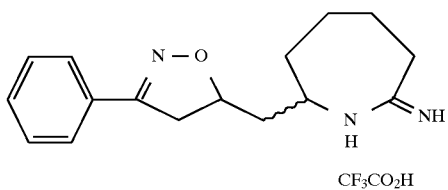

The title product of Example 190 (0.17 g, 0.6 mmol) and 0.035 g (0.65 mmol) of NH$_4$Cl were refluxed in 10 mL of MeOH under a N$_2$ atmosphere for 18 h. After cooling the reaction to room temperature, it was filtered and partitioned between 15 mL of water and 7 mL of EtOAc. The organic and aqueous phases were separated and the aqueous phase was extracted with a 15 mL portion of EtOAc before it was lyophilized to provide 0.13 g (71%) of an orange solid material. Chromatography of 0.1 g on a preparatory C-18 column eluting with acetonitrile/water afforded after lyophilization from trifluoroacetic acid (TFA)/water 0.04 g of the title compound as an off-white solid material.

1H NMR(D$_2$O): d 7.6 (d, 2H), 7.4 (m, 3H), 4.85 (m, 1H), 3.75 (m, 1H), 3.6 (dd, 1H), 3.15 (dd, 1H) 2.65 (m, 1H), 2.5 (m, 1H), 2.0–1.3 (m, 8H). M+H=272.

EXAMPLE 192

The following functionalized aromatic methyl halides and equivalents are reacted with cyclohexanone by the process described in Example 65. The resulting 2-[(substituted aromatic)methyl]cyclohexanone is treated with hydroxylamine as described in Example 1 to yield the corresponding oxime, which is then treated as described in Example 2 to give a mixture of 3- and 7-substituted caprolactams. They are separated as also described in Example 2, and then individually treated as described in Example 3 to yield the corresponding imino ether. This imino ether is treated with ammonium chloride in methanol as described in Example 5 to give the desired product amidines:

| STARTING HALIDE | CORRESPONDING PRODUCT |
|---|---|
| a-bromo-2,6-dichlorotoluene | 7-[(2,6-dichlorophenyl)methyl]-hexahydro-1H-azepin-2-imine |
| a-bromo-4-fluorotoluene | 7-[(4-fluorophenyl)methyl]hexa-hydro-1H-azepin-2-imine |
| a-bromo-2,4-difluorotoluene | 7-[(2,4-difluorophenyl)methyl]-hexahydro-1H-azepin-2-imine |
| a-bromo-2,3,4,5,6-pentafluoro-toluene | 7-[(2,3,4,5-pentafluorophenyl)-methyl]hexahydro-1H-azepin-2-imine |
| a-bromo-4-trifluoromethyl-toluene | hexahydro-7-[[4-(trifluoro-methyl)phenyl]methyl]-1H-azepin-2-imine |
| a-bromo-3-trifluoromethyl-toluene | hexahydro-7-[[3-(trifluoro-methyl)phenyl]methyl]-1H-azepin-2-imine |
| 2-(bromomethyl)biphenyl | 7-[(2-biphenylyl)methyl]hexa-hydro-1H-azepin-2-imine |
| a-bromo-2-nitrotoluene | hexahydro-7-[(2-nitrophenyl)-methyl]-1H-azepin-2-imine |
| a-bromo-4-nitrotoluene | hexahydro-7-[(4-nitrophenyl)-methyl]-1H-azepin-2-imine |
| a-bromo-4-carboxymethyl-toluene | 4-[(hexahydro-7-imino-1H-azepin-2-yl)methyl]benzene-acetic acid |
| 2-chloro-5-chloromethyl-thiophene | 7-[(5-chlorothien-2-yl)methyl]-hexahydro-1H-azepin-2-imine |
| 4-chloromethyl-3,5-dimethyl-isoxazole | 7-[(3,5-dimethylisoxazol-4-yl)methyl]hexahydro-1H-azepin-2-imine |

EXAMPLE 193

2-[(tetrahydro-2H-pyran-2-yl)methyl]cyclohexanol

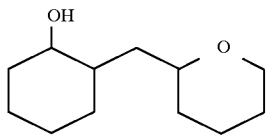

To a stirring THF solution of the Grignard reagent (formed from 2-(bromomethyl)tetrahydro-2H-pyran, 16 mmol, and powdered magnesium, 20 milligram-atoms) and cooled to −30° C., CuI is added as a bolus. After approx. 10 min., a solution of cyclohexene oxide (10 mmol) is added slowly, maintaining the reaction temperature below −25° C. until the addition is complete. The mixture is then stirred at 0° C. for 2 hours and checked by TLC and/or GC. The reaction is quenched by pouring into concentrated NH$_4$Cl solution (if starting material remains, the reaction may be warmed to r.t. and followed by TLC or GC until no additional starting material is observed). Also, the addition of some concentrated NH$_4$OH solution combined with vigorous stirring may be used to remove suspended CuI from the mixture. This mixture is then extracted with 2 portions of ether or 1:1 EA-hexane. The combined extracts are then washed with brine and dried (MgSO$_4$). The product may be sufficiently pure at this point for use in the next reaction. Otherwise, it may be purified by distillation or flash chromatography.

EXAMPLE 194

2-[(tetrahydro-2H-pyran-2-yl)methyl]cyclohexanone

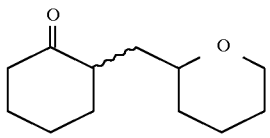

Neat, dry DMSO (4 equivalents) is added slowly to a CH$_2$Cl$_2$ solution of the oxalyl chloride (1.25 equivalents) cooled to −70° C. under N$_2$. After stirring for about 15 min., the product of Example 193 (1 equivalent) in CH$_2$Cl$_2$ is added slowly. Neat triethylamine (4 equivalents) is then added and the mixture is warmed to 0° C. After 30 min., the mixture is poured into stirred ice-water and neutralized with dilute HCl. The mixture is then separated and the aqueous layer extracted with CH$_2$Cl$_2$. The organic extracts are then combined, washed with dilute brine, dried (MgSO$_4$) and stripped of all solvent under reduced pressure. The crude title compound is purified by column chromatography.

EXAMPLE 195 hexahydro-7-[(tetrahydro-2H-pyran-2-yl)methyl]-1H-azepin-2-imine

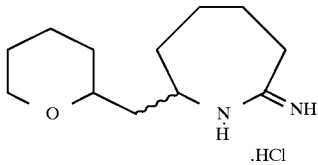

The product of Example 194 is converted to the corresponding oxime by the methods taught in Example 39, and then to the corresponding mixture of lactams as taught in Example 67. The mixture of lactams is separated as also described in Example 67. The resulting 3-substituted caprolactam is reserved for use as described in Example 196 (vide infra), and the 7-substituted caprolactam is treated with trimethyloxonium tetrafluoroborate as described in Example 3 to give the corresponding imino ether. This imino ether is treated with NH$_4$Cl in methanol as described in Example 5 to give the title compound.

EXAMPLE 196 hexahydro-3-[(tetrahydro-2H-pyran-2-yl)methyl]-1H-azepin-2-imine

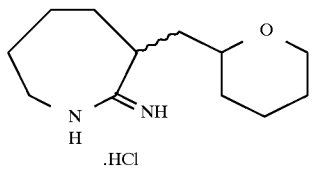

The 3-[(2-tetrahydropyanyl)methyl]caprolactam isolated in Example 195 is treated as described in Example 3 to give the corresponding imino ether, and then with NH$_4$Cl in methanol as described in Example 5 to give the title compound.

EXAMPLE 197

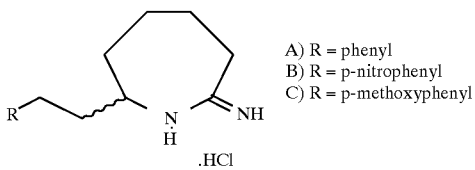

A) R = phenyl
B) R = p-nitrophenyl
C) R = p-methoxyphenyl

The aromatic ethyl halides listed below as STARTING HALIDE are reacted with cyclohexene oxide by the process described in Example 193. The resulting 2-(aromatic-ethyl) cyclohexanols are then oxidized to the respective 2-(aromatic-ethyl) cyclohexanones by the method of Example 194. The 2-(aromatic-ethyl) cyclohexanones are treated with hydroxylamine as taught in Example 1 to yield the corresponding oxime, which is then treated as described in Example 2 to give a mixture of 3- and 7-substituted caprolactams. This mixture is separated also as described in Example 2, and then individually treated as taught in Example 3 to yield the corresponding imino ether. The imino ethers are treated with ammonium chloride in methanol as described in Example 5 to give the desired product amidines described below:

| STARTING HALIDE | CORRESPONDING PRODUCT |
| --- | --- |
| A) (2-bromoethyl)benzene | hexahydro-7-(2-phenylethyl)-1H-azepin-2-imine, monohydrochloride |
| B) (2-bromoethyl)-4-nitrobenzene | hexahydro-7-[2-(4-nitrophenyl)1H-azepin-2-imine, monohydrochloride |
| C) (2-bromoethyl)-4-methoxybenzene | hexahydro-7-[2-(4-methoxyphenyl ethyl]-1H-azepin-2-imine, monohydrochloride |

EXAMPLE 198
7-[3-[5-(1,3-dioxolan-2-yl)thien-2-yl)-2-propenyl] hexahydro-1H-azepin-2-imine, monohydrochloride

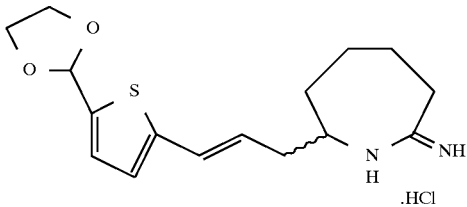

198 A) The Isomer B title material of Example 18 in acetonitrile is coupled to 2-(5-bromo-2-thienyl)dioxolane in the presence palladium acetate, tri-o-tolylphosphine, and triethylamine by the method of Example 32 to provide 7-[3-[5-(1,3-dioxolan-2-yl)thien-2-yl]-2-propenyl] hexahydro-1H-azepin-2-one as primarily the E isomer.

198 B) The product of part A above is reacted with trimethyloxonium tetrafluoroborate by the method of Example 67 to yield imino ether, 2-[3-[5-(1,3-dioxolan-2-yl)thien-2-yl]propyl]-3,4,5,6-tetrahydro-7-methoxy-2H-azepine.

198) the crude product of part B above is reacted with ammonium chloride in methanol by the method of Example 5 to give the title material after reverse phase chromatographic purification.

EXAMPLE 199
5-[3-(hexahydro-7-imino-1H-azepin-2-yl)-1-propenyl] thiophene-2-carboxamide, monohydrochloride

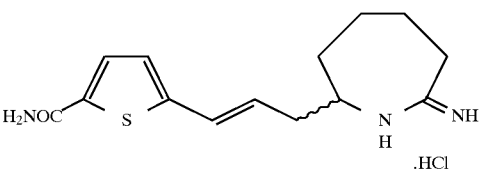

199 A) A sample of the product of part A, Example 198, 7-[3-[5-(1,3-dioxolan-2-yl)thien-2-yl]-2-propenyl] hexahydro-1H-azepin-2-one, is treated with dilute HCl to generate aldehyde, 5-[3-(hexahydro-7-oxo-1H-azepin-2-yl)-1-propenyl]thiophene-2-carboxaldehyde.

199 B) The product of this Example, part A above, is oxidized to 5-[3-(hexahydro-7-oxo-1H-azepin-2-yl)-1-propenyl]thiophene-2-carboxylic acid using potassium permanganate solubilized in benzene with dicyclohexyl-18-crown-6 by the method described by D. J. Sam et al *J. Am. Chem. Soc.* 1972, 94, 4024.

199 C) To a cold solution of thionyl chloride in methanol is added the product of this Example, part B above. The product methyl ester, methyl 5-[3-(hexahydro-7-oxo-1H-azepin-2-yl)-1-propenyl]thiophene-2-carboxylate, is isolated after quenching the reaction with KHCO₃, extracting with EtOAc, and purifying by column chromatography.

199 D) The product of this Example, part C above, is reacted with trimethyloxonium tetrafluoroborate by the method of Example 67 to yield imino ether, methyl 5-[3-(3,4,5,6-tetrahydro-7-methoxy-2H-azepin-2-yl)-1-propenyl] thiophene-2-carboxylate.

199 E) The crude product of this Example, part D above, is reacted with ammonium chloride in methanol by the method of Example 5 to give the amidine, methyl 5-[3-(hexahydro-7-imino-1H-azepin-2-yl)-1-propenyl] thiophene-2-carboxylate, monohycrochloride.

199 F) The product of this Example, part E above, is hydrolyzed to its free acid, 5-[3-(hexahydro-7-imino-1H-azepin-2-yl)-1-propenyl]thiophene-2-carboxylic acid, monohydrochloride using HCl.

199) The product of this Example, part F above, is reacted with isobutylchloroformate in the presence of N-methylmorpholine followed by ammonium chloride to provide the title product after reverse phase chromatographic purification.

EXAMPLE 200
methyl 2-[3-(hexahydro-7-imino-1H-azepin-2-yl)-1-propenyl]-5-methoxybenzoate, monohydrochloride

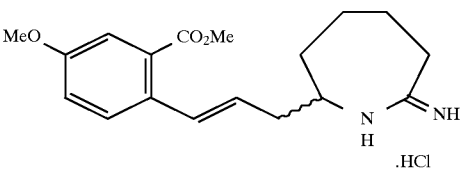

200 A) The Isomer B title material of Example 18 in acetonitrile is coupled to methyl 2-bromo-5-methoxybenzoate in the presence of palladium acetate, tri-o-tolylphosphine, and triethylamine by the method of Example 32 to provide methyl 2-[3-(hexahydro-7-oxo-1H-azepin-2-yl)-1-propenyl]-5-methoxybenzoate as primarily its E isomer.

200 B) The product of this Example, part A above, is reacted with trimethyloxonium tetrafluoroborate by the method of Example 67 to yield imino ether, methyl 2-[3-(3,4,5,6- tetrahydro-7-methoxy-2H-azepin-2-yl)-1-propenyl]-5-methoxybenzoate.

200) The crude product of this Example, part B above, is reacted with ammonium chloride in methanol by the method of Example 5 to give the title material after reverse phase chromatographic purification.

EXAMPLE 201 b-(2-oxocyclohexyl)-4-methylbenzenepropanoic acid

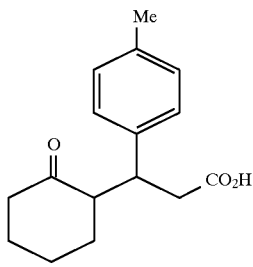

1-pyrrolidino-1-cyclohexene is refluxed with methyl a-(2-oxocyclohexyl)benzenepropanoate in dimethylformamide (DMF) for 24 hours and refluxing is continued for another hour after the addition of water. DMF is removed under reduced pressure and the residue is diluted with water and extracted three times with EtOAc. The combined EtOAc extracts are washed with 1N HCl and then with brine. The organic phase is dried over $MgSO_4$ and evaporated to give crude methyl b-(2-oxocyclohexyl)-4-methylbenzenepropanoate. This material is treated with 1N LiOH/methanol to give the title material.

EXAMPLE 202

Isomer A: hexahydro-b-(4-methylphenyl)-7-oxo-1H-azepine-2-propanoic acid
Isomer B: hexahydro-b-(4-methylphenyl)-2-oxo-1H-azepine-3-propanoic acid

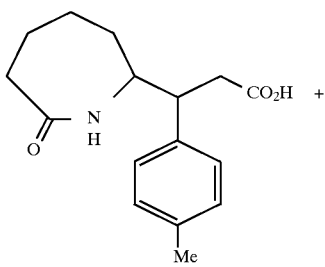

Isomer A

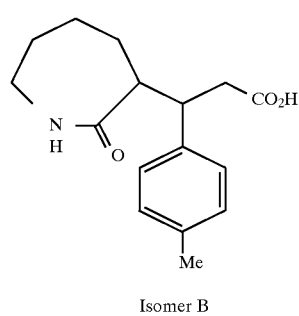

Isomer B

The title material of Example 201 in formic acid is added to a solution of hydroxylamine-O-sulfonic acid in formic acid over a 5 min. period with stirring under $N_2$. The mixture is heated under reflux for 3 hours and then cooled to room temperature. The reaction is quenched with cold water and the solution is neutralized with 6N NaOH. It is then extracted three times with $CH_2Cl_2$. The combined organic layers are dried over $MgSO_4$ and the solvent is removed on a rotary evaporator. The desired products are purified and isolated by HPLC to give both the 3- and 7-substituted title products.

EXAMPLE 203

Isomer A: methyl hexahydro-7-imino-b-(4-methylphenyl)-1H-azepine-2-propanoate, monohydrochloride Isomer B: methyl hexahydro-2-imino-b-(4-methylphenyl)-1H-azepine-3-propanoate, monohydrochloride

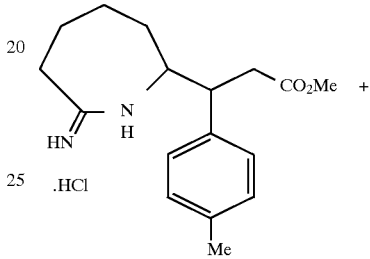

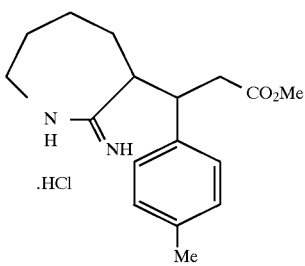

Each of the title caprolactams of Example 202 is independently treated as described in Example 3 to yield the corresponding imino ethers. The imino ethers are then treated with ammonium chloride in methanol as described in Example 5 to give the desired amidines.

EXAMPLE 204

The following activated vinyl derivatives are reacted with 1-pyrrolidino-1-cyclohexene following the method described in Example 201. The resulting 2-substituted cyclohexanone is treated with a solution of hydroxylamine-O-sulfonic acid in formic acid as described in Example 202 to give a mixture of 3- and 7-substituted caprolactams. These lactams are treated as described in Example 3 to yield the corresponding imino ether. This imino ether is treated with ammonium chloride in methanol as described in Example 5 to give the desired amidine products illustrated below.

204 a) methyl 3-[4-(trifluoromethyl)phenyl]propenoate
methyl hexahydro-7-imino-b-[4-(trifluoromethyl)phenyl]-1H-azepine-2-propanoate, monohydrochloride

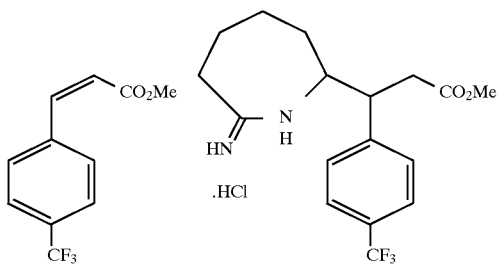

204 b) (2-nitroethenyl)benzene hexahydro-7-(2-nitro-1-phenylethyl)-1H-azepin-2-imine, monohydrochloride

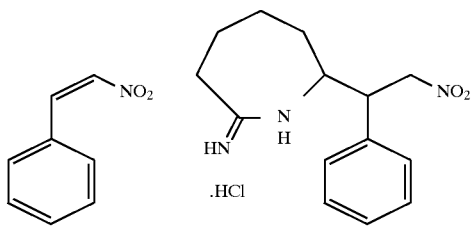

204 c) 3-(2-furanyl)propenenitrile b-(2-furanyl)hexahydro-7-imino-1H-azepine-2-propanenitrile, monohydrochloride

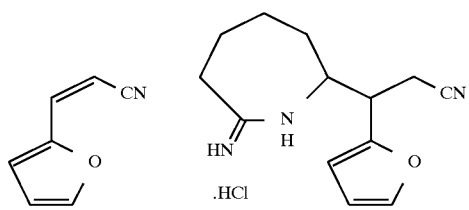

204 d) methyl 3-(2-furanyl)propenoate methyl b-(2-furanyl)hexahydro-7-imino-1H-azepine-2-propanoate, monohydrochloride

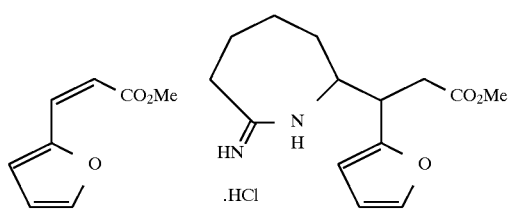

204 e) (ethenylsulfonyl)benzene hexahydro-7-[2-(phenylsulfonyl)ethyl]-1H-azepin-2-imine, monohydrochloride

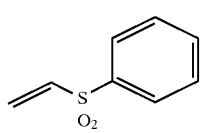

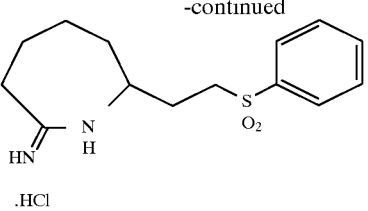

EXAMPLE 205

7-(2-amino-1-phenylethyl) hexahydro-1H-azepin-2-imine, dihydrochloride

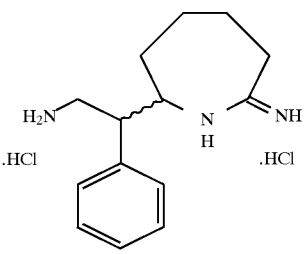

The product of Example 204, reaction B, hexahydro-7-(2-nitro-1-phenylethyl)-1H-azepin-2-imine, monohydrochloride, is reduced with $H_2$ in a standard Parr hydrogenation apparatus using a Pd catalyst on a solid support. This product is treated with dilute HCl, stripped of all solvent under reduced pressure, and lyophilized to produce the title material.

EXAMPLE 206

N-[2-(hexahydro-7-imino-1H-azepin-2-yl)-2-phenylethyl] methanesulfonamide, monohydrochloride

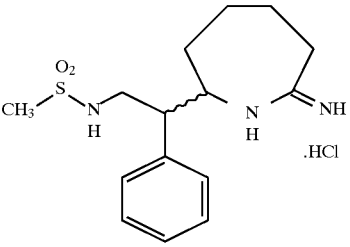

206 A) The nitro function of the 7-substituted lactam generated in Example 204, reaction B, hexahydro-7-(2-nitro-1-phenylethyl)-1H-azepin-2-one, is reduced to an amine, 7-(2-amino-1-phenylethyl) hexahydro-1H-azepin-2-one, monohydrochloride, by the method of Example 205.

206 B) The product of this Example, part A is treated with an equivalent of methanesulfonyl chloride in the presence of triethylamine to yield its sulfonamide derivative, N-[2-(hexahydro-7-oxo-1H-azepin-2-yl)-2-phenyl] methanesulfonamide.

206 C) The sulfonamide material of this Example, part B, is treated with trimethyloxonium tetrafluoroborate (1.5 equivalents) in $CH_2Cl_2$ following the method of Example 3 to give the iminoether intermediate, N-[2-phenyl-2-(3,4,5,6-tetrahydro-7-methoxy-2H-azepin-2-yl)ethyl] methanesulfonamide.

206) The crude product of this Example, part C, is then treated with ammonium chloride in methanol following the method of Example 5 to give the title compound.

EXAMPLE 207 g-(2-furanyl)hexahydro-7-imino-1H-azepine-2-propanamine, dihydrochloride

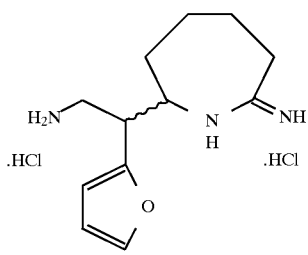

The product of Example 204, reaction C, b-(2-furanyl) hexahydro-7-imino-1H-azepine-2-propanenitrile, monohydrochloride, is reduced with $H_2$ in a standard Parr hydrogenation apparatus using a Pd catalyst on a carbon support by the method described by J. A. Secrist et al *J. Org. Chem.* 1972, 37, 335.

EXAMPLE 208

N-[3-(2-furanyl)-3-(hexahydro-7-imino-1H-azepin-2-yl)propyl]methanesulfonamide, monohydrochloride

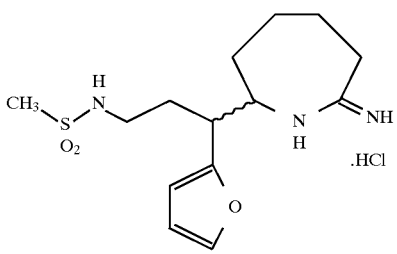

208 A) The cyano function of the 7-substituted lactam generated in Example 204, reaction C, b-(2-furanyl) hexahydro-7-oxo-1H-azepinepropanenitrile, is reduced to its amine, g-(2-furanyl)hexahydro-7-oxo-1H-azepinepropanamine, monohydrochloride, by the method of Example 207.

208 B) The product of this Example, part A is treated with an equivalent of methanesulfonylchloride in the presence of triethylamine to yield its sulfonamide derivative, N-[3-(2-furanyl)-3-(hexahydro-7-oxo-1H-azepin-1-yl)propyl]methanesulfonamide.

208 C) The sulfonamide material of this Example, part B, is treated with trimethyloxonium tetrafluoroborate (1.5 equivalents) in $CH_2Cl_2$ following the method of Example 3 to give the iminoether intermediate, N-[3-(2-furanyl)-3-(hexahydro-7-oxo-1H-azepin-1-yl)propyl]methanesulfonamide.

208) The crude product of this Example, part C, is then treated with ammonium chloride in methanol following the method of Example 5 to give the title compound.

EXAMPLE 209

1,1-dimethylethyl hexahydro-2-(4-methoxy-4-oxo-2-butenyl)-7-oxo-1H-azepine-1-carboxylate

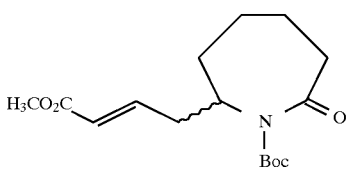

209 A) The title material of Example 18, isomer B, is converted to its Boc derivative, 1,1-dimethylethyl hexahydro-2-oxo-7-(2-propenyl)-1H-azepine-1-carboxylate, by the method of Example 185.

209 B) The Boc allyl lactam of this Example, part A above, is dissolved in $CH_2Cl_2$, cooled to below −70° C., treated with ozone until a persistent blue color is observed. After sparging with oxygen to remove excess ozone, triphenylphosphine (1.5 equivalents) is added and the mixture stirred at 0° C. for 30 minutes and then at room temperature. overnight. The mixture is concentrated and the residue is triturated with several volumes of pentane to remove the phosphorous salts, filtered and stripped to give a crude aldehyde, 1,1-dimethylethyl hexahydro-2-(2-oxoethyl)-7-oxo-1H-azepine-1-carboxylate, which is used without further purification in Part C below.

209) The crude aldehyde of this Example, part B above, is dissolved in toluene and treated with 1.2 equivalents of methyl (triphenylphosphoranylidene)acetate. The mixture is refluxed for four hours. After cooling, the mixture is concentrated and the residue is triturated with several volumes of pentane to remove the phosphorous salts. The extracts are filtered and stripped of all solvent. The crude residue is then purified by column chromatography to give the title product.

EXAMPLE 210 methyl 1-[(1,1-dimethylethoxy)carbonyl]hexahydro-7-oxo-b-(2-propenyl)-1H-azepine-2-butanoate

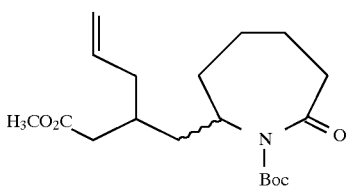

Four equivalents of allyl lithium are added to a stirring suspension of 2 equivalents copper (I) iodide in THF at −50° C. under argon. After the mixtures becomes homogeneous (approx. 20 minutes.), a solution of the title ester of Example 209 (1 equivalent) in THF is added to the cold mixture and stirred below −50° C. for approx. 30 minutes. The mixture is poured into saturated ammonium chloride solution and stirred vigorously for 15 minutes. The mixture is then partitioned between ether and water and the organic layer is washed with water and brine before it is dried ($Na_2SO_4$). The mixture is then filtered and stripped of all solvent. The title material is then purified by column chromatography.

EXAMPLE 211 methyl 7-ethoxy-3,4,5,6-tetrahydro-b-(2-propenyl)-2H-azepine-2-butanoate

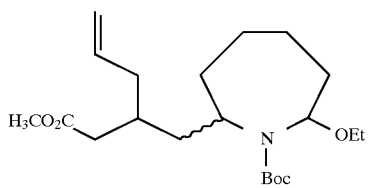

211 A) The Boc group is removed from title compound of Example 210 by the method of Example 199, part A, to generate methyl hexahydro-7-oxo-b-(2-propenyl)-1H-azepine-2-butanoate.

211) This crude product of Example 211, part A, is then treated with triethyloxonium tetrafluoroborate (1.5 equivalents) in CH₂Cl₂ following the method of Example 3 to give the title compound.

EXAMPLE 212
methyl b-(2,3-dihydroxypropyl)hexahydro-7-imino-1H-azepine-2-butanoate, monohydrochloride

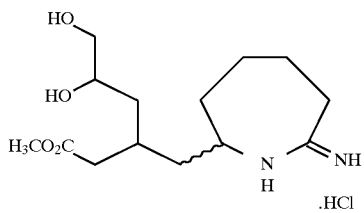

212 A) The title product of Example 211 dissolved in a 1:1 mixture of acetone and water and treated with osmium tetraoxide (2.5 equivalent %) and 4-methylmorpholine oxide (2 equivalents) at room temperature is allowed to stir overnight. The mixture is then carefully neutralized with dilute HCl, concentrated on a rotary evaporator, and extracted with 3 portions of EtOAc. The combined organic extracts are then dried (Na₂SO₄), stripped and purified by column chromatography on silica gel to yield methyl b-(2,3-dihydroxypropyl)-7-ethoxy-3,4,5,6-tetrahydro-2H-azepine-2-butanoate.

212) The product of Example 211 part A is treated with ammonium chloride in methanol following the method of Example 5 to give the title compound.

EXAMPLE 213
4-[(hexahydro-7-imino-1H-azepin-2-yl)methyl]-3,4,5,6-tetrahydro-6-hydroxy-2H-pyran-2-one, monohydrochloride

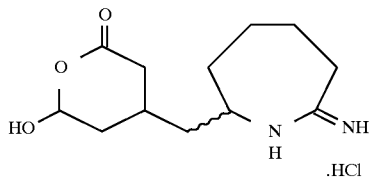

The amidine diol title product of Example 212 is dissolved in 0.5N HCl and warmed to 50° C. for 3 hours. The excess water and acid are then removed by lyophilization to give the title compound.

EXAMPLE 214
hexahydro-7-[(4-morpholinyl)methyl]-1H-azepin-2-imine, dihydrochloride

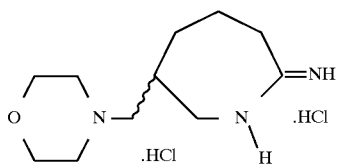

214 A) The title product of Example 78, Isomer-A, is converted to its Boc derivative, 1,1-dimethylethyl 2-ethenylhexahydro-7-oxo-1H-azepine-1-carboxylate, by the method of Example 185.

214 B) Treatment of the product of this Example, part A above, with ozone as described in example 209, part B, generates aldehyde product, 1,1-dimethylethyl 2-formylhexahydro-7-oxo-1H-azepine-1-carboxylate.

214 C) The product of this Example, part B above, in THF is reacted with morpholine in the presence H₂ and a metal catalyst to yield, 1,1-dimethylethyl hexahydro-2-[(4-morpholinyl)methyl]-7-oxo-1H-azepine-1-carboxylate.

214 D) The Boc group is removed from the product of this Example, part C above by the method of Example 199, part A, to generate hexahydro-7-[(4-morpholinyl)methyl]-1H-azepin-2-one.

214 E) This product of this Example, part D above is then treated with triethyloxonium tetrafluoroborate (1.1 equivalents) in CH₂Cl₂ following the method of Example 3 to give 7-ethoxy-3,4,5,6-tetrahydro-2-[(4-morpholinyl)methyl]-2H-azepine.

214) The crude product of this Example, part E above, is then reacted with ammonium chloride in methanol following the method of Example 5 and then with dilute HCl to produce the title compound.

EXAMPLE 215
hexahydro-2-imino-7-[(4-morpholinyl)methyl]-1H-azepin-3-ol, dihydrochloride

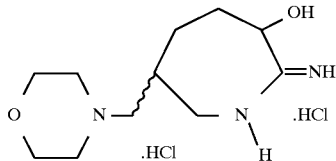

215 A) The product of Example 214, part A, 1,1-dimethylethyl 2-ethenylhexahydro-7-oxo-1H-azepine-1-carboxylate, is treated with an organo lithium base at low temperature to generate the enolate which is subsequently reacted with bis(trimethylsilyl)peroxide by the methods of F. A. Davis et al *Tettrahodron Lett.* 1988, 29, 4269 and L. Camici et al *Tettrahodron Lett.* 1988, 29, 4197 to yield 1,1-dimethylethyl hexahydro-3-hydroxy-7-[(4-morpholinyl)methyl]-2-oxo-1H-azepine-1-carboxylate.

215 B) Removal of the Boc protecting group by treatment of the product of this Example, part A above with dilute HCl gives the lactam hexahydro-3-hydroxy-7-[(4-morpholinyl)methyl]-1H-azepin-2-one.

215 C) The product of Example 215, part B is treated with acetic anhydride in the presence of pyridine to generate 3-acetyloxyhexahydro-7-[(4-morpholinyl)methyl]-1H-azepin-2-one.

215 D) The product of this Example, part C above is then treated with trimethyloxonium tetrafluoroborate (1.5 equivalents) in CH₂Cl₂ by the method of Example 3 to give 3,4,5,6-tetrahydro-7-methoxy-2-[(4-morpholinyl)methyl]-2H-azepin-3-ol acetate.

215) The crude product of this Example, part D above, is then reacted with ammonium chloride in methanol following the method of Example 5 and then with dilute HCl to produce the title compound.

EXAMPLE 216
5-[(hexahydro-7-imino-1H-azepin-2-yl)methyl]4,5-dihydroisoxazol-3-amine, dihydrochloride

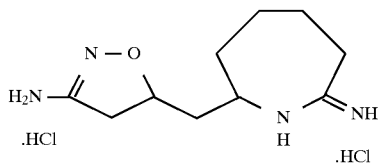

216 A) The title product isomer B of Example 18 (7-allyl caprolactam) is reacted with ethyl chlorooximinoyl acetate in toluene by the method of P. Caldirola, et. al., Heterocycles 1985, 23(10), 2479, to generate ethyl 5-[(hexahydro-7-oxo-1H-azepin-2-yl)methyl]-4,5-dihydroisoxazole-3-carboxylate.

216 B) The crude product of this Example, part A above, is hydrolyzed in aqueous HCl to generate 5-[(hexahydro-7-oxo-1H-azepin-2-yl)methyl]-4,5-dihydroisoxazole-3-carboxylic acid.

216 C) The crude product of this Example, part B above, is reacted with diphenylphosphoryl azide and triethylamine in benzene to generate 7-[(3-amino-4,5-dihydroisoxazol-5-yl)methyl]hexahydro-1H-azepin-2-one, monohydrochloride.

216 D) The crude product of this Example, part C above, is reacted with di-tert-butyldicarbonate in aqueous sodium hydroxide to generate 1,1-dimethylethyl [5-[(hexahydro-7-oxo-1H-azepin-2-yl)methyl]-4,5-dihydroisoxazol-3-yl] carbamate.

216 E) The crude product of this Example, part D above, is reacted with trimethyloxonium tetrafluoroborate by the method of Example 3 to generate the iminoether. The iminoether is reacted with ammonium chloride by the method of Example 5 to generate 1,1-dimethylethyl [5-[(hexahydro-7-imino-1H-azepin-2-yl)methyl]-4,5-dihydroisoxazol-3-yl]carbamate.

216) The crude product of this Example, part E above, is reacted with HCl/dioxane to generate the title compound.

EXAMPLE 217
5-[(hexahydro-7-imino-1H-azepin-2-yl)methyl]-1-methylpyrazolidin-3-one, dihydrochloride

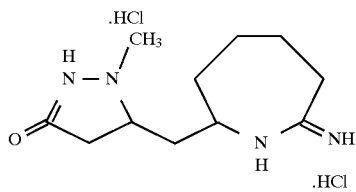

217 A) 1-morpholinocyclohexene is reacted with ethyl 4-bromocrotonate in 1,4-dioxane. The reaction mixture is diluted with water to generate ethyl 4-(2-oxocyclohexyl)-2-butenoate.

217 B) The crude product of this Example, part A above, is reacted with hydroxylamine-O-sulfonic acid to generate ethyl 4-(hexahydro-7-oxo-1H-azepin-2yl)-2-butenoate.

217 C) The crude product of this Example, part B above, is reacted with methylhydrazine to generate 7-[(4,5-dihydro-3-hydroxy-1-methyl-1H-pyrazol-5-yl)methyl]hexahydro-1H-azepin-2-one.

217 D) The crude product of this Example, part C above, is reacted with acetic anhydride to generate 7-[[3-(acetyloxy)-4,5-dihydro-1-methyl-1H-pyrazol-5-yl]methyl]hexahydro-1H-azepin-2-one.

217 E) The crude product of this Example, part D above, is reacted with trimethyloxonium tetrafluoroborate by the method of Example 3 to generate the iminoether. The iminoether is reacted with ammonium chloride by the method of Example 5 to generate 5-[(hexahydro-7-imino-1H-azepin-2-yl)methyl]-4,5-dihydro-1-methyl-1H-pyrazol-3-ol acetate, monohydrochloride.

217 F) The crude product of this Example, part E above, is heated in 2N HCl to generate the title compound.

EXAMPLE 218
5-[(hexahydro-7-imino-1H-azepin-2-yl)methyl]-1,2-dihydro-3H-pyrazol-3-one, dihydrochloride

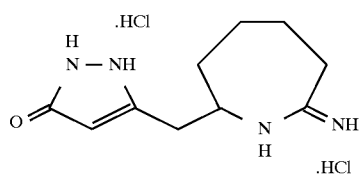

218 A) The title compound of Example 217, part B, is reacted with hydrazine to generate 7-[(4,5-dihydro-3-hydroxy-1H-pyrazol-5-yl)methyl]hexahydro-1H-azepin-2-one.

218 B) The crude product of this Example, part A above, is reacted with acetic anhydride to generate 7-[(3-acetyloxy-4,5-dihydro-1H-pyrazol-5-yl) methyl]hexahydro-1H-azepin-2-one.

218 C) The crude product of this Example, part B above, is reacted with DDQ by the method of E. W. Bousquet, J. Org. Chem. 1975, 40, 2208 to generate 7-[(3-acetyloxy-1H-pyrazol-5-yl)methyl]hexahydro-1H-azepin-2-one.

218 D) The crude product of this Example, part C above, is reacted with trimethyloxonium tetrafluoroborate by the method of Example 3 to generate the iminoether. The iminoether is reacted with ammonium chloride by the method of Example 5 to generate 7-[(3-acetyloxy-1H-pyrazol-5-yl)methyl]hexahydro-1H-azepin-2-imine, monohydro chloride.

218) The crude product of this Example, part D above, is heated in 2N HCl to generate the title compound.

EXAMPLE 219 AND EXAMPLE 64
Isomer A: (±)(cis) 4-methyl-5-(phenylmethyl)pyrrolidin-2-imine, monohydrochloride
Isomer B: (±) (trans) 4-methyl-5-(phenylmethyl)pyrrolidin-2-imine, monohydrochloride

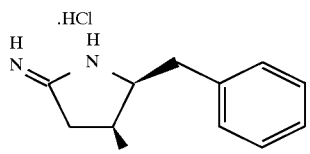

Example 219
Isomer A

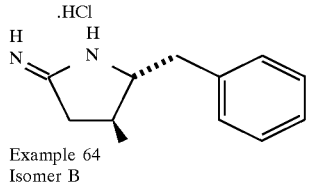

Example 64
Isomer B

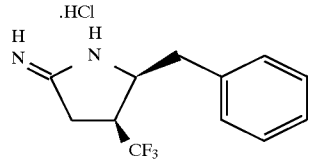

Isomer A

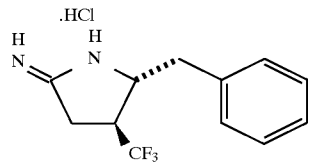

Isomer B

219 A) trans-b-Nitrostyrene (63.0 g, 0.42 mole) was reacted with benzaldehyde (53.4 g, 0.5 mole) and 1,2-diaminobenzene (54.4 g, 0.5 mole) according to the procedure of Chikashita et. al. (*Synth. Commun.* 1985, 15 (6), 527) to yield (2-nitroethyl)benzene (60.0 g, 95%) as a yellow oil.

219 B) Methyl crotonate (6.4 g, 64 mmol) was mixed with the product of Example 219 A (9.7 g, 64 mmol), potassium carbonate (8.9 g, 64 mmol) and Aliquat 336 (20 drops). The mixture was sonicated at room temperature. When the reaction, monitored by G.C., was complete, the mixture was acidified with HCl (1N) and the aqueous phase extracted with ether. The organic phase was dried ($Na_2SO_4$), filtered and stripped of solvent under reduced pressure to provide the crude product oil. Purification by chromatography on silica gel yielded methyl b-methyl-g-nitrobenzenepentanoate (14.7 g, 91%).

219 C) The product material from Example 219 B (5.0 g, 20 mmol) in absolute MeOH was hydrogenated over RaNi at 55° C. and 60 psi for 24 h. The reaction product was purified by column chromatography to yield 4-methyl-5-(phenylmethyl)pyrrolidin-2-one (2.4 g, 62%) as a mixture of diasteromers.

219 D) The products of Example 219 C (1.35 g, 7.0 mmol) were treated with trimethyloxonium tetrafluoroborate (1.26 g, 8.6 mmol) in $CH_2Cl_2$ (DCM, 20 mL) by the method of Example 3, to yield 3,4-dihydro-5-methoxy-3-methyl-2-(phenylmethyl)-2H-pyrrole (1.0 g, 67%) as a mixture of diastereomers.

219 and Example 64) A solution of the product of Example 219 D (1.0 g, 4.7 mmol) in MeOH (30 mL) was reacted with ammonium chloride (200 mg, 3.8 mmol) by the method of Example 5 followed by chromatography on reverse phase HPLC to generate the cis and trans title materials 219 (300 mg) and 64 (220 mg). The sample of trans isomer obtained by this method was identical to that obtained the method of Example 64.

DSC: 142.1° C. Elemental analysis: $C_{12}H_{16}N_2$.1.09 HCl (MW=228.01)

|  | C | H | N | Cl |
|---|---|---|---|---|
| Calculated: | 63.21 | 7.55 | 12.29 | 16.95 |
| Found: | 63.53 | 7.56 | 12.11 | 17.29 |

EXAMPLES 220

Isomer A: (±) (cis) 5-(phenylmethyl)-4-(trifluoromethyl)pyrrolidin-2-imine, monohydrochloride Isomer B: (±) (trans) 5-(phenylmethyl)-4-(trifluoromethyl)pyrrolidin-2-imine, monohydrochloride 220 A) Ethyl 4,4,4-trifluomethyl crotonate (5.5 g, 33 mmol) and the product of Example 219 A (5.0 g, 33 mmol) were reacted with potassium carbonate (4.6 g, 33 mmol) and Aliquat 336 (10 drops), by the method of Example 219 B. Purification by chromatography on silica gel yielded the product ethyl g-nitro-b-(trifluoromethyl) benzenepentanoate (4.4 g, 42%).

Elemental analysis: $C_{14}H_{16}NO_4F_3$ (MW=359.28)

|  | C | H | N |
|---|---|---|---|
| Calculated: | 52.67 | 5.05 | 4.39 |
| Found: | 52.81 | 5.40 | 4.31 |

220 B) The material 220 A (4.3 g, 13.5 mmol) in absolute MeOH was hydrogenated over RaNi at 55° C. and 60 psi for 16h. The reaction product was purified by column chromatography to yield 5-(phenylmethyl)-4-(trifluoromethyl)pyrrolidin-2-one (2.3 g, 71%) as a mixture of diasteromers.

220 C) The product material from Example 220 B (0.74 g, 3 mmol) was treated with trimethyloxonium tetrafluoroborate (0.54 g, 3.7 mmol) in DCM (20 mL) by the method of Example 3, to yield 3,4-dihydro-5-methoxy-2-(phenylmethyl)- 3-(trifluoromethyl)-2H-pyrrole (0.58 g, 76%) as a mixture of diastereomers.

220) A solution of the product of Example 220 C (0.6 g, 2.3 mmol) in MeOH (20 mL) was reacted with ammonium chloride (134 mg, 2.3 mmol) by the method of Example 5 followed by chromatography on reverse phase HPLC to generate the cis and trans title materials 220 Isomer A (240 mg) and 220 Isomer B (250 mg).

EXAMPLE 220

Isomer A:

Elemental analysis: $C_{12}H_{13}N_2F_3$.1 HCl.1.1 $NH_4Cl$.0.67 $H_2O$ (MW=349.62)

|  | C | H | N | Cl |
|---|---|---|---|---|
| Calculated: | 41.23 | 5.69 | 12.42 | 21.30 |
| Found: | 41.01 | 5.34 | 12.65 | 21.67 |

EXAMPLE 220

Isomer B:

Elemental analysis: $C_{12}H_{13}N_2F_3$.1 HCl.0.1 AcOH (MW=284.71)

| | C | H | N |
|---|---|---|---|
| Calculated: | 51.47 | 5.10 | 9.84 |
| Found: | 51.87 | 5.20 | 9.59 |

EXAMPLE 221

4,4-dimethyl-5-(phenylmethyl)pyrrolidin-2-imine, monohydrochloride

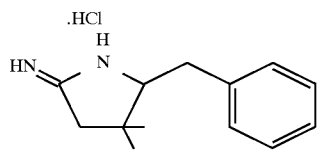

221 A) Ethyl dimethyl acrylate (10.75 g, 84 mmol) was mixed with the product of Example 219 A (12.68 g, 84 mmol), in tetra-n-butylammonium fluoride in THF (84 mL, 1M) and heated at 40° C. When the reaction, monitored by G.C., was complete, the mixture was treated with brine (satd.) and the aqueous phase extracted with ether. Purification by chromatography on silica gel yielded the product ethyl b,b-dimethyl-g-nitrobenzenepentanoate (9.04 g, 34%).

Elemental analysis: $C_{15}H_{21}NO_4$ (MW=279.34)

| | C | H | N |
|---|---|---|---|
| Calculated: | 64.50 | 7.58 | 5.01 |
| Found: | 64.60 | 7.96 | 4.96 |

221 B) The product material from Example 221 A (3.5 g, 12.5 mmol) in absolute MeOH was hydrogenated over RaNi at 55° C. and 60 psi for 6 h. The reaction product was purified by column chromatography to yield 4,4-dimethyl-5-(phenylmethyl)pyrrolidin-2-one (2.41 g, 95%).

221 C) The product material from Example 221 B (1.04 g, 5.1 mmol) was treated with trimethyloxonium tetrafluoroborate (0.91 g, 6.2 mmol) in DCM (25 mL) by the method of example 3, to yield 3,4-dihydro-5-methoxy-3,3-dimethyl-2-(phenylmethyl)-2H-pyrrole (0.83 g, 75%).

221) A solution of the product of Example 221 C (0.8 g, 3.5 mmol) in MeOH (60 mL) was reacted with ammonium chloride (187 mg, 3.5 mmol) by the method of Example 5 followed by chromatography on reverse phase HPLC to generate the title material (570 mg, 68%).

Elemental analysis: $C_{13}H_{18}N_2.1.0$ HCl (MW=238.76)

| | C | H | N | Cl |
|---|---|---|---|---|
| Calculated: | 65.40 | 3.02 | 11.73 | 14.35 |
| Found: | 65.04 | 7.78 | 11.85 | 14.75 |

EXAMPLE 222

5-(phenylmethyl)pyrrolidin-2-imine, monohydrochloride

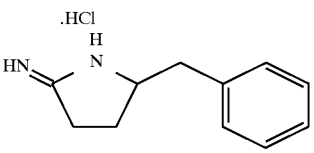

222 A) Methyl acrylate (2.8 g, 33 mmol) was mixed with the product of Example 219 A (5.0 g, 33 mmol), potassium carbonate (4.6 g, 33 mmol) and Aliquat 336 (10 drops), by the method of Example 219 B. Purification by chromatography on silica gel yielded 4.0 g (55%) of methyl g-nitrobenzenepentanoate.

Elemental analysis: $C_{12}H_{16}NO_4.0.05$ hexane (MW=242.57)

| | C | H | N |
|---|---|---|---|
| Calculated: | 61.16 | 6.55 | 5.80 |
| Found: | 61.54 | 6.52 | 6.16 |

222 B) The product material from Example 222 A (4.0 g, 18 mmol) was hydrogenated over Pd/C (4%) at 55° C. and 5 psi for 40 h. The reaction product was purified by column chromatography to yield 5-(phenylmethyl)pyrrolidin-2-one (0.6 g, 29%).

222 C) The product material of Example 222 B (0.5 g, 3.1 mmol) was treated with trimethyloxonium tetrafluoroborate (0.55 g, 3.7 mmol) in DCM (25 mL) by the method of Example 3, to yield 3,4-dihydro-5-methoxy-2-(phenylmethyl)-2H-pyrrole (0.5 g, 78%).

222) A solution of the title product of Example 222 C (0.5 g, 2.4 mmol) in MeOH (20 mL) was reacted with ammonium chloride (0.14 g, 2.7 mmol) by the method of Example 5. The crude product residue after removal of solvent was subjected to reverse phase HPLC to generate the title material (0.31 g, 55%). Elemental analysis: $C_{11}H_{14}N_2.1$ HCl.0.35$NH_4$Cl.0.25 $H_2O$ (MW=233.93)

| | C | H | N | Cl |
|---|---|---|---|---|
| Calculated: | 56.48 | 7.28 | 14.07 | 20.46 |
| Found | 56.43 | 7.48 | 14.38 | 20.83 |

EXAMPLES 223

Isomer A: (±) (cis) 5-[(1,3-dioxolan-2-yl)methyl]-4-(trifluoromethyl)pyrrolidin-2-imine, monohydrochloride Isomer B: (±) (trans) 5-[(1,3-dioxolan-2-yl)methyl]-4-(trifluoromethyl)pyrrolidin-2-imine, monohydrochloride

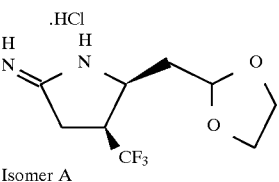

Isomer A

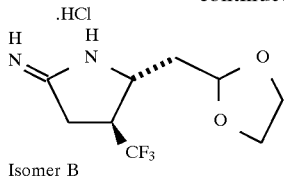

Isomer B

223 A) Ethyl 4,4,4-trifluomethyl crotonate (10 mmol) and 2-(2-nitroethyl)-1,3-dioxolane (12 mmol) are reacted with potassium carbonate (5 mmol) and Aliquat 336 (3 drops), by the method of Example 219 B. Purification by chromatography on silica gel yields ethyl g-nitro-b-(trifluoromethyl)-1,3-dioxolane-2-pentanoate.

223 B) The product material from Example 223 A in MeOH is hydrogenated over RaNi at 55° C. and 60 psi for 6 h. The reaction product is purified by column chromatography to yield 5-[(1,3-dioxolan-2-yl)methyl]-4-(trifluoromethyl)pyrrolidin-2-one as a mixture of diastereomers.

223 C) The product material from Example 223 B is treated with trimethyloxonium tetrafluoroborate in DCM by the method of Example 3 to yield 2-[(1,3-dioxolan-2-yl)methyl]- 3,4-dihydro-5-methoxy-3-(trifluoromethyl)-2H-pyrrole as a mixture of diastereomers.

223) A solution of the title products of Example 223 C in MeOH are reacted with ammonium chloride by the method of Example 5 followed by chromatography on reverse phase HPLC to generate the cis and trans title materials 223 Isomer A and 223 Isomer B.

EXAMPLES 224

Isomer A: (±)(trans) 2-[2-hydroxy-3-[5-imino-3-(trifluoromethyl)pyrrolidin-2-yl]propyl]oxazole-4-carboxylic acid, monohydrochloride Isomer B: (±) (cis) 2-[2-hydroxy-3-[5-imino-3-(trifluoromethyl)pyrrolidin-2-yl]propyl]oxazole-4-carboxylic acid, monohydrochloride

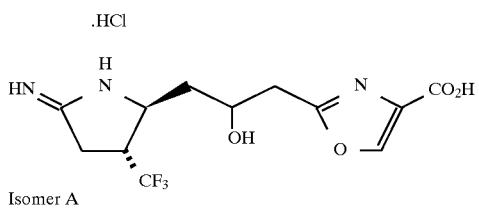

Isomer A

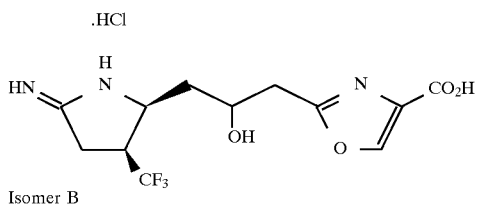

Isomer B

224 A) The product of Example 223 B in MeOH is treated with HCl (1N) to yield 5-oxo-3-(trifluoromethyl) pyrrolidine-2-acetaldehyde which is used directly in the next step.

224 B) As described by Helquist et al. in *J. Org. Chem.*, 1992, 57, 4799–4802, to a stirring suspension of Zn (7.5 mg-atm) and the product of 224 A (5.5 mmol) in 10 mL of THF at 0° C. is added dropwise ethyl 2-bromomethyloxazole-4-carboxylate (U.S. Pat. No. 5,395,932) (5.0 mmol) in 10 mL of THF. After stirring for 2 h, the reaction is quenched with saturated $NH_4Cl$ and extracted with $Et_2O$. The organic phase is dried over $MgSO_4$, concentrated under vacuum, and purified by column chromatography to give ethyl 2-[2-hydroxy-3-[5-oxo-3-(trifluoromethyl)pyrrolidin-2-yl]propyl]oxazole-4-carboxylate.

224 C) To a stirring solution of 224 B (5 mmol) in 10 mL of MeOH is added 10 mL of 1N NaOH. After 2 h, the reaction mixture is adjusted to pH 3 with 1M $KHSO_4$. The reaction mixture is extracted 3×50 mL of EtOAc. The combined organic layers are dried over $Na_2SO_4$ anhydrous, filtered, and stripped to give 2-[2-hydroxy-3-[5-oxo-3-(trifluoromethyl)pyrrolidin-2-yl]propyl] oxazole-4-carboxylic acid.

224 D) To a stirring solution of the product of Example 224 C (5 mmol) and imidazole (6 mmol) in 10 mL of DMF is added t-butyldimethylsilyl chloride (12 mmol). After 16 h, the solvent is removed under high vacuum and the residue is purified by column chromatography to provide (1,1-dimethylethyl)dimethylsilyl 2-[2-[(1,1-dimethylethyl)dimethylsilyloxy]-3-[5-oxo-3-(trifluoromethyl)pyrrolidin-2-yl]propyl]oxazole-4-carboxylate.

224 E) The product of Example 224 C is treated with trimethyloxonium tetrafluoroborate in DCM by the method of Example 3 to yield (1,1-dimethylethyl) dimethylsilyl 2-[3-[3,4-dihydro-5-methoxy-3-(trifluoromethyl)-2H-pyrrol-2-yl]-2-[(1,1-dimethylethyl) dimethylsiloxy]propyl]oxazole-4-carboxylate as a mixture of diastereomers.

224) A solution of the title products of Example 224 D in MeOH are reacted with ammonium chloride by the method of Example 5. The material is dissolved in HCl (2N) and refluxed for 2 h. The crude product residue after removal of solvent was subjected to reverse phase HPLC to generate both the cis and trans title materials 224 Isomer A and 224 Isomer B.

EXAMPLE 225

Isomer A: (±)ethyl (trans) 2-[3-[5-imino-3-(trifluoromethyl) pyrrolidin-2-yl]propyl]oxazole-4-carboxylate, monohydrochloride Isomer B: (±)ethyl (cis) 2-[3-[5-imino-3-(trifluoromethyl) pyrrolidin-2-yl]propyl]oxazole-4-carboxylate, monohydrochloride

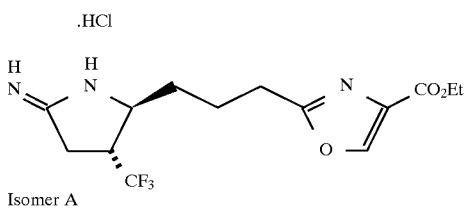

Isomer A

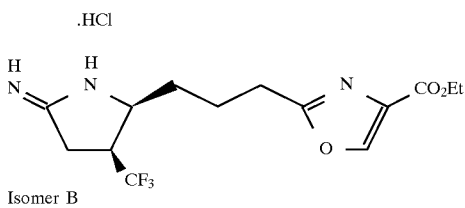

Isomer B

225A) To a stirring solution of the product of Example 224 B (5 mmol) in 10 mL of 10% TFA/DCM is added $Et_3SiH$ (7.5 mmol). After stirring for 30 min, the solvent is removed under vacuum and the residue is purified by column chromatography to provide ethyl 2-[3-[5-oxo-3-(trifluoromethyl)pyrrolidin-2-yl]propyl]oxazole-4-carboxylate.

225 B) The product material from Example 225 A is treated with trimethyloxonium tetrafluoroborate in DCM by the method of Example 3, to yield ethyl 2-[3-[3,4-dihydro-5-methoxy-3-(trifluoromethyl)-2H-pyrrol-2-yl]propyl]oxazole-4-carboxylate as a mixture of diastereomers.

225) A solution of the product of Example 225 B in MeOH is reacted with ammonium chloride by the method of Example 5. The crude product residue after removal of solvent was subjected to reverse phase HPLC to generate both the cis and trans title materials 225 Isomer A and 225 Isomer B.

EXAMPLE 226

Isomer A: (±)(trans) 2-[3-[5-imino-3-(trifluoromethyl)pyrrolidin-2-yl]propyl]oxazole-4-carboxylic acid, monohydrochloride Isomer B: (±) (cis) 2-[3-[5-imino-3-(trifluoromethyl)pyrrolidin-2-yl]propyl]oxazole-4-carboxylic acid, monohydrochloride

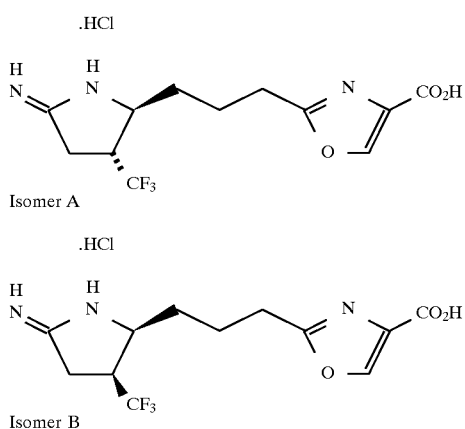

A solution of the crude title product mixture of Example 225 in HCl (2N) is reacted by the method of Example 224 E. The crude product residue after removal of solvent was subjected to reverse phase HPLC to generate the title material to generate both the cis and trans title materials 226 Isomer A and 226 Isomer B.

EXAMPLES 227

Isomer A: (±) (cis) 5-[(4-methoxyphenyl)methyl]-3-methylpyrrolidin-2-imine, monohydrochloride Isomer B: (±) (trans) 5-[(4-methoxyphenyl)methyl]-3-methylpyrrolidin-2-imine, monohydrochloride

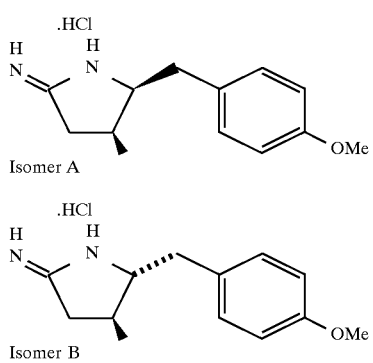

227 A) 4-Methoxy-b-nitrostyrene (25.0 g, 0.15 mole) was reacted with benzaldehyde (19.1 g, 0.18 mole) and 1,2-diaminobenzene (19.8 g, 0.18 mole) according to the procedure of Chikashita et. al. (*Synth. Commun.* 1985, 15 (6), 527) to yield methoxy-4-(2-nitroethyl)benzene (25.0 g, 93%) as a yellow oil.

227 B) Methyl crotonate (6.1 g, 61 mmol) was mixed with the product of Example 227 A (10 g, 61 mmol), potassium carbonate (8.4 g, 61 mmol) and Aliquat 336 (10 drops). The mixture was sonicated at room temperature. When the reaction, monitored by G.C., was complete the mixture was acidified with HCl (1N) and the aqueous phase extracted with ether. Purification by chromatography on silica gel gave methyl 4-methoxy-b-methyl-g-nitrobenzenepentanoate (6.7 g, 39%).

227 C) The product of Example 227 B (6.7 g, 24 mmol) in MeOH was hydrogenated over RaNi at 55° C. and 60 psi for 16 h. The reaction product was purified by column chromatography to yield 5-[(4-methoxyphenyl)methyl]-4-methylpyrrolidin-2-one (3.3 g, 67%) as a mixture of diasteromers.

227 D) The product from Example 227 C (1.4 g, 6.6 mmol) was treated with trimethyloxonium tetrafluoroborate (1.2 g, 7.5 mmol) in DCM by the method of Example 3, to yield 3,4-dihydro-5-methoxy-2-[(4-methoxyphenyl)methyl]-3-methyl-2H-pyrrole (1.4 g, 95%) as a mixture of diastereomers.

227) A solution of the title product of Example 227 D in MeOH is reacted with ammonium chloride by the method of Example 5. The crude product residue after removal of solvent was subjected to reverse phase HPLC to generate the cis and trans title materials 227 Isomer A and 227 Isomer B.

Biological Data

The activity of the above listed compounds as NO synthase inhibitors has been determined in the following assays:

Citrulline Assay for Nitric Oxide Synthase

Nitric oxide synthase activity was measured by monitoring the conversion of L-[2,3-3H]-arginine to L-[2,3-3H]-citrulline (1,2). The cDNA for human inducible NOS (hiNOS) was isolated from a lcDNA library made from RNA extracted from a colon sample from a patient with ulcerative colitis; human endothelial constitutive NOS (hecNOS) was isolated from a lcDNA library made from RNA extracted from human umbilical vein endothelial cells (HUVEC); and human neuronal constitutive NOS (hncNOS) was isolated from a lcDNA library made from RNA extracted from human cerebellum from a cadaver. The recombinant enzymes were expressed in insect cells using a baculovirus vector. Enzyme activity was isolated from cell extracts and partially purified by DEAE-Sepharose chromatography (2). Enzyme and inhibitors were added to give a volume of 50 $\mu$L in 50 mM Tris (pH 7.6) and the reaction initiated by the addition of 50 $\mu$L of a solution containing 50 mM Tris (pH 7.6), 2.0 mg/mL bovine serum albumin, 2.0 mM DTT, 4.0 mM CaCl2, 20 $\mu$M FAD, 100 $\mu$M tetrahydrobiopterin, 0.4–2.0 mM NADPH and 60 $\mu$M L-arginine containing 0.9 $\mu$Ci of L-[2,3-3H]-arginine. For constitutive NOS, calmodulin was included at a final concentration of 40–100 nM. Following incubation at 37° C. for 15 minutes, the reaction was terminated by addition of 300 $\mu$L cold buffer containing 10 mM EGTA, 100 mM HEPES (pH5.5) and 1.0 mM L-citrulline. The [3H]-citrulline was separated by chromatography on Dowex 50W X-8 cation exchange resin and radioactivity quantified with a liquid scintillation counter.

1. Bredt, D. S. and Snyder, S. H. (1990) Proc. Natl. Acad. Sci. U.S.A. 87, 682–685.
2. Misko, T. P., Moore, W. M., Kasten, T. P., Nickols, G. A., Corbett, J. A., Tilton, R. G., McDaniel, M. L., Williamson, J. R. and Currie, M. G. (1993) Eur. J. Pharm. 233, 119–125.

Raw Cell Nitrite Assay

RAW 264.7 cells are plated to confluency on a 96-well tissue culture plate grown overnight (17 h) in the presence of LPS to induce NOS. A row of 3–6 wells are left untreated and served as controls for subtraction of nonspecific background. The media is removed from each well and the cells are washed twice with Krebs-Ringers-Hepes (25 mM, pH 7.4) with 2 mg/ml glucose. The cells are then placed on ice and incubated with 50 μL of buffer containing L-arginine (30 μM) +/− inhibitors for 1 h. The assay is initiated by warming the plate to 37° C. in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. All values are the average of triplicate wells and are compared to a background-subtracted induced set of cells (100% value).

The following examples were assayed with the following results.

TABLE 1

| Example # | hiNOS | hecNOS | $IC_{50}$ (μM) hncNOS | RAW cell miNOS |
|---|---|---|---|---|
| 5 | 6.2 | 792 | 15 | 66 |
| 9 | 9.7 | 575 | 74 | >100 |
| 21 | 67% @ 10 μM | 10% @ 10 μM | 8.4 | 28 |
| 16 | 3.6 | 599 | 14 | 1.8 |
| 14 | 62 | 651 | 30 | 170 |
| 94 | 8.6 | 40 | 0.71 | 7.9 |
| 95 | 5.9 | 375 | 28 | |
| 34 | 8.1 | 183 | 24 | |
| 37 | 19 | 836 | 118 | 80 |
| 64 | 3.0 | 458 | 8.3 | 5.4 |
| 191 | 69% @ 10 μM | 11% @ 100 μM | 12% @ 10 μM | 45 |

In Vivo Assay

Rats were treated with an intraperitoneal injection of 10 mg/kg of endotoxin (LPS) with or without oral administration of the nitric oxice synthase inhibitors administered 1 hour prior to LPS. Plasma nitrites were measured 5 hours post-treatment. The results show that the administration of the nitric oxide synthase inhibitor decreases the rise in plasma nitrites, a reliable indicator of the production of nitric oxide, induced by endotoxin.

IP is the abbreviation for 2-iminopiperidine.

LPS is the abbreviation for endotoxin

TABLE II

% Inhibitor of Plasma Nitrites/Nitrates
Endotoxin in Rat Model
All compounds administered p.o. unless otherwise noted

| Example Number | % Inhibition (10 mg/kg) |
|---|---|
| 64 | 35 |
| 5 | 37 |

From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound having the formula:

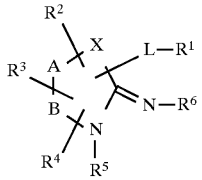

$R^1$ is a saturated or unsaturated $C_4$–$C_{10}$-heterocyclyl wherein 1 to about 4 carbon atoms are replace by nitrogen, oxygen or sulfur, and which may be optionally substituted by one or more of the following: $C_1$–$C_{10}$-alkyl, $C_2$–$C_{10}$-alkyenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, arylamino, aminoaryl, alkylaminoaryl, acylamino, amidino, carboxyl, carboalkoxy, carboaryloxy, carboarylalkyloxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, $C_1$–$C_{10}$-alkyl, amino, alkylamino, dialkylamino, aminoalkyl, aminoacyl, carboxyl, carboalkoxy, carboaryloxy, carboalkylaryloxy, hydroxy, $C_1$–$C_{10}$-alkoxy;

L is selected from the group consisting of $C_1$–$C_{10}$-alkylene, $C_2$–$C_{10}$-alkenylene, $C_2$–$C_{10}$-alkynylene, and —$(CH_2)_m$—D—$(CH_2)_n$—;

D is selected from the group consisting of O, S, SO, $SO_2$, $SO_2NR^7$, $NR^7SO_2$, $NR^8$, $POOR^7$, $PON(R^7)_2$, $POOR^7NR^7$, $NR^7POOR^7$;

$R^7$ is hydrogen or $C_1$–$C_{10}$-alkyl;

$R^8$ is hydrogen, $C_1$–$C_{10}$-alkyl, $COR^9$, or $CO_2R^9$;

$R^9$ is $C_1$–$C_{10}$-alkyl;

m=1 to about 7;

n=0 to about 5;

wherein L may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, arylamino, acylamino, carboxyl, carboalkoxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: $C_1$–$C_{10}$-alkyl, amino, alkylamino, dialkylamino, aminoalkyl, aminoacyl, carboxyl, carboalkoxy, hydroxy, $C_1$–$C_{10}$-alkoxy;

X is $(CH_2)_2$ when A is $(CH_2)_2$ and B is $CH_2$; or

X is $CH_2$ when A is $(CH_2)_2$ and B is CH=CH; or

X is $CH_2$ when A is CH=CH and B is $(CH_2)_2$; or

X is $(CH_2)_2$ when A is CH=CH and B is $CH_2$; or

X is CH=CH when A is CH=CH and B is $CH_2$; or

X is CH=CH when A is $(CH_2)_2$ and B is $CH_2$; or

X is CH when A is CH=CH and B is CH=CH; or

X is CH=CH when A is $CH_2$ and B is CH=CH;

$R^2$, $R^3$, and $R^4$ are independently selected from $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, halogen, nitro, amino, alkylamino, dialkylamino, aminoalkyl, dialkylaminoalkyl, acylamino, carboxyl, carboalkoxy, cyano, aminocarbonylalkoxy, aminocarbonylamino, aminocarbonylaminoalkyl, haloalkyl, $SO_2NR^7R^9$, wherein all said substitutions may be optionally substituted with one or more of the following: halogen, $C_1$–$C_{10}$-alkyl, amino, alkylamino, dialkylamino, aminoalkyl, aminoacyl, carboxyl, carboalkoxy, hydroxy, $C_1$–$C_{10}$-alkoxy, and $R^2$, $R^3$, may optionally be taken together to form a $C_3$–$C_{10}$-alicyclic hydrocarbon, $C_4$–$C_{10}$-heterocyclyl or aromatic hydrocarbon and said optionally formed ring may be optionally substituted with one or more of the following:
  $C_1$–$C_{10}$-alkyl, $C_2$–$C_{10}$-alkenyl, $C_2$–$C_{10}$-alkynyl which may be optionally substituted with carboxyl, carboalkoxy, and $C_1$–$C_{10}$-alkoxy; and $R^5$, $R^6$ are independently selected from the group consisting of hydrogen, hydroxy, and alkyloxy.

2. The compound as recited in claim 1 wherein:
$R^1$ is a saturated or unsaturated $C_4$–$C_{10}$-heterocyclyl wherein 1 to about 4 carbon atoms are replaced by nitrogen, oxygen or sulfur, and which may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, amino, amidino, alkylamino, aminoalkyl, aminoaryl, carboxyl, carboalkoxy, carboaryloxy, aminocarbonylalkoxy, aminocarbonylamino, $SO_2NR^7R^9$, wherein all said substitutions may be optionally substituted with one or more of the following: $C_1$–$C_{10}$-alkyl, amino, alkylamino, aminoalkyl, aminoacyl, carboxyl, carboalkoxy, carboaryloxy, carboalkylaryloxy, hydroxy, $C_1$–$C_{10}$-alkoxy;

L is selected from the group consisting of $C_1$–$C_{10}$-alkylene, $C_2$–$C_{10}$-alkenylene, $C_2$–$C_{10}$-alkynylene, and —$(CH_2)_m$—D—$(CH_2)_n$—;

D is selected from the group consisting of O, S, SO, $SO_2$, $NR^8$, and $POOR^7$;

$R^7$ is hydrogen or $C_1$–$C_{10}$-alkyl;

$R^8$ is hydrogen, $C_1$–$C_{10}$-alkyl, $COR^9$, or $CO_2R^9$;

$R^9$ is $C_1$–$C_{10}$-alkyl;

m=1 to about 4;

n=0 to about 3;

wherein L may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, nitro, amino, alkylamino, aminoalkyl, arylamino, aminoaryl, carboxyl, carboalkoxy, carboaryloxy, aminocarbonylalkoxy, aminocarbonylamino, $SO_2NR^7R^9$, wherein all said substitutions may be optionally substituted with one or more of the following: $C_1$–$C_{10}$-alkyl, amino, alkylamino, aminoalkyl, aminoacyl, carboxyl, carboalkoxy, carboaryloxy, carboalkylaryloxy, hydroxy, $C_1$–$C_{10}$-alkoxy;

$R^2$, $R^3$, and $R^4$ are independently selected from $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$thioalkoxy, $S(O)R^9$, $S(O)_2R^9$, alkylamino, aminoalkyl, carboxyl, carboalkoxy, aminocarbonylalkoxy, aminocarbonylamino, $SO_2NR^7R^9$, wherein all said substitutions may be optionally substituted with one or more of the following: halogen, $C_1$–$C_{10}$-alkyl, amino, alkylamino, aminoalkyl, aminoacyl, carboxyl, carboalkoxy, carboaryloxy, carboalkylaryloxy, hydroxy, and $C_1$–$C_{10}$-alkoxy, and $R^2$, $R^3$, may optionally be taken together to form a $C_3$–$C_{10}$-alicyclic hydrocarbon, $C_4$–$C_{10}$-heterocyclyl or aromatic hydrocarbon; and $R^5$, $R^6$ are independently selected from the group consisting of hydrogen, hydroxy, and alkyloxy.

3. The compound as recited in claim 2 wherein:
$R^1$ is a saturated or unsaturated $C_4$–$C_{10}$-heterocyclyl wherein 1 to about 4 carbon atoms are replaced by nitrogen, oxygen or sulfur, and which may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, amino, aminoalkyl, aminoaryl, carboxyl, carboalkoxy, carboaryloxy, aminocarbonylalkoxy, aminocarbonylamino, $SO_2NR^7R^9$, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

L is selected from the group consisting of $C_1$–$C_{10}$-alkylene, $C_2$–$C_{10}$-alkenylene, $C_2$–$C_{10}$-alkynylene, and —$(CH_2)_m$—D—$(CH_2)_n$—;

D is selected from the group consisting of O, S, SO, $SO_2$, and $NR^8$;

$R^7$ is hydrogen or $C_1$–$C_{10}$-alkyl;

$R^8$ is hydrogen, $C_1$–$C_{10}$-alkyl, $COR^9$, or $CO_2R^9$;

$R^9$ is $C_1$–$C_{10}$-alkyl;

m=1 to about 4;

n=0 to about 3;

wherein L may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, amino, aminoalkyl, aminoaryl, carboxyl, carboalkoxy, carboaryloxy, aminocarbonylalkoxy, aminocarbonylamino, $SO_2NR^7R^9$, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

$R^2$, $R^3$, and $R^4$ are independently selected from $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, $S(O)R^9$, $S(O)_2R^9$, amino, aminoalkyl, carboxyl, carboalkoxy, aminocarbonylalkoxy, aminocarbonylamino, $SO_2NR^7R^9$, wherein all said substitutions may be optionally substituted with one or more of the following: $C_1$–$C_{10}$-alkyl, amino, aminoalkyl, aminoacyl, carboxyl, carboalkoxy, hydroxy, and $C_1$–$C_{10}$-alkoxy; and $R^5$, $R^6$ are independently selected from the group consisting of hydrogen, hydroxy, and alkyloxy.

4. The compound as recited in claim 3 wherein:
$R^1$ is a saturated or unsaturated $C_4$–$C_{10}$-heterocyclyl wherein 1 to about 4 carbon atoms are replaced by nitrogen, oxygen or sulfur, and which may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

L is selected from the group consisting of $C_1$–$C_{10}$-alkylene, $C_2$–$C_{10}$-alkenylene, and $C_2$–$C_{10}$-alkynylene;

wherein L may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

$R^2$, $R^3$, and $R^4$ are independently selected from $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, carboxyl, carboalkoxy, carboaryloxy, aminocarbonylalkoxy, aminocarbonylamino, wherein all said substitutions may be optionally substituted with one or more of the following: $C_1$–$C_{10}$-alkyl, amino, aminoalkyl, aminoacyl, carboxyl, carboalkoxy, hydroxy, and $C_1$–$C_{10}$-alkoxy; and $R^5$, $R^6$ are independently selected from the group consisting of hydrogen, hydroxy, and alkyloxy.

5. The compound as recited in claim 4 wherein:

$R^1$ is a saturated or unsaturated $C_4$–$C_{10}$-heterocyclyl wherein 1 to about 4 carbon atoms are replaced by nitrogen, oxygen or sulfur, and which may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, aminoaryl, carboxyl, carboalkoxy, carboaryloxy, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

L is selected from the group consisting of $C_1$–$C_{10}$-alkylene, $C_2$–$C_{10}$-alkenylene, and $C_2$–$C_{10}$-alkynylene;

wherein L may be optionally substituted by one or more of the following: $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, carboxyl, carboalkoxy, carboaryloxy, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, $C_1$–$C_{10}$-alkoxy;

$R^2$, $R^3$, and $R^4$ are independently selected from $C_1$–$C_{10}$-alkyl, $C_2$–$C_{10}$-alkenyl, $C_2$–$C_{10}$-alkynyl, hydroxy, $C_1$–$C_{10}$-alkoxy, thiol, $C_1$–$C_{10}$-thioalkoxy, amino, aminoalkyl, carboxyl, carboalkoxy, wherein all said substitutions may be optionally substituted with one or more of the following: $C_1$–$C_{10}$-alkyl, amino, aminoalkyl, aminoacyl, carboxyl, carboalkoxy, carboaryloxy, hydroxy, and $C_1$–$C_{10}$-alkoxy; and $R^5$, $R^6$ are independently selected from the group consisting of hydrogen, hydroxy, and alkyloxy.

6. A compound selected from the group consisting of [(1,4-benzodioxan-2-yl)methyl]hexahydro-1H-azepin-2-imine, monohydrochloride; hexahydro-7-[(tetrahydro-2-furanyl)methyl]-1H-azepin-2-imine, monohydrochloride; hexahydro-3-[(tetrahydro-2-furanyl)methyl]-1H-azepin-2-imine, monohydrochloride; 7-[(2-furanyl)methyl] hexahydro-1H-azepin-2-imine, monohydrochloride; hexahydro-7-[(2-thienyl)methyl]-1H-azepin-2-imine, monohydrochloride; hexahydro-3-[(2-thienyl)methyl]-1H-azepin-2-imine, monohydrochloride; 7-[2-(1,3-dioxolan-2-yl)ethyl]hexahydro-1H-azepin-2-imine, monohydrochloride; 7-[2-(1,3-dioxan-2-yl)ethyl]hexahydro-1H-azepin-2-imine, monohydrochloride; 7-[2-(1,3-dioxan-2-yl)ethyl] hexahydro-1H-azepin-2-imine, monohydrochloride; 7-[[4,5-dihydro-3-(trifluoromethyl)isoxazol-5-yl]methyl] hexahydro-1H-azepin-2-imine, monohydrochloride; 7-[[4,5-dihydro-3-(trifluoromethyl)isoxazol-4-yl]methyl] hexahydro-1H-azepin-2-imine, monohydrochloride; hexahydro-7-[[3-(trifluoromethyl)isoxazol-5-yl]methyl]-1H-azepin-2-imine, monohydrochloride; hexahydro-7-[[3-(trifluoromethyl)isoxazol-4-yl]methyl]-1H-azepin-2-imine, monohydrochloride; hexahydro-7-[(3-phenylisoxazol-4-yl) methyl]-1H-azepin-2-imine, monohydrochloride; hexahydro-7-[(3-phenylisoxazol-5-yl)methyl]-1H-azepin-2-imine, monohydrochloride; 7-[[4,5-dihydro-1-phenyl-3-(trifluoromethyl)-1H-pyrazol-5-yl]methyl]-hexahydro-1H-azepin-2-imine, monohydrocloride; hexahydro-7-[[1-phenyl-3-(trifluoromethyl)-1H-pyrazol-5-yl]methyl]-1H-azepin-2-imine, monohydrocloride; hexahydro-7-[[1-phenyl-3-(trifluoromethyl)-1H-pyrazol-r-yl]methyl]-1H-azepin-2-imine, monohydrochloride; 7-[[4,5-dihydro-1,3-diphenyl-1H-pyrazol-4-yl]methyl]hexahydro-1H-azepin-2-imine, monohydrochloride; 7-[(1 ,3-diphenyl-1H-pyrazol-5-yl)methyl]hexahydro-1H-azepin-2-imine, monohydrochloride; hexahydro-7-[[1-phenyl-3-(trifluoromethyl)-1H-1,2,4-triazol-5-yl]methyl]-1H-azepin-2-imine, monohydrochloride; 7-[2-(3-furanyl)ethyl] hexahydro-1H-azepin-2-imine, monohydrochloride; hexahydro-7-[2-(2-thienyl-ethenyl)-1H-azepin-2-imine, monohydrochloride; hexahydro-7-[2-(2-thienyl)ethyl]-1H-azepin-2-imine, monohydrochloride; methyl 5-[3-(hexahydro-7-imino-1H-azepin-2-yl)-1-propenyl]furan-2-carboxylate, monohydrochloride; methyl 5-[3-(hexahydro-7-imino-1H-azepin-2-yl)propyl]furan-2-carboxylate, monohydrochloride; hexahydro-7-[2-(2-thiazolyl)ethenyl]-1H-azepin-2-imine, monohydrochloride ; hexahydro-7-[2-(2-thiazolyl)ethyl]-1H-azepin-2-imine, monohydrochloride; 7-[(4,5-dihydro-3-phenylisoxazolyl-5-yl)methyl] hexahydro-1H-azepine-2-imine, monotrifluoroacetic acid salt; 7-[(5-chlorothien-2-yl)methyl]-hexahydro-1-H-azepin-2-imine; 7-[(3,5-dimethylisoxazol-4-yl)methyl]hexahydro-1H-azepin-2-imine; hexahydro-7-[(tetrahydro-2H-pyran-2-yl)methyl]-1H-azepin-2-imine; hexahydro-3-[(tetrahydro-2H-pyran-2-yl)methyl]-1H-azepin-2-imine; 7-[3-[5-(1,3-dioxolan-2-yl)thien-2-yl)-2-propenyl]hexahydro-1H-azepin-2-imine, monohydrochloride; 5-[3-(hexahydro-7-imino-1H-azepin-2-yl)-1-propenyl]thiophene-2-carboxamide, monohydrochloride; b-(2-furanyl)hexahydro-7-imino-1H-azepine-2-propanenitrile, monohydrochloride; methyl b-(2-furanyl)hexahydro-7-imino-1H-azepine-2-propanoate, monohydrochloride; g-(2-furanyl)hexahydro-7-imino-1H-azepine-2-propanamine, dihydrochloride; N-[3-(2-furanyl)-3-(hexahydro-7-imino-1H-azepin-2-yl)propyl] methanesulfonamide, monohydrochloride; 4-[(hexahydro-7-imino-1H-azepin-2-yl)methyl]-3,4,5,6-tetrahydro-6-hydroxy-2H-pyran-2-one, monohydrochloride; hexahydro-7-[(4-morpholinyl)methyl]-1H-azepin-2-imine, dihydrochloride; hexahydro-2-imino-7-[(4-morpholinyl) methyl]-1H-azepin-3-ol, dihydrochloride; 5-[(hexahydro-7- imino-1H-azepin-2-yl)methyl]4,5-dihydroisoxazol-3-amine, dihydrochloride; 5-[(hexahydro-7-imino-1H-azepin-2-yl)methyl]-1-methylpyrazolidin-3-one, dihydrochloride; 5-[(hexahydro-7-imino-1H-azepin-2-yl)methyl]-1,2-dihydro-3H-pyrazol-3-one, dihydrochloride; (±) (cis) 5-[(1,3-dioxolan-2-yl)methyl]-4-(trifluoromethyl)pyrrolidin-2-imine, monohydrocloride; (±) (trans) 5-[(1,3-dioxolan-2-yl)methyl]-4-(trifluoromethyl)pyrrolidin-2-imine, monohydrochloride; (±) (trans) 2-[2-hydroxy-3-[5-imino-3-(trifluoromethyl)pyrrolidin-2-yl]propyl]oxazole-4-carboxylic acid, monohydrochloride; (±) (cis) 2-[2-hydroxy-3-[5-mino-3-(trifluoromethyl)pyrrolidin-2-yl]propyl]oxazole-4-carboxylic acid, monohydrochloride; (±)ethyl (trans) 2-[3-[5-imino-3-(trifluoromethyl)pyrrolidin-2-yl]propyl]oxazole-4-carboxylate, monohydrochloride; (±)ethyl (cis) 2-[3-[5-imino-3-(trifluoromethyl)pyrrolidin-2-yl]propyl]oxazole-4-carboxylate, monohydrochloride; (±) (trans) 2-[3-[5-imino-3-(trifluoromethyl)pyrrolidin-2-yl]propyl]oxazole-4-carboxylic acid, monohydrochloride; (±) (cis) 2-[3-[5-imino-3-(trifluoromethyl)pyrrolidin-2-yl]propyl]oxazole-4-carboxylic acid, monohydrochloride.

\* \* \* \* \*